United States Patent
Anderson et al.

(10) Patent No.: US 8,425,514 B2
(45) Date of Patent: Apr. 23, 2013

(54) SPINAL FIXATION DEVICE

(75) Inventors: Mark E. Anderson, Irvine, CA (US); Paul A. Munoz, Laguna Beach, CA (US)

(73) Assignee: WestMark Medical, LLC., Irvine, CA (US)

( * ) Notice: Subject to any disclaimer, the term of this patent is extended or adjusted under 35 U.S.C. 154(b) by 1272 days.

(21) Appl. No.: 12/146,291

(22) Filed: Jun. 25, 2008

(65) Prior Publication Data

US 2009/0326580 A1 Dec. 31, 2009

(51) Int. Cl.
*A61B 17/56* (2006.01)
*A61B 17/58* (2006.01)
*A61B 17/80* (2006.01)
*A61F 2/44* (2006.01)

(52) U.S. Cl.
USPC ............ 606/70; 606/71; 606/280; 623/17.11

(58) Field of Classification Search .... 623/17.11–17.16; 606/246–260, 279
See application file for complete search history.

(56) References Cited

U.S. PATENT DOCUMENTS

| | | | |
|---|---|---|---|
| 2,037,586 A | 4/1936 | Olson | |
| 2,980,275 A | 4/1961 | Lundgren | |
| 3,297,049 A | 1/1967 | Moskovitz | |
| 3,517,717 A | 6/1970 | Orlomoski | |
| 3,729,757 A | 5/1973 | Wright | |
| 3,741,205 A | 6/1973 | Markolf et al. | |
| 4,038,801 A * | 8/1977 | Busch | 52/698 |
| 4,388,921 A | 6/1983 | Sutter et al. | |
| 4,484,570 A | 11/1984 | Sutter et al. | |
| 5,007,910 A | 4/1991 | Anapliotis et al. | |
| 5,030,220 A | 7/1991 | Howland | |
| 5,057,111 A * | 10/1991 | Park | 606/288 |
| 5,180,381 A | 1/1993 | Aust et al. | |
| 5,344,421 A | 9/1994 | Crook | |
| 5,364,399 A | 11/1994 | Lowery et al. | |
| 5,486,176 A | 1/1996 | Hildebrand et al. | |
| 5,501,684 A | 3/1996 | Schlapfer et al. | |

(Continued)

FOREIGN PATENT DOCUMENTS

| | | |
|---|---|---|
| WO | WO8803781 | 6/1988 |
| WO | WO0200124 | 1/2002 |

(Continued)

OTHER PUBLICATIONS

International Search Report for international application No. PCT/US2009/048209.

*Primary Examiner* — Eduardo C Robert
*Assistant Examiner* — James Palmer
(74) *Attorney, Agent, or Firm* — Stetina Brunda Garred & Brucker; Lowell Anderson

(57) ABSTRACT

A spinal fixation assembly has a bone screw with head having a continuously curved spherical outer surface. The curved surface nests in a split annular bushing having a plurality of segments curving around the screw head. The bushing has an outward extending flange that fits into a recess in a socket in a fixation plate. The plate has at least three legs which extend from ends of a cross-member to form one of an H shaped, X shaped or A shaped configuration. Each socket is curved to rotatably receive rotation of the bushing. The socket recess is larger than the bushing flange to allow the bushing to tilt a predetermined amount depending on a thickness of the outward extending flange.

22 Claims, 46 Drawing Sheets

U.S. PATENT DOCUMENTS

| | | | |
|---|---|---|---|
| 5,531,746 A | 7/1996 | Errico et al. | |
| 5,534,027 A | 7/1996 | Hodorek | |
| 5,549,608 A | 8/1996 | Errico et al. | |
| 5,549,612 A | 8/1996 | Yapp et al. | |
| 5,569,251 A | 10/1996 | Baker | |
| 5,578,034 A | 11/1996 | Estes | |
| 5,603,713 A | 2/1997 | Aust et al. | |
| 5,607,426 A | 3/1997 | Ralph et al. | |
| 5,609,592 A | 3/1997 | Brumfield et al. | |
| 5,616,144 A | 4/1997 | Yapp et al. | |
| 5,681,311 A | 10/1997 | Foley | |
| 5,718,705 A | 2/1998 | Sammarco | |
| 5,725,588 A | 3/1998 | Errico et al. | |
| 5,735,853 A | 4/1998 | Olerud | |
| 5,741,255 A * | 4/1998 | Krag et al. | 606/264 |
| 5,782,919 A | 7/1998 | Zdeblick et al. | |
| 5,876,402 A | 3/1999 | Errico | |
| 5,931,838 A | 8/1999 | Vito | |
| 5,954,722 A | 9/1999 | Bono | |
| 6,017,345 A | 1/2000 | Richelsoph | |
| 6,080,193 A | 6/2000 | Hochshuler | |
| 6,086,614 A | 7/2000 | Mumme | |
| 6,129,730 A | 10/2000 | Bono et al. | |
| 6,139,550 A | 10/2000 | Michelson | |
| 6,143,033 A | 11/2000 | Paul et al. | |
| 6,152,927 A | 11/2000 | Farris et al. | |
| 6,187,005 B1 | 2/2001 | Brace et al. | |
| 6,206,882 B1 * | 3/2001 | Cohen | 606/283 |
| 6,235,033 B1 | 5/2001 | Brace et al. | |
| 6,235,034 B1 | 5/2001 | Bray | |
| 6,258,089 B1 | 7/2001 | Campbell et al. | |
| 6,277,120 B1 | 8/2001 | Lawson | |
| 6,280,443 B1 | 8/2001 | Gu et al. | |
| 6,331,179 B1 | 12/2001 | Freid et al. | |
| 6,342,055 B1 | 1/2002 | Eisermann et al. | |
| RE37,665 E | 4/2002 | Ralph et al. | |
| 6,383,186 B1 | 5/2002 | Michelson | |
| 6,398,783 B1 | 6/2002 | Michelson | |
| 6,413,259 B1 | 7/2002 | Lyons et al. | |
| 6,454,769 B2 | 9/2002 | Wagner et al. | |
| 6,461,359 B1 | 10/2002 | Tribus et al. | |
| 6,503,250 B2 | 1/2003 | Paul | |
| 6,533,786 B1 | 3/2003 | Needham et al. | |
| 6,575,975 B2 | 6/2003 | Brace et al. | |
| 6,579,318 B2 | 6/2003 | Varga et al. | |
| 6,579,319 B2 | 6/2003 | Goble et al. | |
| 6,592,586 B1 | 7/2003 | Michelson | |
| 6,599,290 B2 | 7/2003 | Baily et al. | |
| 6,602,255 B1 | 8/2003 | Campbell et al. | |
| 6,605,090 B1 | 8/2003 | Trieu et al. | |
| 6,613,053 B1 | 9/2003 | Collins et al. | |
| 6,620,163 B1 | 9/2003 | Michelson | |
| 6,626,907 B2 | 9/2003 | Campbell et al. | |
| 6,656,181 B2 | 12/2003 | Dixon et al. | |
| 6,666,867 B2 | 12/2003 | Ralph et al. | |
| 6,669,700 B1 | 12/2003 | Farris et al. | |
| 6,682,563 B2 | 1/2004 | Scharf | |
| 6,689,134 B2 | 2/2004 | Ralph et al. | |
| 6,692,503 B2 | 2/2004 | Foley et al. | |
| 6,695,846 B2 | 2/2004 | Richelsoph et al. | |
| 6,699,249 B2 | 3/2004 | Schlapfer et al. | |
| 6,730,127 B2 | 5/2004 | Michelson | |
| 6,764,489 B2 | 7/2004 | Ferree | |
| 6,830,570 B1 | 12/2004 | Frey et al. | |
| 6,837,905 B1 | 1/2005 | Lieberman | |
| 6,843,790 B2 | 1/2005 | Ferree | |
| 6,890,335 B2 | 5/2005 | Grabowski et al. | |
| 6,932,820 B2 | 8/2005 | Osman | |
| 6,964,664 B2 | 11/2005 | Freid et al. | |
| 6,969,390 B2 | 11/2005 | Michelson | |
| 7,001,387 B2 | 2/2006 | Farris et al. | |
| 7,001,389 B1 | 2/2006 | Navarro et al. | |
| 7,025,769 B1 | 4/2006 | Ferree | |
| 7,044,952 B2 | 5/2006 | Michelson | |
| 7,048,739 B2 | 5/2006 | Konieczynski et al. | |
| 7,112,222 B2 | 9/2006 | Fraser et al. | |
| 7,166,111 B2 | 1/2007 | Kolb et al. | |
| 7,169,150 B2 | 1/2007 | Shipp et al. | |
| 7,175,624 B2 | 2/2007 | Konieczynski et al. | |
| 7,204,837 B2 | 4/2007 | Paul | |
| 7,220,263 B2 | 5/2007 | Cordaro | |
| 7,255,699 B2 | 8/2007 | Paul | |
| 7,303,564 B2 | 12/2007 | Freid | |
| 7,306,605 B2 * | 12/2007 | Ross | 606/70 |
| 7,335,201 B2 * | 2/2008 | Doubler et al. | 606/264 |
| 7,909,859 B2 | 3/2011 | Mosca et al. | |
| 7,931,678 B2 | 4/2011 | Konieczynski et al. | |
| 2001/0037112 A1 * | 11/2001 | Brace et al. | 606/69 |
| 2002/0151899 A1 | 10/2002 | Bailey et al. | |
| 2003/0199876 A1 | 10/2003 | Brace et al. | |
| 2003/0225409 A1 | 12/2003 | Freid et al. | |
| 2004/0019353 A1 | 1/2004 | Freid | |
| 2004/0092939 A1 | 5/2004 | Freid | |
| 2005/0096657 A1 * | 5/2005 | Autericque et al. | 606/69 |
| 2006/0200134 A1 | 9/2006 | Freid | |
| 2006/0235403 A1 | 10/2006 | Blain | |
| 2006/0235409 A1 | 10/2006 | Blain | |
| 2006/0235411 A1 | 10/2006 | Blain | |
| 2006/0235412 A1 | 10/2006 | Blain | |
| 2006/0235518 A1 | 10/2006 | Blain | |
| 2006/0235533 A1 | 10/2006 | Blain | |
| 2006/0287653 A1 | 12/2006 | Rhyne | |
| 2007/0055252 A1 | 3/2007 | Blain et al. | |
| 2007/0055257 A1 * | 3/2007 | Vaccaro et al. | 606/73 |
| 2007/0093831 A1 | 4/2007 | Abdelgany et al. | |
| 2007/0225718 A1 | 9/2007 | Ensign | |
| 2008/0065070 A1 | 3/2008 | Freid | |
| 2009/0118831 A1 * | 5/2009 | Trieu | 623/17.11 |

FOREIGN PATENT DOCUMENTS

| | | |
|---|---|---|
| WO | WO0200124 A | 1/2002 |
| WO | WO03063714 A1 | 8/2003 |
| WO | WO2006060506 A1 | 6/2006 |
| WO | W02006101837 A | 9/2006 |
| WO | WO2006101837 A2 | 9/2006 |
| WO | WO2007076050 A1 | 7/2007 |
| WO | W02009114014 A1 | 9/2009 |

* cited by examiner

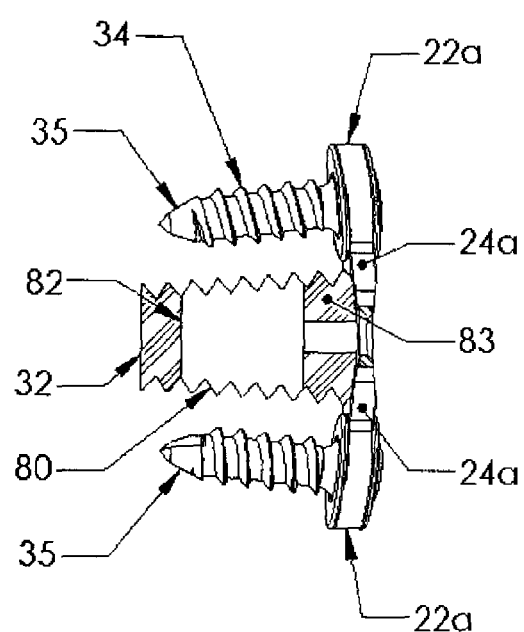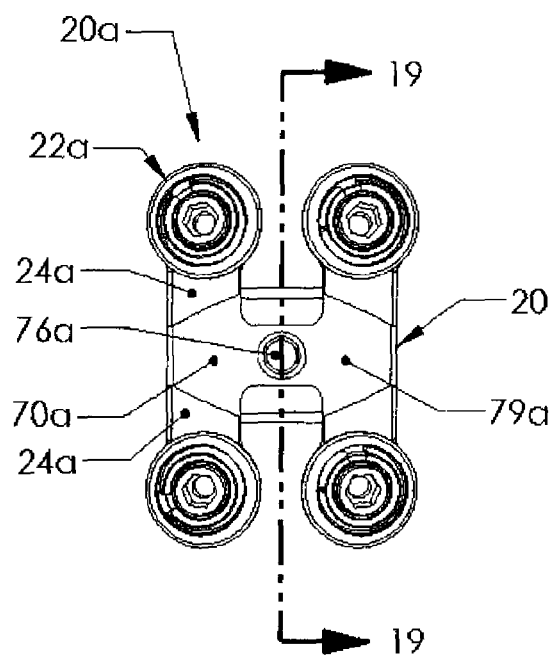
Fig. 4
Fig. 3

SPINAL FIXATION DEVICE

BACKGROUND

The present invention relates to locking fixation assemblies used in bone fixation.

Neurological and orthopedic surgeons performing spine surgery use fixation plates to treat spinal disorders including spinal anomalies, spinal injuries, disc problems and bone problems to effect fusion of vertebrae. These fixation plates are typically held by one or more screws passing through the plate and into the vertebrae above and below the injured or replaced disc. During installation of the fixation plate, the screws must be allowed to be positioned by the surgeon to provide best fitted conformity to enhance fusion rates. Misalignment can lead to fracture of the screws or wear-inducted loosening in the fixation plate assembly. There is thus a need for an easily installed fixation plate that accommodates variable angles between the fixation screws and the fixation plate.

Many of the current fixation plates are rigid. An unduly stiff plate can result in undue wear between the screws and plates which can in extreme cases lead to fracture of the screws or wear-induced flexibility in the fixation assembly. Further, some limited amount of flexibility conforms to the normal modulus of elasticity and allows impact forces to be more readily accommodated and thereby enhances fusion rate. There is thus a need for a fixation plate that can better handle sudden forces without damaging the fixation assembly or the vertebrae fastened to the fixation plate. The plate may or may not be attached to a separate cage implant.

Several current fixation plates are thick or have parts protruding from the plate, causing the overlying muscle and tissue to rub against the plate or protuberances, leading to irritation of the abutting tissue and irritation of the patient. There is thus a need for a fixation plate that reduces the irritation of the abutting and adjacent tissue.

BRIEF SUMMARY

A fixation plate is provided for tying together or fixing together two or more adjacent cervical vertebrae C2 through T1. The fixation plate can have any of three basic configurations, the first of which resembles an H shape or a series of stacked H shapes, the second of which resembles an A shape or a series of stacked A shapes, and the third of which resembles an X shape or a series of stacked X shapes. Each of the fixation plates is curved or angles about the axial plate through the two adjacent and joined vertebrae at an angle ☐ that varies with the location on the cervical column and with the number of vertebrae fixed to the plate. The angle is preferably selected to follow the average spinal curvature for the appropriate cervical location, but the angle can be varied according to an individual's specific spinal curvature, and preferably the angle is custom bent prior to use to match the spinal curvature of the patient/user. Each of the fixation plates is also curved or angled at an angle α about the sagittal plane in the anterior direction so the lateral portions of the fixation plate conform to the lateral curvature of the vertebrae and thus allow a more conforming fit of the fixation plate to the vertebrae and a lower profile plate that can fit beneath the tissue covering the anterior of the spine and thereby reduce irritation of abutting and adjacent tissue.

Each fixation plate has a socket with a curved surface configured to accommodate a bushing having a base with an outwardly extending flange. The bone screw passes through and is held by the bushing. The bushing's flange fits inside an annular recess in a socket of the fixation plate but the recess is slightly larger than the flange so the bushing can tilt until the flange hits the recess. By varying the dimensions of the flange on the bushing and the recess in the socket varying amounts of angulation or angular tilt of the bushing and bone screw can be accommodated. The annular bushing has a slot through it so it can be compressed and inserted into the socket and recess. The annular bushing is thus advantageously a split bushing.

Extending from the base of the bushing is a domed or curved wall that is segmented. A bone screw with a spherical head fits into the curved walls of the bushing with the lower portion of the spherical surface abutting a round hole in the socket and with the spherical portion of the screw head held inside the curved bushing surface to hold the screw inside the socket. The curved surface on the screw head, the inner and outer curves on the curved wall of the bushing and the curved wall of the socket all preferably have the same center of curvature.

The screw head can thus rotate inside the bushing, which rotates the socket to allow positioning adjustment of the screw relative to the fixation plate. When the plate is installed, the limited rotation allowed by the screw head, bushing and socket allow impact forces to be accommodated and provide some flexibility in absorbing the impact accompanying those forces. In particular, the split bushing can rotate, translate and distort to a limited degree in absorbing and transmitting forces from the bone screw to the fixation plate.

The fixation plate is not a solid rectangular plate but has the sockets on the ends of legs. The legs are stiff, but provide more flexibility than does the continuous plate, further providing flexibility and limited motion sufficient to accommodate impact forces. Fixation plates having an H shape, an X shape and an A shape are believed suitable.

The legs extend from the cross-members of these H and A shaped fixation plates, and from the cross member formed by the four intersecting legs of the X shaped fixation plate. The cross-member and optionally portions of the adjoining legs can be flattened on the posterior side to reduce the profile of the fixation plate and to reduce irritation of adjacent tissue. The flattening also reduces stiffness and increases flexibility. The underside, or anterior spinal sides of the cross-member and optionally the anterior side of the adjoining portion of the legs can also be flattened to further reduce the profile and/or to adjust the flexibility of the legs and the sockets at the ends of the legs. The H and X-shaped fixation plates can be joined together at common sockets to provide multi-level fixation across more than one vertebral disc space as described in detail herein.

In more detail, a spinal fixation assembly is provided that includes a bone screw having a threaded shank with a head. A driving socket is formed in the head. The head also has a continuously curved spherical outer surface continuing past a maximum diameter of the sphere. The head fits in and rotates within an annular split bushing having a plurality of segments curving away from a base and around the screw head. The curved segments have curved inner wall to rotatably receive the curved outer surface of the bone screw. The curved segments have an outer wall that is also curved. The bushing base has a hole through which the threaded shank of the screw extends but smaller than the curved screw head. The bushing also has an outward extending flange that fits into a socket in a fixation plate. The plate has at least three legs which legs extend from ends of a cross-member to form one of an H shaped, X shaped or A shaped configuration. The socket is at a distal end of each leg. Each socket has a recess curved to receive and allow rotation of the outer surface of the bushing. The socket also has an annular recess configured to receive the outward extending flange of the bushing. The annular recess is larger than the outward extending flange to allow the flange and bushing to tilt a predetermined amount depending on a thickness of the outward extending flange.

In further variations, the continuously curved spherical outer surface of the bone screw head, and the inner and outer curved surfaces of the bushing have a common center of curvature. Advantageously, the curved spherical outer surface of the bone screw ends at a top edge, and the bushing segments have flanges which resiliently extend over the top edge of the bone screw to restrain removal of the bone screw from the bushing. Further, the bone screw can have an annular recess in the head located outward of the driving socket and encircling the driving socket, to help with removal of the bone screw. Additionally, a vertebral body replacement can be optionally fastened to the fixation plate, before or after the plate is affixed to the vertebrae.

Advantageously, the fixation plate has a flattened portion on a posterior surface of the cross-member and may optionally have a flattened portion on the posterior surface of an adjoining portion of each leg. More preferably, there is a flattened portion on a posterior surface of the cross-member and a flattened portion on an anterior surface of the cross-member.

The fixation plate can have an H shape with four legs that include two superior legs and two inferior legs arranged so a first pair of the superior and inferior legs are on a left side of the fixation plate and a second pair of the superior and inferior legs on a right side of the fixation plate. The sockets on the left and right sides are each bent or inclined about an axial plane through the cross-member and also inclined in the anterior direction at an angle □ of about 6 degrees relative to a plane parallel to the coronal plane. In a further optional variation, the two superior legs and two inferior legs are each bent or inclined about a sagittal plane through a middle of the cross-member and further inclined in the anterior direction at an angle α of about 6 degrees relative to a plane parallel to the coronal plane.

The fixation plate can also have an X shape with four legs that include two superior legs and two inferior legs arranged so that a first pair of the superior and inferior legs on a left side of the fixation plate and a second pair of the superior and inferior legs on a right side of the fixation plate. The sockets on the left and right sides and the associated legs each bent or inclined about an axial plane through the cross-member and further inclined in the anterior direction at an angle of about 6 degrees relative to a plane parallel to the coronal plane. In a further optional variation, the two superior legs and two inferior legs and the associated sockets are each bent or inclined about a sagittal plane through the middle of the cross-member and are further inclined in the anterior direction at an angle of about 6 degrees relative to a plane parallel to the coronal plane.

The fixation plate can also have an A shape with three legs that include two superior legs and one inferior legs, arranged so that the superior legs and the sockets on the superior legs are each bent or inclined about an axial plane through the middle of the cross-member and further inclined in the anterior direction at an angle of about 6 degrees relative to a plane parallel to the coronal plane. The inferior leg and associated socket are also inclined in the anterior direction at an angle of about 4 degrees relative to a plane parallel to the coronal plane. In a further optional variation, the two superior legs and associated sockets are each bent or inclined about a sagittal plane and further inclined in the anterior direction at an angle of about 6 degrees relative to a plane parallel to the coronal plane.

There is also provided spinal fixation bone screw having a threaded shank. The screw head has a driving socket therein. The head extends from the shank in a continuously curved spherical outer surface that continues past a maximum diameter of the sphere. The curved spherical outer surface ends at a top edge orthogonal to the shank. In further variations, there is an annular recess in the head located outward of and encircling the driving socket. Moreover, a wrenching surface is optionally located radially inward of the annular recess, with the wrenching surface extending along an axis of the shaft to extend beyond the top edge.

There spinal fixation plate is also provided for use with an annular bushing having base with an outward extending flange and a curved wall extending therefrom toward a longitudinal axis through the bushing. The plate includes a first fixation plate having at least three legs which legs extend from ends of a cross-member to form one of an H shaped, X shaped or A shaped configuration. A socket is at a distal end of each leg. Each socket has a recess therein with an inward facing surface that is curved to receive and allow rotation of the outer surface of the bushing. The socket has an annular recess configured to receive the outward extending flange of the bushing. The annular recess is larger than the outward extending flange to allow the flange and bushing to tilt a predetermined amount depending on a thickness of the outward extending flange. The flange has a hole through which a bone screw can pass but through which the bushing does not pass.

In further variations, the spinal fixation plate has a hole in the cross-member through which a screw can pass suitable for fastening a vertebral body replacement to the fixation plate. The plate optionally has a flattened portion on a posterior surface of the cross-member and a portion of each leg. Moreover, a flattened portion can optionally be provided on an anterior surface of the cross-member.

The spinal fixation plate optionally has an H shape with four legs that include two superior legs and two inferior legs, with a first pair of the superior and inferior legs on a left side of the fixation plate and a second pair of the superior and inferior legs on a right side of the fixation plate. The sockets on the left and right sides are each bent or inclined about an axial plane through the cross-member and bent or inclined in the anterior direction at an angle of about 6 degrees relative to a plane parallel to the coronal plane. Optionally, the two superior legs and two inferior legs are each bent or inclined about a sagittal plane through a middle of the cross-member and bent or inclined in the anterior direction at an angle of about 6 degrees relative to a plane parallel to the coronal plane.

The spinal fixation plate can also have an X shape with four legs that include two superior legs and two inferior legs, with a first pair of the superior and inferior legs on a left side of the fixation plate and a second pair of the superior and inferior legs on a right side of the fixation plate. The sockets on the left and right sides and the associated legs are each bent or inclined about an axial plane through the cross-member and bent or inclined in the anterior direction at an angle of about 6 degrees relative to a plane parallel to the coronal plane. Further, the two superior legs and two inferior legs and the associated sockets may each be bent or inclined about a sagittal plane through the middle of the cross-member and bent or inclined in the anterior direction at an angle of about 6 degrees relative to a plane parallel to the coronal plane.

The spinal fixation plate advantageously has an A shape with three legs that include two superior legs and one inferior legs, with the superior legs and the sockets on the superior legs each being bent about an axial plane through the middle of the cross-member. The legs may be bent or inclined in the anterior direction at an angle of about 6 degrees relative to a plane parallel to the coronal plane. The inferior leg and associated socket are bent or inclined in the anterior direction at an angle of about 4 degrees relative to a plane parallel to the coronal plane. The two superior legs and associated sockets may each optionally be bent or inclined about a sagittal plane and bent or inclined in the anterior direction at an angle of about 6 degrees relative to a plane parallel to the coronal plane.

In the above spinal fixation assemblies, the legs may have a thickness that is smaller at the cross-member and larger at the socket. Further, for the X and H shaped fixation plates, the assembly may include a plurality of integrally formed fixation plates having the same construction as the first X or H shaped fixation plate with each plate having at least two superior sockets or two inferior sockets in common with the adjacent plate. Moreover, the sockets on the inferior legs of the first X or H shaped fixation plate form the superior sockets on a second flattened fixation plate having the same construction as the first fixation plate. Additionally, the sockets on the superior legs of the first X or H shaped fixation plate can form the inferior sockets on a third flattened fixation plate having the same construction as the first fixation plate.

There is also described herein a retention mechanism for a bone screw in a spinal fixation plate, where the fixation plate has a plurality of sockets through which a bone screw extends along a screw axis to fasten the plate to a vertebrae with at least a portion of a head of the screw located in the socket during use. The retention mechanism includes an annular bushing through which the screw passes during use. The bushing has a slot therethrough to form a split bushing. The bushing also has an outwardly extending flange and a plurality of resilient segments extending along the screw axis during use. The segments have a flange extending inward toward the screw axis during use but with the segment flanges located a distance from that screw axis. The segment flanges are sized to engage a surface of the screw which is located more than that distance from the axis during use to restrain removal of the screw along the screw axis. The socket has a recess configured to receive the flange of the bushing. The bushing is placed into the socket and the flange is placed into the recess.

In further variations of the retention mechanism the segments include an inward facing concave face with a curvature configured to mate with a curved surface of the screw head. The segments may also have an outward facing convex surface, with the curvature of the outward facing surface selected to mate with a curvature of an abutting wall of the socket. Further, the recess may be larger than a thickness of the flange to allow the flange and busing to tilt within the recess. Additionally, the head of the screw is advantageously placed inside the flanges during use, with the screw head having an annular surface orthogonal to the screw axis located to engage the latches.

The various fixation plates described herein optionally have an antibiotic coating applied to the fixation plates and also to at least portions of the components such as the screw head and bushing. Antibiotics suitable for the intended use are believed to include Ceragenin and Chlorhexidine, but other suitable antibiotics currently existing or developed in the future may be used.

BRIEF DESCRIPTION OF THE DRAWINGS

These and other features and advantages of the various embodiments disclosed herein will be better understood with respect to the following description and drawings, in which like numbers refer to like parts throughout, and in which:

FIG. 3 is a top plan view of the fixation plate assembly of FIG. 2;

FIG. 4 is a side plan view of the fixation plate assembly of FIG. 2;

FIG. 12b is a sectional view taken along 12-12 of FIG. 12a;

FIG. 13 is an enlarged sectional view of a socket taken from FIG. 12a;

FIG. 14 is a sectional view taken along 14-14 of FIG. 12a;

DETAILED DESCRIPTION

One Level H-Shaped Fixation Plate

Figure 1:
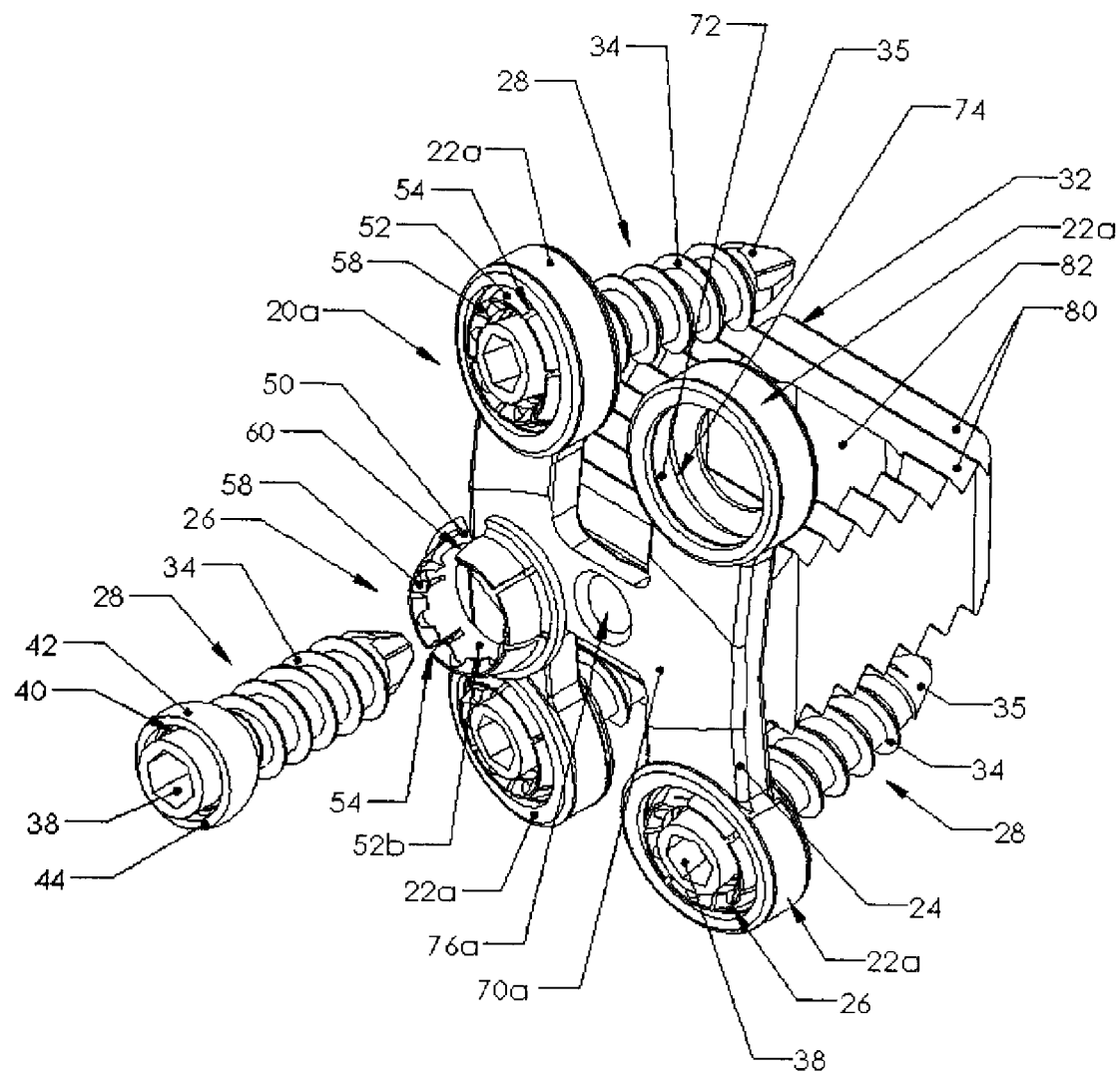
FIG. 1 is a partially exploded perspective view of a fixation plate assembly of this invention.
Figure 2:
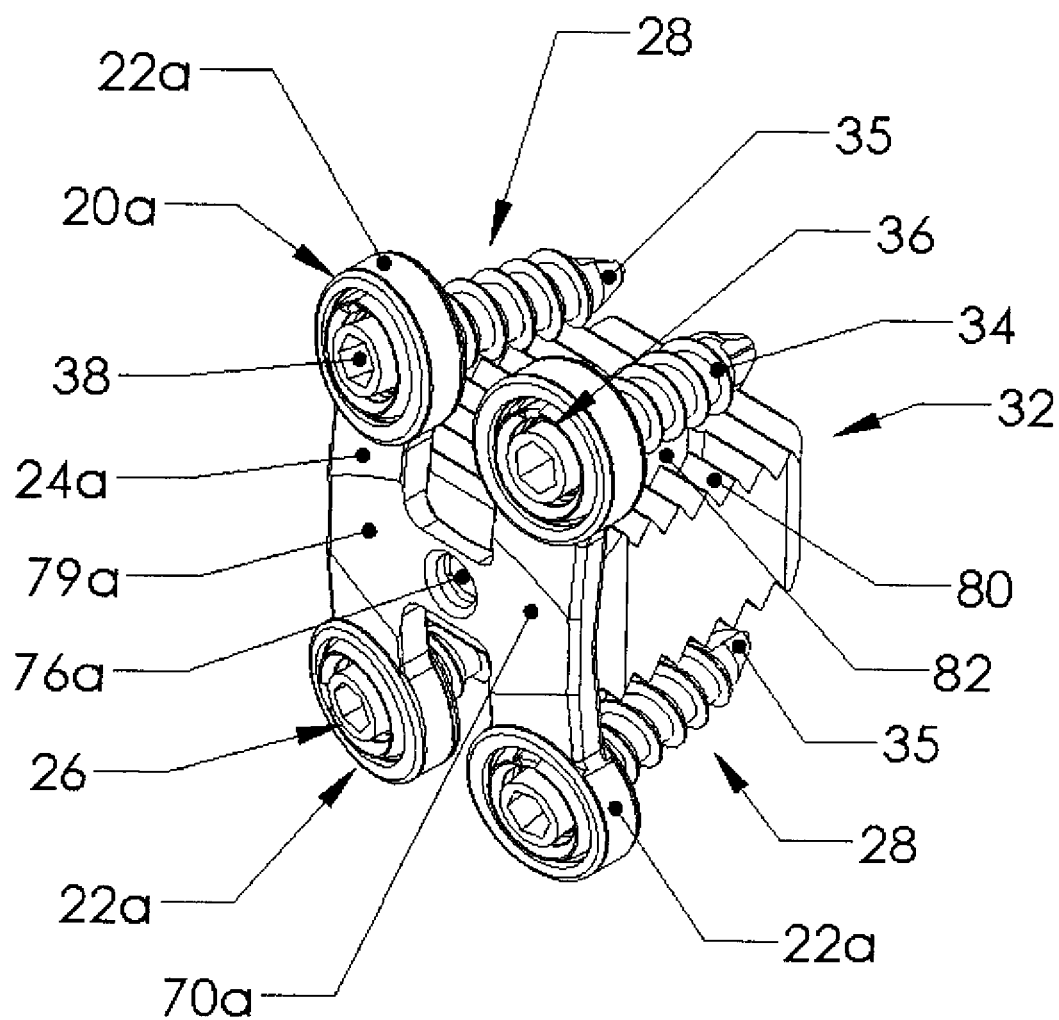
FIG. 2 is a perspective view of the fixation plate assembly of FIG. 1.

Referring to FIGS. 1-5, a bone fixation plate 20a has a generally H-shape with four sockets 22a, one at each end of the legs 24a of the H-shaped plate 20a. A bushing 26 fits within each socket 22. A bone screw 28 fits through each bushing and threads into vertebrae 30 to fasten the plate to the vertebrae 30. A vertebral body replacement 32 is fastened to the plate 20a and fits between adjacent vertebrae 30. The vertebral body replacement 32 is optional. Moreover, the fixation plate may or may not have a mount for the vertebral body replacement and may or may not have a graft attachment mount. The fixation plate 20a is believed suited for use with cervical vertebrae C2 through T1, and is believed especially suitable for C5-C6 fixation. This is referred to as a one-level fixation plate fixing two adjacent vertebrae 30 and one intervening disc.

Figure 7:
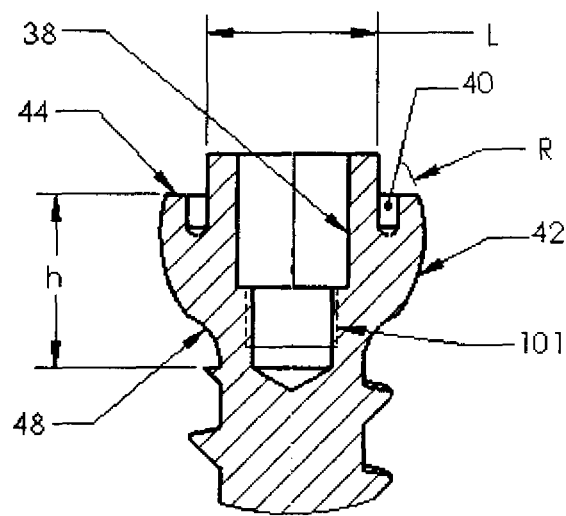
FIG. 7 is an enlarged sectional view of the head of the screw of FIG. 6.
Figure 6:
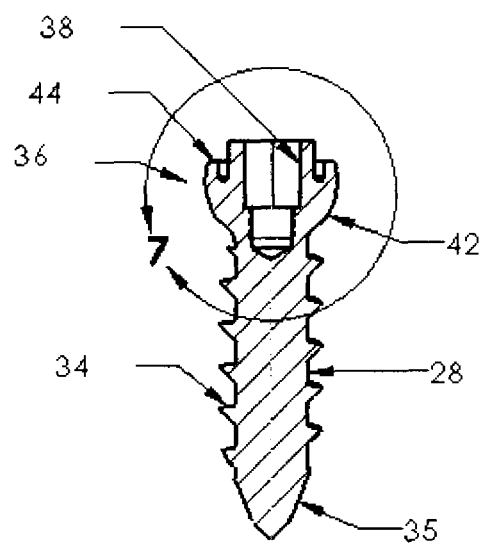
FIG. 6 is a sectional view of the screw of FIG. 1 taken along the longitudinal axis of the screw.

Referring to FIGS. 1 and 6-7, the bone screw 28 is made of stainless steel, titanium or other material of suitable strength and compatibility with implantation in the body. The screw 28 has external threads 34 suitable for use with a bone screw extending along a shank of the screw 28. The threads 34 are preferably, but optionally, self-tapping with a self taping end 35. The bones screw 28 has a head 36 with a wrenching surface 38 surrounded by an annular recess 40, and a shaped exterior bearing surface 42. The wrenching surface 38 is preferably a hexagonal socket recess extending into the head 36, but other shaped recesses can be used. An exterior wrenching surface on the outer wall surrounding the depicted socket 36 in FIGS. 6-7 could also be used, but an interior recess is preferred. The wrenching surface 38 is suitably strong for the intended use. The wrenching surface 38 is located inward of the annular recess 48 and extends along the axis of the shank of the screw 28 to extend beyond the top edge 44.

The shaped exterior bearing surface 42 is curved, and preferably spherical with the center of the sphere on a longitudinal axis of the screw 28. The shaped bearing surface 42 is preferably continuous without any interrupting slots or grooves, and is preferably continuously curved at a constant radius of curvature as with a sphere. A radius of about 0.1 inches (about 2.5 mm) is used in the depicted embodiment, but the radius can vary.

The curved bearing surface 42 is truncated by top edge 44 located in a plane orthogonal to the longitudinal axis of the screw 28 and the shank of the screw. The surface 42 is optionally slightly below the end of the wrenching surface 38 and below the end of the screw 28 at the head 36. The top edge 44 intersects the shaped bearing surface 42 at, and is preferably slightly beyond the maximum diameter of the spherical shape of that curved surface, so that the maximum diameter of the top edge 44 is slightly smaller than the maximum diameter of the shaped bearing surface 42. The shaped exterior bearing surface 42 thus forms an annular curved surface facing outward from the longitudinal axis of the screw 28, and having a first portion facing generally toward and curving toward the threads 34 and tip end 35 of the screw, and having a second portion facing generally away from and curving away from the threads 34 and tip end 35. Alternatively phrased, the shaped bearing surface 42 has a first portion curving toward the longitudinal axis of the screw 28 and curving toward the threads 34, while the second portion curves toward the longitudinal axis of the screw 28 in the opposite direction away from tip 35 and toward the head end of the screw. The oppositely facing first and second portions arise from the change in curvature of the shaped surface 42 because the annular portion of the spherical surface includes portions on opposite sides of the maximum diameter of the spherical shape which preferably forms that surface 42.

The threads 34 end adjacent the shaped exterior bearing surface 42, preferably with an annular, concave surface 48. The concave surface 48 advantageously blends the shaped bearing surface 42 to the shank of the screw 28 to reduce stress concentration at the juncture with the head 37 of the screw 28. As seen in FIG. 7, a suitable screw 28 is believed to have a head with a diameter L of the inner wall of the recess 40 being about 3.2 mm diameter, and a height H from the last thread to the top edge 44 of about 3.2 mm, and a radius of curvature R of the outer surface 42 of about head height the wrenching surface 38 and annular recess 40 of about 2.5 mm.

Referring to FIGS. 1 and 8-10, the bushing 26 has an annular shape with flat-bottomed base 50 from which extend a plurality of curved wall segments 52 separated by slots 54 with a hook or flange 56 non the ends of the segments 52 extending toward a longitudinal axis about which the bushing circles. The slots 54 advantageously extend to, but do not extend through the base 50. The flange 56 advantageously has an inclined surface 58 tapering toward the longitudinal axis through the bushing and orientated to help guide the screw 28 through the bushing 26. The wall segments 52 have inner and outer surfaces 52a, 52b, respectively. The bushing 26 is a split bushing having opening or slot 58 extending through the wall segments 52 and base 50. One segment 52 and the corresponding portion of the base 50 can be removed to form the slot 58, or a radially extending slit with parallel sides or radially extending sides can be cut in the bushing to form the slot 58. Six slots 54 are shown, with the portion of the bushing 26 between two adjacent slots being removed to form the split bushing with opening 58, leaving five slots 54 in the bushing. An entire segment 52 could be removed, or a partial segment as shown in the figures. Five to eleven slots 54 are believed suitable for use, with 5-6 slots being preferred.

Figure 8:
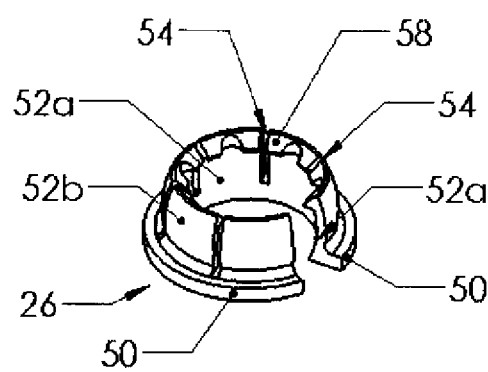
FIG. 8 is a top perspective view of the bushing of FIG. 1.
Figure 9:
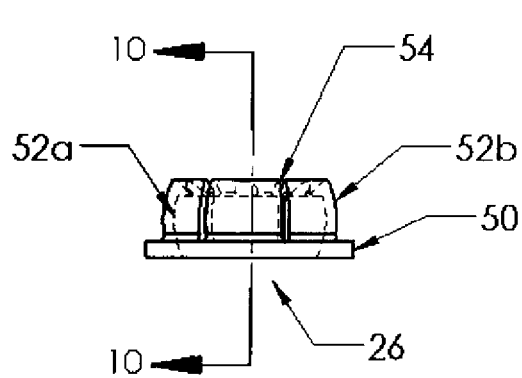
FIG. 9 is a side plan view of the bushing of FIG. 8.
Figure 10:
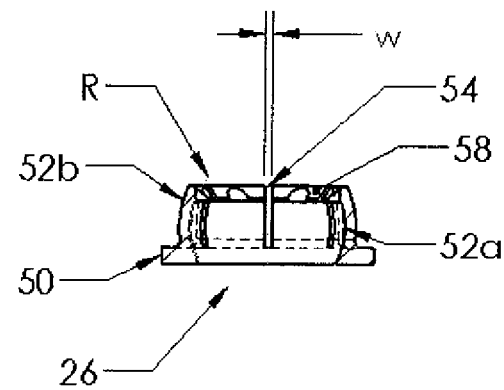
FIG. 10 is a sectional view taken along 10-10 of FIG. 9.

Referring to FIGS. 8-10, the inner and outer walls 52a, 52b are both curved, with the inner wall 52a curved to mate with the shaped exterior bearing surface 42. The inner wall 52a may have the same curvature as shaped bearing surface 42, or a slightly larger curvature so the shaped bearing surface 42 rotates easily within the inner wall 52a. The bushing 26 is made of suitably strong bio-compatible material, which material is also compatible with plate 20a and screw 28, such as titanium or stainless steel. As seen in FIG. 10, a suitable bushing 26 is believed to have segments 52 with an inner wall 52a having a radius of curvature R of about 2.5 mm and a slot width w of about 0.25 mm, with a base 50 having a thickness of about 0.5 mm.

Figure 12A:
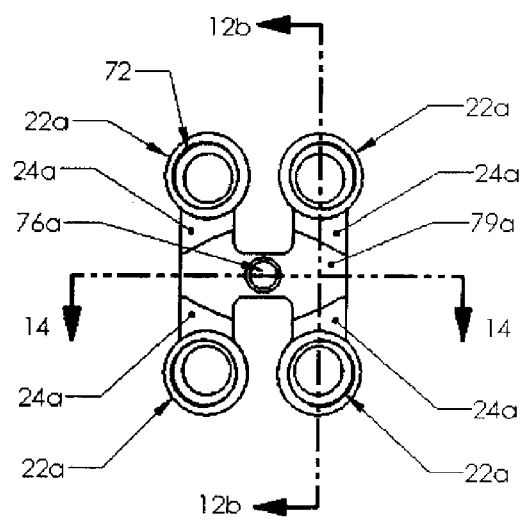
FIG. 12a is a top plan view of the H-shaped fixation plate of FIG. 1 without any parts placed in the fixation plate.
Figure 12B:
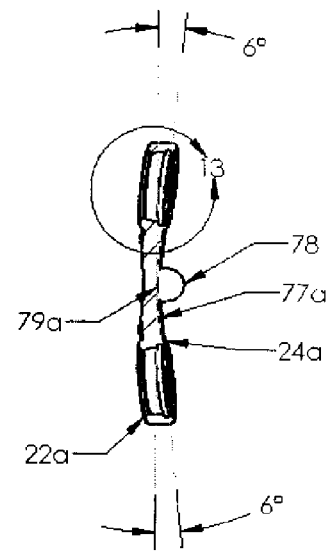
Figure 14:
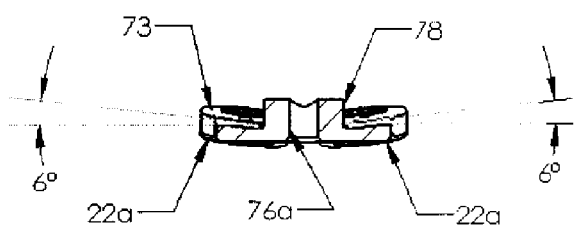
Figure 13:
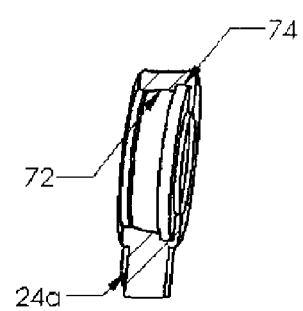
Figure 15:
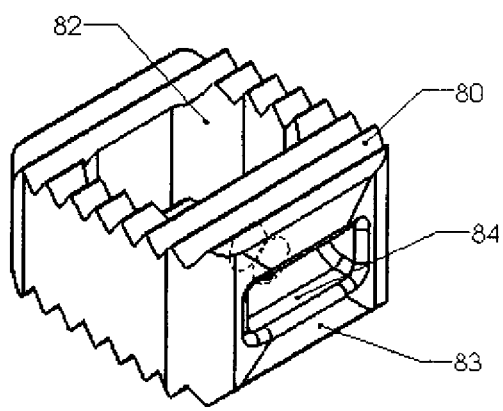
FIG. 15 is a perspective view of a vertebral body replacement as shown in FIG. 1.
Figure 16:
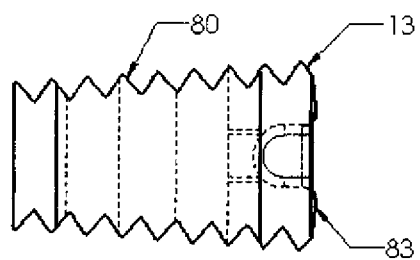
FIG. 16 is a side plan view of the vertebral body replacement of FIG. 15.
Figure 17:
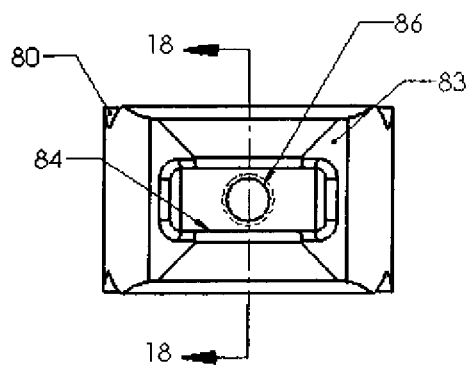
FIG. 17 is a front plan view of the vertebral body replacement of FIG. 15.
Figure 18:
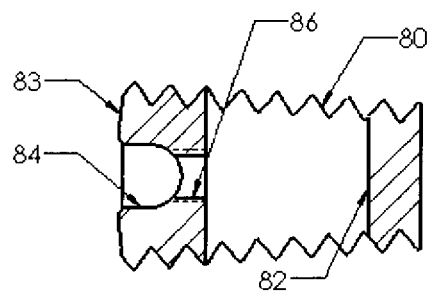
FIG. 18 is a sectional view taken along section 18-18 of FIG. 17.

Referring to FIGS. 12-14, the H-shaped fixation plate 20a has four legs 24a extending from cross-member 70 and arranged in an H configuration. A socket 22a is located at the end of each leg. During use the legs 24a extend generally along a plane parallel to the coronal plane with the cross member 70a in a lateral plane extending between the two vertebrae joined by fixation plate 20a, with the two sockets 22a on each side of the axial plane being affixed to the same vertebrae. Each socket 22a has a recess which extends through the leg 24a and has a circular wall 72 that is also curved. The wall 72 is doubly curved, and preferably forms a portion of a sphere. The curved wall 72 is shaped to mate with the curved outer wall 52b. In the preferred embodiment, the curved outer wall 52b has a curvature of about 2.85 mm and the wall 72 on socket 22a has about the same curvature or slightly larger curvature so the outer wall 52b can rotate easily against curved wall 72 in socket 22a.

The end of the socket 22a adjacent to the spine and facing toward the spine (anterior) during use has an annular recess 74 sized to receive base 50. The height of the recess 74 is slightly larger than the thickness of base 50 received within the recess. On the outside of the socket 22a and facing the spine (anterior) during use, is a pad 73 comprising a thickened portion surrounding the hole through the socket 22a to offset the legs 24a from contact with the spine. The pads 73 are shown as circular bosses, line a washer, and abut the vertebrae during use. The end of the socket 22a located away from the spine (posterior) during use may have a tapered edge to make it easier to insert the bushing 26 into the socket.

The fixation plate 20a is preferably angled or curved slightly about two perpendicular axes to better conform to the local spinal shape. Thus, two sockets 22a on opposing sides of the cross-member 70a are bent slightly in the same anterior direction so the cross-member 70a is at the apex of a slightly V-shaped plate. As used herein "bent" does not mean the part is formed straight and then bent, but instead is used to refer to a direction as in the direction in which the part is bent or is inclined. Alternately described, the sockets 22a on opposing sides of the cross-member 70a are bent or inclined relative to the axial plane extending between adjacent, joined vertebrae and extending through the cross-member 70a. The sockets 22a on the superior side of cross-member 70a are inclined slightly toward the sockets 22a on the inferior side of the cross-member and vice-versa. The sockets 22a and legs 24a are inclined at an angle □ of about 6° relative to a plane parallel to the coronal plane through the posterior of the cross-member 70a. Inclination angles from 0° to about 12° are believed usable. The inclination angle □ is selected to conform to the curvature of the cervical vertebrae. The angle can vary depending on which vertebrae are joined by the fixation plate 20a, and depending on whether an average curvature is used or on whether variations are made to accommodate an individual's specific spinal curvature. Preferably, the fixation plate 20a is made according to a predetermined curvature such as the average spinal curvature, with the plate being custom bent into a final shape that is based on X-rays of the spinal curvature of a specific user.

Two sockets 22a extend from each opposing end of cross-member 70a, and those pairs of sockets are also inclined at an angle α, with an angle of about 6° also believed suitable. The cross-member 70a bends at its middle about the sagittal plane in an anterior direction so the two sockets on each end of the cross-member 70a are anterior of the middle of the cross-member 70a This slight curvature a allows the sockets 22a to better conform to the shape of the vertebrae and provides a lower profile for the fixation plate. Thus, relative to intersecting sagittal and axial planes which advantageously intersect at the center of the cross-member 70a of each H-shaped plate 20a, each socket leg 24a and each socket 22a is inclined at an angle of about 6° relative to both the sagittal and axial planes. The center of the cross-member 70a forms an apex and that apex is preferably flattened slightly as described below to achieve a lower profile fixation plate and to allow the plate to fit below the muscle and tissue covering the posterior of the spine.

The center of the H-shaped fixation plate, at the center of the cross-member 70a (the apex), may have a hole 76a through the cross-member. A connector or mounting bracket 78a is formed on the plate 20a on the side of the cross-member 70 facing the spine during use. The hole 76 may extend through the mounting bracket 78a, as seen in FIG. 14. The shape of the connector or mounting bracket 78a will vary, and is shown as a semicircle from the side (FIG. 12) and a tube from the top (FIG. 12a).

The fixation plate 20a is believed to be suited for use with cervical vertebrae C2 through T1 and especially suitable for C5-C6. As such, the fixation plate 20a advantageously curves or angles to form a slightly concave plate facing the vertebrae to receive the vertebrae. The fixation plate 20a has a convex surface facing posterior, away from the vertebrae to reduce the height of the plate and to better conform to the vertebrae shape. Opposite the mounting bracket 78a, on the posterior side of the plate 20a facing away from the vertebrae during use, is a flattened portion 79a. The flattened portion helps lower the height profile of the fixation plate 20a. The flattened portion 79a may have a shape resembling a double headed arrow with flat tips on each arrow, and extending along the cross-member 70a, especially when used with the H-shaped fixation plate 20a where the flattened portion extends onto portions of the legs 24a adjoining the cross member 70a.

Since the legs 24a are inclined relative to the axial and saggital planes so the legs are angled toward the vertebrae in two axes, the flattened portion 79a is located at what would be the apex of the four inclined legs and reduces the height of that apex. The shape of flattened portion 79a depends on the inclination angle of the legs 24a, and in this embodiment the tips of the arrow shape are at the ends of the cross-member 70a, and the corners of the arrowhead are at the intersection of the legs 24a and the cross-member 70a near hole 76a. The flattened portion 79a is, as the name implies flat, but could also be slightly inclined toward the location of the hole 76a at which the vertebral body replacement 32 attaches to the plate 20a. A slightly curved surface could also be used and is considered encompassed within the meaning of a flattened surface.

Figure 20:
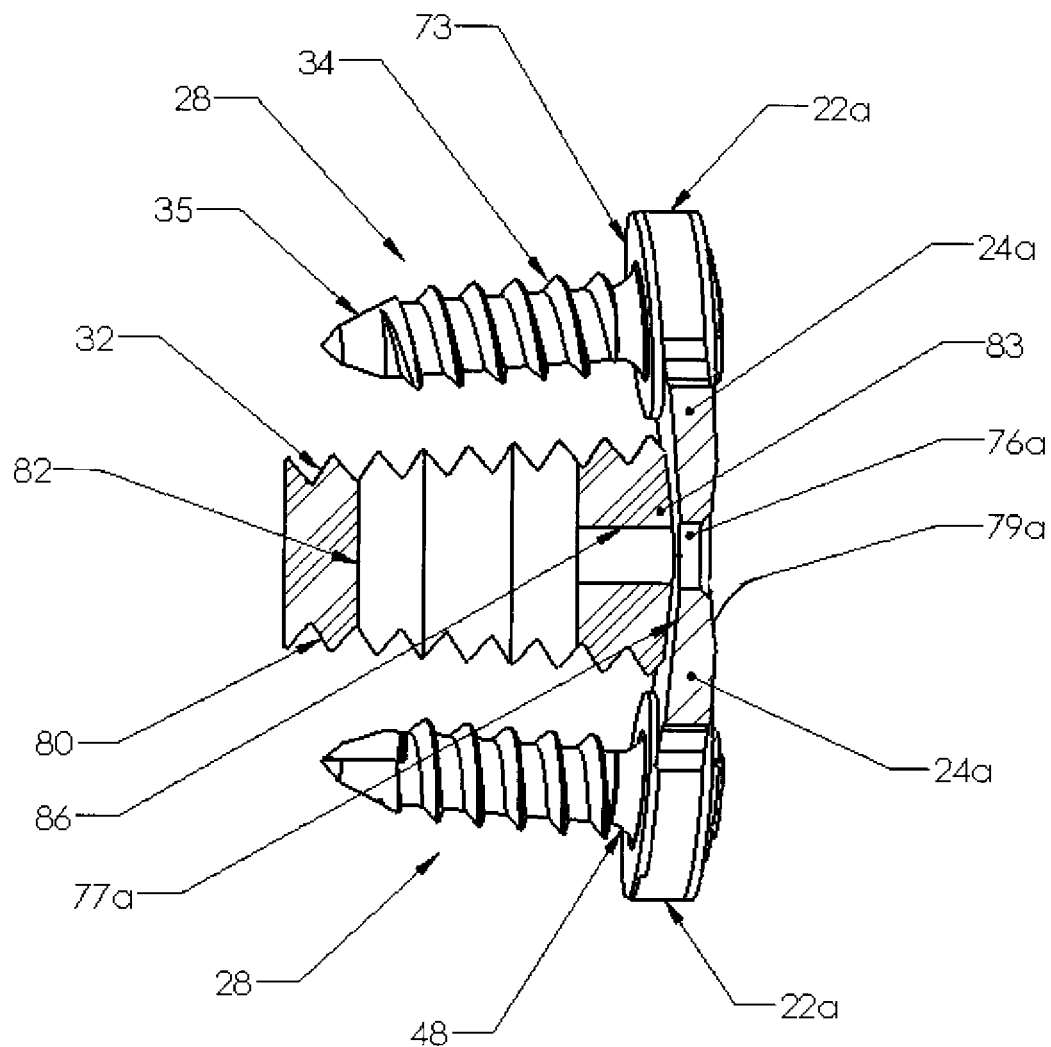
FIG. 20 is a sectional view taken along 19-19 of FIG. 3, with a mounting bracket to connect to the vertebral body replacement.
Figure 21:
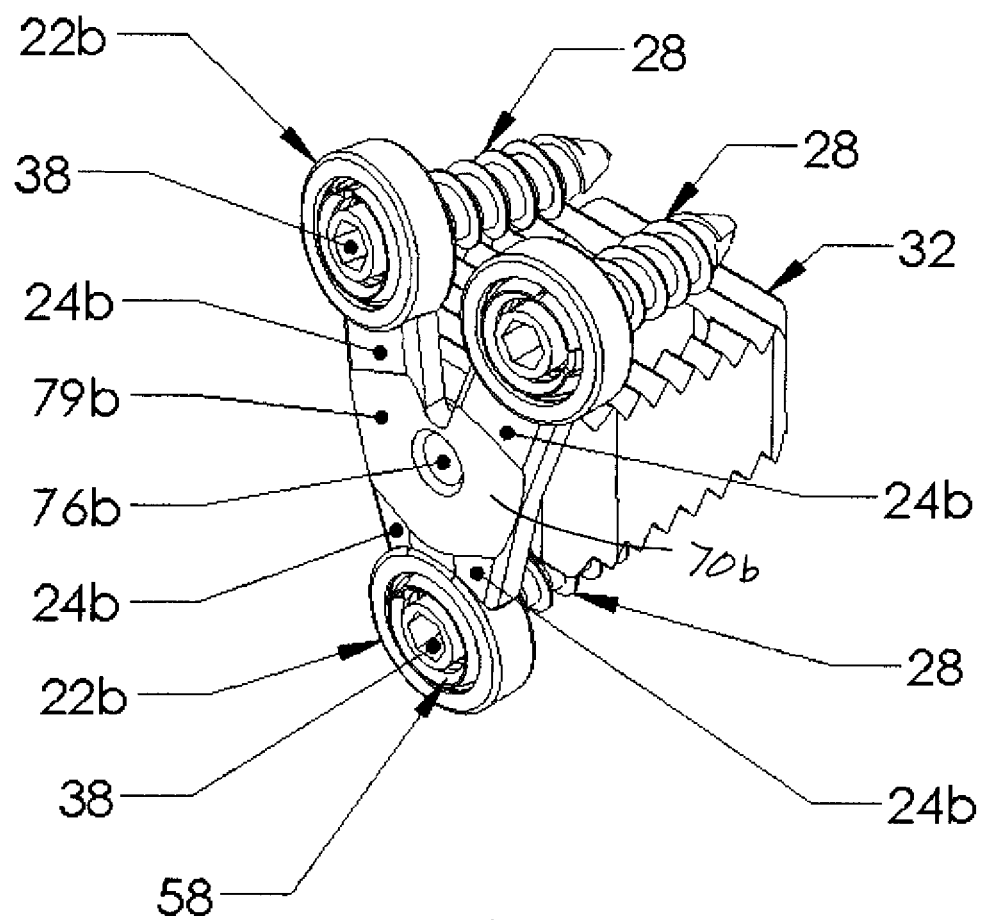
FIG. 21 is a perspective of a second embodiment of a fixation plate assembly of this invention.
Figure 22:
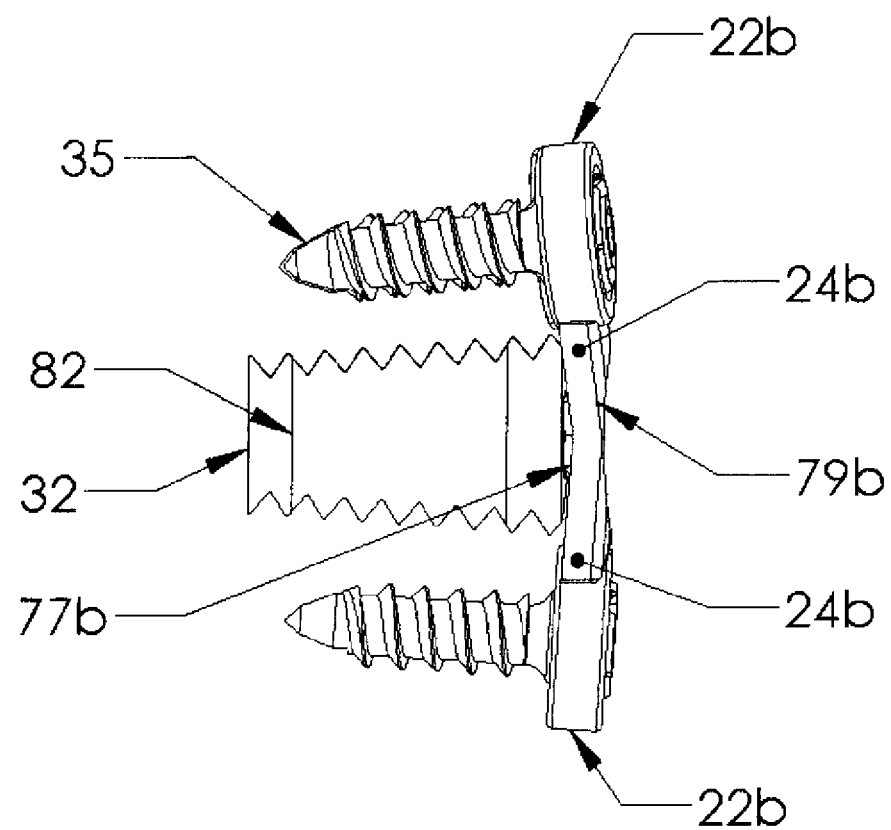
FIG. 22 is a side plan view of the fixation plate assembly of FIG. 21.
Figure 23:
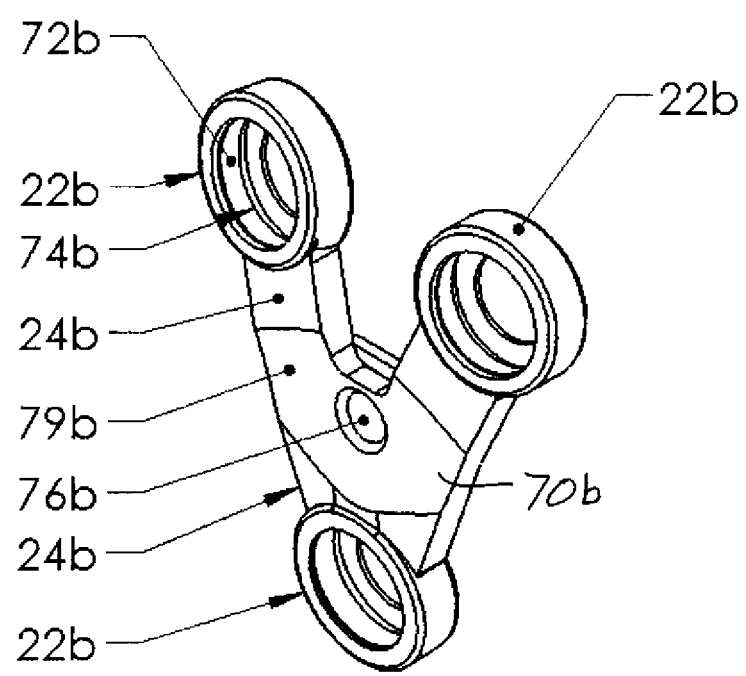
FIG. 23 is a perspective view of the fixation plate used in FIG. 21.

Referring to FIG. 20, a similar flattened portion 77a is formed on the opposing anterior side of the fixation plate 20a. The flattened portion 77a is generally like the flattened portion 79a except on the opposite side of the plate 20a.

Referring to FIGS. 15-18, the vertebral body replacement 32 is shown. This part is known in the art and is inserted to replace a disc or a vertebrae and associated discs. The vertebral body replacement typically has a slightly tapered, rectangular, wedge shape with corrugations 80 on opposing surfaces of the body replacement 32 which will abut opposing vertebrae 30 during use. A central opening 82 extends through the body replacement 32. The larger end 83 of the body replacement 32 has an elongated recess 84 with a hole 86 extending from the recess to the central opening 82. The longitudinal axis of the elongated recess 84 extends along the wider face of the rectangular body replacement 32. The hole 86 may be threaded and preferably extends from the center of the recess 84. The vertebral body replacement is typically made of PEEK or other suitable material which may include bone growth factor packaged or as a unit Referring to FIG. 20, the lager end 83 is advantageously tapered away from the elongated recess 84. The taper advantageously takes the form of two straight, slanted sides angling toward opposing edges of the replacement body in a very wide, inverted V-shaped configuration. Preferably, the inclination angle on the end 83 is a few degrees. The configuration of larger end 83 complements the shape of the flattened portion 77a on the fixation plate 20a. Advantageously, the shapes of the larger end 83 and flattened portion 77a are complementary and fit together in a nesting or mating configuration. Preferably, that nesting shape comprises two nested, V-shaped surfaces where the V-shape is formed by angles of a few degrees, and advantageously the angles are slightly different so the body replacement 32 can rock slightly along a line parallel to cross-member 70a. This slight rocking allows a slight movement of the vertebrae 30 fastened to the vertebral body replacement. The amount of movement occurring before end 83 abuts one half of the flattened portion 77a will vary, but is preferably a few degrees (e.g., about 2° or less) or a fraction of a degree.

Figure 19:
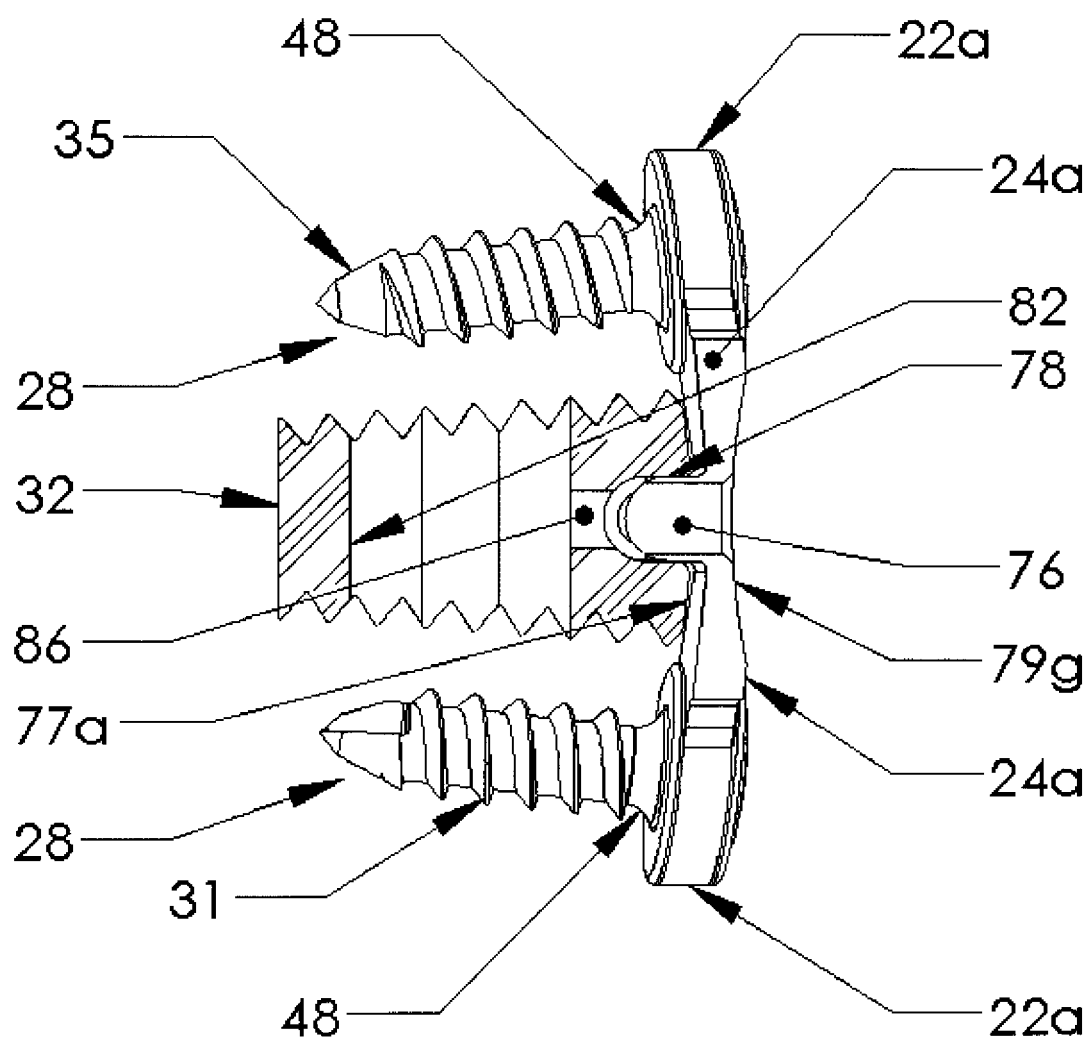
FIG. 19 is a sectional view taken along 19-19 of FIG. 3, without a mounting bracket to connect to the vertebral body replacement.

Referring to FIGS. 1 and 19-20, the vertebral body replacement 32 is fastened to the fixation plate 20a by mounting bracket 78 shown in FIG. 19 as extending into the recess 84 of the body replacement. The body replacement is shown in FIG. 20 as fastened to the fixation plate 20a without a mounting bracket in FIG. 20. In both embodiments, a threaded fastener (not shown) can extend through the hole 76a and into the vertebral body replacement to further secure the parts together. As desired, adhesives can be placed between the larger end 83 and the abutting portion of the fixation plate 20a to also hold the parts together Referring to FIGS. 11a-11b, a busing 26 is placed in each socket 22a and a screw 28 passed through the bushing and socket until the screw head 36 seats in the bushing. The bushing 26 is inserted by squeezing the bushing to close the slot 60 and reduce the diameter of the bushing until it passes through the smaller end of the socket opening encircled by inclined surfaces 58. The compresses bushing 26 is inserted until the base 50 enters recess 74 so the base 50 rests against the bottom of the socket 20. When the compression of the bushing 26 is released, the base 50 expands into the recess 74 and restrains the bushing from being removed from the socket. The curved wall segments 52 encircle the passage through the bushing 26 and socket 22a through which screw 28 can pass. The bushing 26 can rotate within the socket 22a and because the recess 74 is higher than the thickness of the base 50, the bushing can also tilt within the socket 22a until the base 50 hits the recess 74. Thus, the relative dimensions of the base 50 and recess 74, especially the dimension along the longitudinal axis of screw 28, affect the tilting of the bushing 26.

The head 36 abuts the inner wall 52a of the bushing and is larger than the opening through the bushing so the bushing restrains the screw. The recess 74 and base 50 are sized so the head 36 of the screw 28 cannot expand the bushing and slit 60 enough to allow the head to pass through the bushing. As the screw 28 is tightened, the bushing 26 will expand until the outer periphery of base 50 abuts the radial edges of recess 74.

As the head 36 abuts the hooks or flanges 56 on the bushing 26, the head pushes or urges the flanges 56 resiliently outward. The slots 54 allow each segment 52 to act as a leaf spring and to move as the head 36 passes. As the top edge 44 on the head 36 passes these hooks or flanges 56, the flanges are resiliently urged inward to latch over the top edge 44 and restrain the screw head 36 and the screw 28 from being removed from the socket 22a. Because the socket is angled about 6° along two separate and perpendicular planes passing through the center of the H-shaped fixation plate, the screws 28 are also inclined. Such screws are known in the art.

Figure 11A:
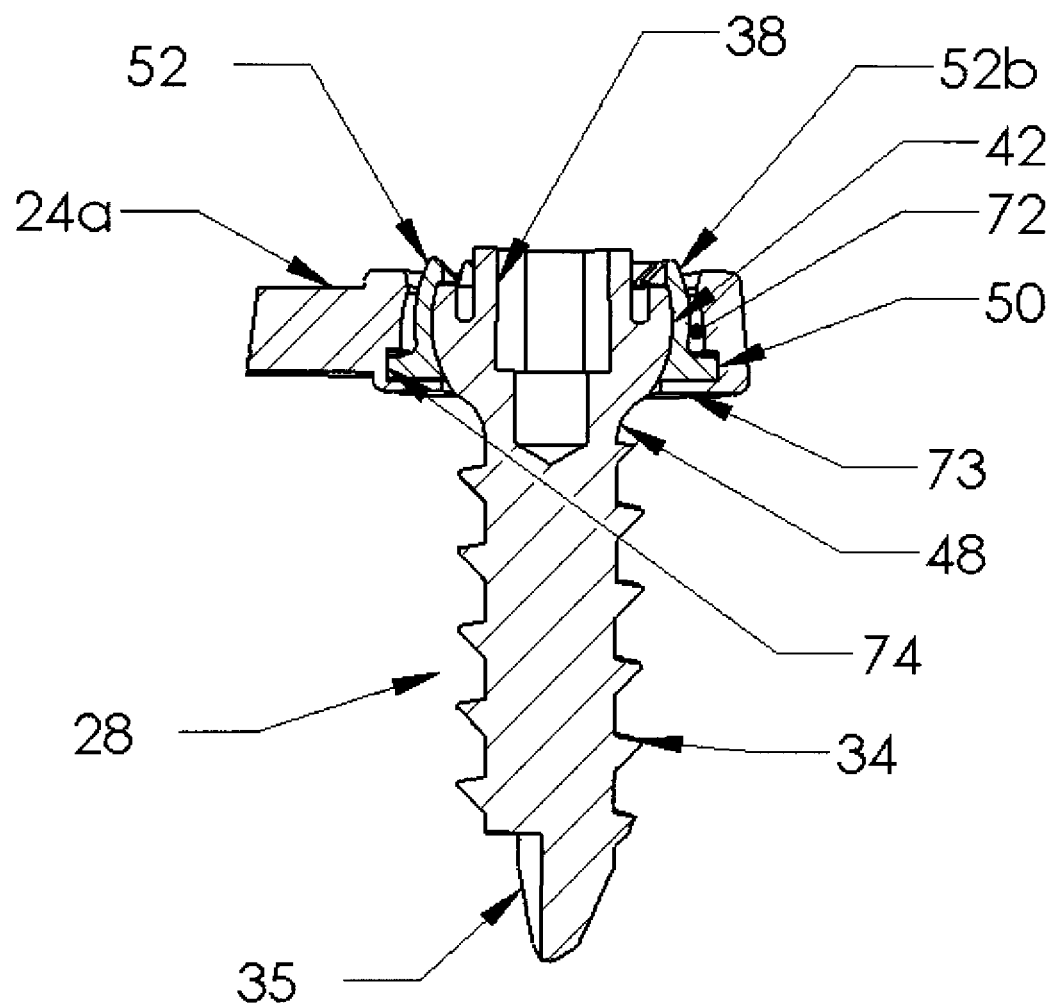
FIG. 11a is a sectional view of a screw in a bushing and socket with the screw not tilted.
Figure 11B:
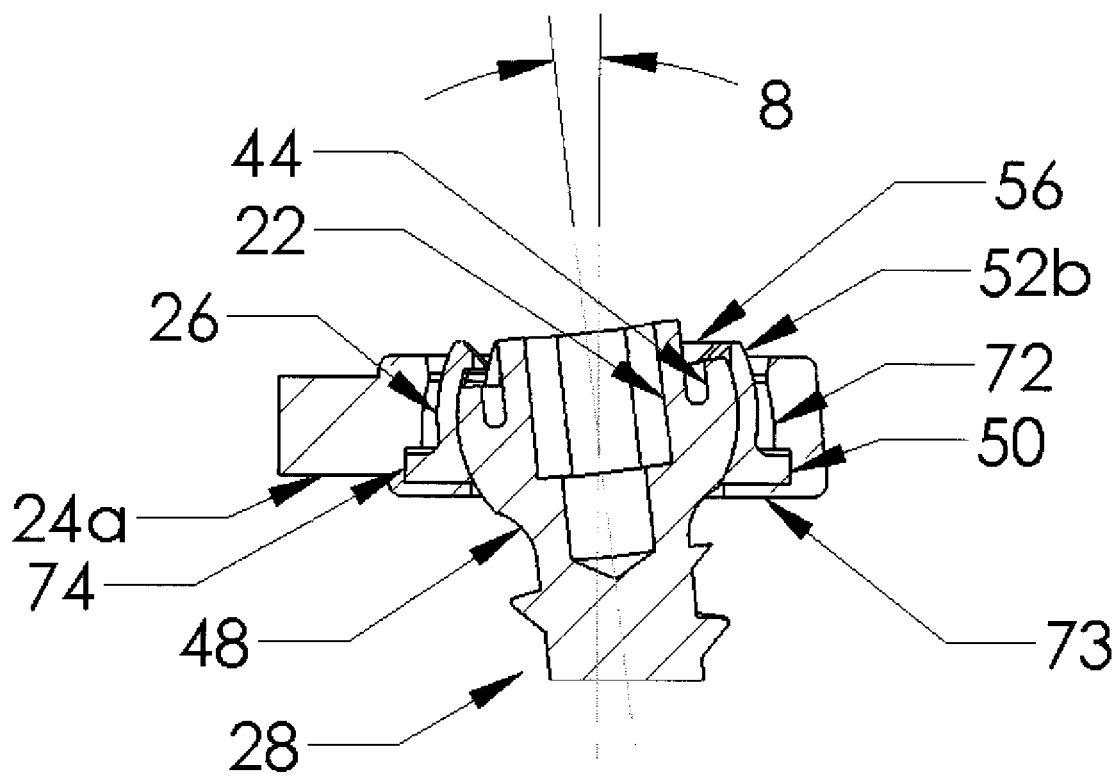
FIG. 11b is a sectional view of a screw in a bushing and socket with the screw tilted.

Still referring to FIGS. 11a-11b, the screw head 36 and bushing 26 allow the screw to rotate to any position within a cone around the longitudinal axis of the screw 28 with the half angle $\Box$ of the cone being about 6° as seen in FIG. 11b. The shaped (preferably spherical) bearing surface 42 on the screw head 36 abuts against mating (preferably spherical) inner surface 52a of the bushing 26 to allow that rotation. The amount of rotation is limited because as the screw 28 tilts the top edge 44 abuts the underside of the hooks or flanges 56 on the segments 52 of the bushing, pushing up on select segments and causing the bushing to tilt within the socket 22a. The amount of tilting is limited by base 52 abutting recess 74. Thus, the relative dimensions of the top edge 44 on head 36 relative to the hooks or flanges 56 on the segments 52 of bushing 26, affect the rotation of the screw 28 before the head 36 abuts the hooks or flanges 56 on the bushing 26. Likewise, the relative dimensions of the base 50 and recess 74, especially the dimension along the longitudinal axis of screw 28, affect the permitted tilting of the bushing 26. This rotation allows for adjustment and positioning of the fixation plate 20a and screws 28 during fastening, and allows some movement during use, both of which can be beneficial.

The bushing 26 and head 36 can also slide sideways within the socket 22a until the base 50 abuts recess 74 or until outer wall 52b of the bushing abuts the inner wall 72 of the socket. The inner wall 72 of the socket 22a is preferably curved to correspond with the curvature of the outer wall 52b to allow a surface contact and to facilitate relative rotation of the abutting parts and spreading of the forces exerted between the abutting parts.

In the event a screw 28 needs to be removed, a tool can be inserted along the ends of the hooks or flanges 56 and into the annular recess 48 in order to spread the segments 52 outward past the top edge 44 to disengage the edge 44 from the hooks or flanges 56. A wrench or tool having a bit shaped to engage wrenching surface 38 is then used to unscrew the screw 28.

Figure 5:
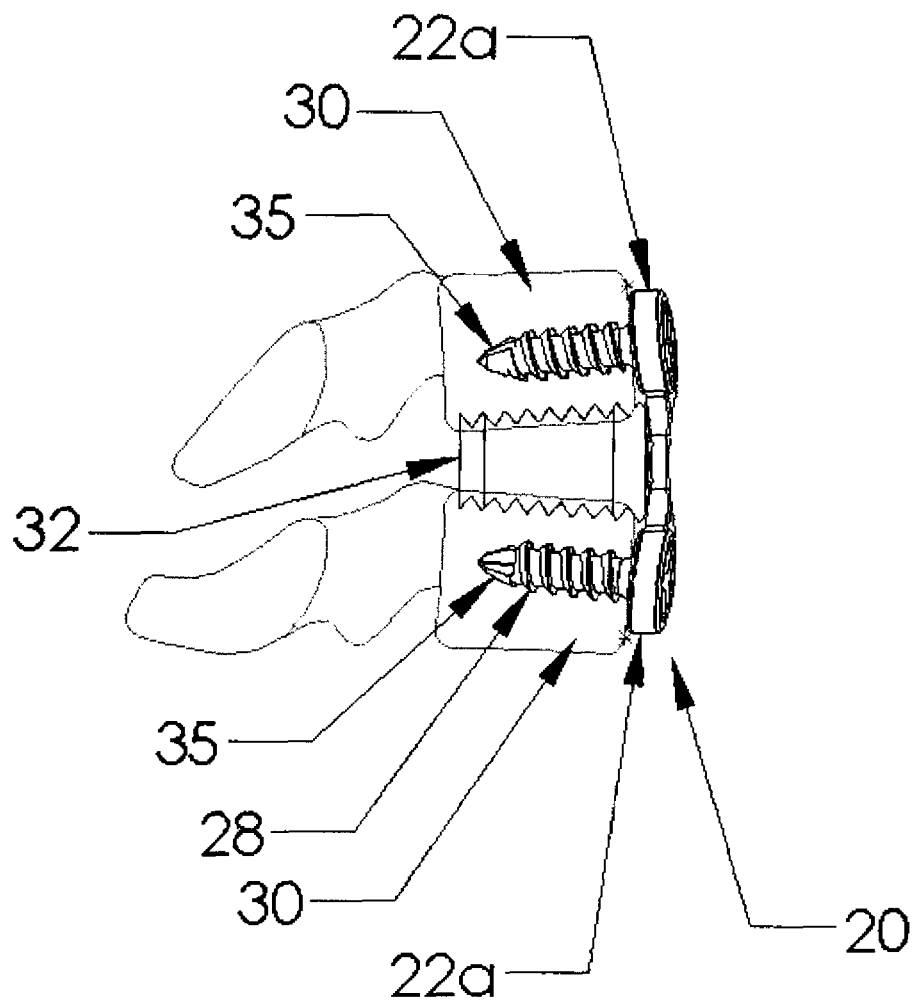
FIG. 5 is a side partial-sectional view showing the fixation plate of FIG. 2 fastened to vertebrae.

Referring to FIG. 5, during use, an intra-vertebral disc is removed between adjacent vertebrae 30. The vertebral body replacement 32 is selected to replace the disc and is either inserted between the vertebrae 30 and then fastened to the fixation plate 20a, or fastened to the plate 20a and then inserted between vertebrae 30. The bushings 26 are pre-inserted into the fixation plate 20a and the plate is placed in position on the spine so that two sockets 22a overlap each vertebrae. If the bone screws 28 are not self tapping, a hole is drilled though a socket 22a, the hole is threaded and the screw is then threaded through the socket into the drilled hole. The process is repeated for the other sockets and screws, with any of various tightening sequences being used to seat the screws and affix the plate 20a to the vertebrae 30. If the screws 28 are self-tapping a pilot hole can be pre-drilled and the screws inserted through the bushings and screwed into place. The installation tool for the screws 28 has a wrenching surface configured to engage the wrenching surface 38 on the screw 28, and in the depicted embodiment has a hexagonal shape fitting into the hexagonal socket 38 in the head 36 of the screw.

As each screw 28 is seated the flanges or hooks 56 spread apart to allow passage of the screw head 38 which is larger than the opening defined by the flanges or hooks 56, with the flanges or hooks 56 resiliently urged over the top edge 44 to restrain the screw from being removed. Advantageously the parts are sized so that the hooks or flanges 56 remain abutting the top edge 44 after the screws 28 are installed. The bushing 26 and shaped bearing surface 42 allow the screw 28 to be inclined during installation, thereby making installation easier and accommodating misalignments. As the screw 28 inclines the upper edge 44 abuts flanges 56 which rotate the bushing 26 to allow motion, with abutment of base 50 and recess 74 limiting the motion. During maximum inclination of the screw 28 it is believed that 2-3 of the segments 52 will abut the top edge 44 of the screw 28. The number of engaged segments 52 will vary with the number of segments, which can vary as discussed herein. This same installation procedure or slight variations thereof can be used for the various embodiments of the fixation plate disclosed herein.

Advantageously, the curved surfaces 42, 52a, 52b and 72 all have the same center of curvature, and are preferably all spherical, so the parts rotate easily without displacement. The large area of shaped bearing surface 42 on head 36 and inner surface 52a on bushing 26 is also believed to provide for good load distribution and avoids localized contact as in the prior art. The legs 24a and cross-member 70a are sized to allow a desired stiffness in the X and Y axes parallel to and perpendicular to the legs 24, and also in the orthogonal plane toward and away from vertebrae 30, but the legs 24a also allow some flexibility compared to a solid rectangular plate. The legs 24a are slightly angled to allow the fixation plate 20a to fit closer to the vertebrae and to conform to the local shape of the spine. The legs 24a are thin, preferably under 2 mm. Advantageously, the fixation plate 20a does not extend more than about 2 mm above the adjacent vertebrae 30 at the middle adjacent hole 76a. Because the legs 24a are inclined about the saggital and axial planes, the legs and socket 22a can be slightly thicker. The end 83 of vertebral replacement body 32 is shaped to mate with the flattened portion 77a on the underside of fixation plate 20a, and the end 83 and portion 77a preferably allow a slight rocking motion of the plate 20a and body 32 along an axis parallel to cross member 70, to allow a slight amount of flexibility in the assembly. As one side of the end 83 abuts the flattened portion 77a the motion will be limited.

If removal of a screw 28 is required, the segments 52 are pulled back and a tool is inserted into recess 40 which can have a wrenching surface for the removal tool, or which alternatively can act as a holding socket for the tool to keep the segments 52 from restraining removal of the screw while a removal tool engages the wrenching surface 38 on the screw for removal.

Referring to FIGS. 1, 6, and 65-67, the installation and removal tool is described in more detail. The installation tool 90 comprises a shaft 91 that is typically cylindrical, with a wrenching surface 92 on the end of the shaft. The wrenching surface 92 is configured to engage the wrenching surface 38 in screw 28. A hand driven tool or powered driving tool such as an electric drill (not shown) is used to rotate the shaft and drive the engaged screw 28 into a seated position in the bushing 236 and its socket in the fixation plate until the hooks or flanges 56 engage the top edge 44 of the screw. The installation tool 90 fits within the space surrounded by the hooks or flanges 56.

For removal, the flanges 56 on the segments 52 need to be disengaged from the edge 44 of the screw 28 so the screw can be withdrawn from the socket 22a, bushing 26 and fixation plate. A tubular guide 93 is provided that is coaxial with the shaft 91 of the installation tool 90 and wrenching surface 92. The inner wall of the tubular guide 93 is sized to snugly fit over the shaft 91 of tool 90 so the installation tool 90 fits inside and is guided by the inner wall of the tubular guide 93. The guide 93 has a tubular end 94 configured to fit into and engage the recess 40 in the screw 28 to align the longitudinal axis of the screw 28 with the axis of the guide 93 and tool 90. The depth of recess 40 is sufficient to align the guide 93 with the axis of the screw 28, but the guide end 94 is preferably longer than the recess 40 is deep for reasons discussed later.

The tubular guide end 94 is smaller in diameter than the adjacent portion of the guide 93 so there is an inwardly tapered portion 95 joining the main body of the guide 93 with the guide end 94. A taper of about 20° from the longitudinal axis of the tool 90 and guide 93 is believed suitable, but the angle can vary. The radial thickness of the recess 40 is small in order to allow a smaller head on the screw 28. The small dimension would make for a thin guide 93 and it is desirable for strength and stability to have a thicker guide 93 so the taper allows a thicker wall on the guide 93.

A spreader 96 is coaxially located with the guide 93 and radially outward of the guide so the guide 93 separates the installation tool 90 and the spreader 96. The spreader 96 is tubular with an inner diameter sized to allow it to snugly fit over the guide 93 and slide along a length of the guide. The end 98 of the spreader 96 adjacent the screw 28 during use is shaped. The inside diameter of the spreader 96 at the end 97 tapers inward toward the longitudinal axis of the spreader at an angle corresponding to the taper 95 on the guide 93. The mating taper on end 97 engages the taper 95 on the guide 93 to prevent the spreader 96 from moving along the guide 93 in a direction away from the screw 28 during use. Those tapers also require the spreader 96 to be slid over the end 94 of the guide 93 to fit the spreader 96 over the guide 93.

The outer surface 98 of the end 97 is also shaped to engage the inclined surfaces 58 on the segments 52 of the bushing 26 and move those segments outward, away from the longitudinal axis of the screw 28 and away from engagement with the annular top edge 44 of the screw. Basically, the spreader end 97 slides along the guide 93 which is inside the inclined surfaces 58 of the bushing 26. The spreader end 97 is forced toward the screw 28 and the inclined outer spreader surface 98 is forced between the guide end 94 and the inclined flanges 58, causing the flanges 58 and their associated segments 52 to open and disengage from the edge 44 of screw 28. The edge 99 of the spreader end 97 is the edge between the inclined inner and outer walls of the spreader end 97, and that edge 99 is preferably the same size as or slightly greater than the annular edge 44 on the screw in order to ensure the flanges 56 disengage from the screw. In short, the distal edge 99 on the end 97 of spreader 96 is forced between the guide end 94 and the flanges 56 to move the flanges out of engagement with the edge 44 of the screw 28. The edge 99 is preferably wider than the edge 44 of the screw engaged by the flanges 56 so the flanges are disengaged from the edge 44.

Advantageously, the outer spreading surface 98 is inclined at an angle that corresponds with the angle of inclination of the inclined surfaces 58. An angle of about 45° or slightly less, measured from the longitudinal axis of the screw 28, is believed suitable. But the angles will vary depending on the inclination of the inclined surface 58 and the shape of the inclined surfaces 58 and the hooks/flanges 56. To allow the end 97 of the spreader to fit more easily between the inclined surfaces 58 of flanges 56, the end 97 is slotted by slots 100 to form a plurality of segments that can move radially inward toward the longitudinal axis of the screw 28. The guide end 94 prevents the spreader end 97 from moving inward too much and thus limits the inward movement of the spreader end 97, ensuring the flanges 56 will be spread outward a predetermined distance sufficient to disengage the flanges 56 from the screw 28.

Once the end 97 is inserted between the flanges 56 and guide end 94 to disengage the flanges 56 from the screw edge 44, the screw 28 can be removed. The wrench surfaces 92, 38 are rotated by shaft 91 to remove the screw 28 through the inside of the guide 93, or once the flanges 56 are disengaged other removal tools can be used. The shaft 20, guide 93 and spreader 26 are advantageously made of suitably strong material, preferably a high strength stainless steel. Advantageously, the bottom 101 of the recess forming wrenching surfaces 38 is tapped with left handed screw threads so that if the wrenching surface 38 is stripped, a redundant mechanism is provided for engagement and removal of the screw 28 by screwing a normal right hand threaded screw or bolt into the bottom of the recess surrounded by wrenching surface 38.

One Level A-Shaped Fixation Plate

Referring to FIGS. 21-28, a further embodiment is shown having four legs 24b arranged in an A configuration. Most of the parts are the same as described above and that description is not repeated, but the corresponding parts are labeled with a "b." The screws 28, bushings 26 and vertebral body replacement 32 retain their original numbers without a "c" suffix since these parts are unchanged by configurational changes of the fixation plate. Two legs 24b form the base of the A configuration, with a socket 22b at the end of each leg. The two legs 24b are aligned along two axes that intersect at the apex of the A at an angle of about 50° from each other or about 25° from the plane through the vertebrae and along the spine. The apex of the A is on the sagittal plane with each leg 24b inclined relative to a plane parallel to the coronal plane and with the apex and legs further inclined relative to the axial plane extending along the length of the cross-member of the A shaped fixation plate. The fixation plate 20b is believed suited for use with cervical vertebrae C2 through C7, and is believed especially suitable for C5-C6 fixation. This is also referred to as a one-level fixation plate fixing two adjacent vertebrae 30 and one intervening disc.

The central plate or cross-member 70a is located at the cross-member of the A configuration. A connecting bracket 78 is optionally located at hole 76 at the middle of the cross-member of the A configuration. The depicted embodiment has two legs 24b extending from the cross-member 70b to the socket 22b at the top of the A configuration. The two legs 24b may be wider at the cross-member 70b and narrower at the socket 22b, with the legs 24b preferably sized to provide about the same stiffness of a single leg 24b which has a larger width than an individual leg 24b. The dimensions of the legs 24b are preferably selected so each socket 22b has the same stiffness connecting it to the cross-member 70b. Advantageously, during use the two legs 24b extend in a superior direction with the single opposing socket 22b located in an inferior position, but the orientation can be reversed.

Figure 26:
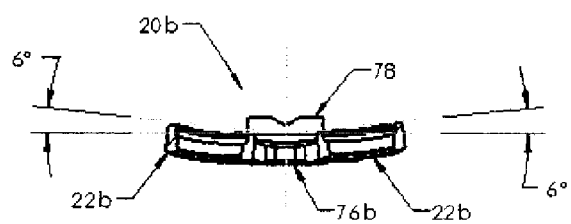
FIG. 26 is a section view of the fixation plate of FIG. 24 taken along 26-26 of FIG. 4.
Figure 27:
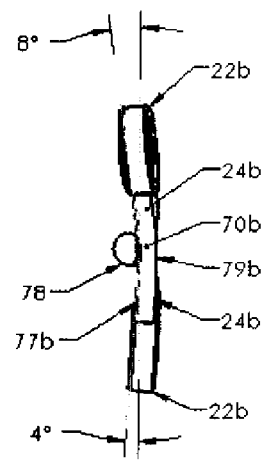
FIG. 27 is a left plan view of the fixation plate of FIG. 24, with the other side view being a mirror image thereon.
Figure 24:
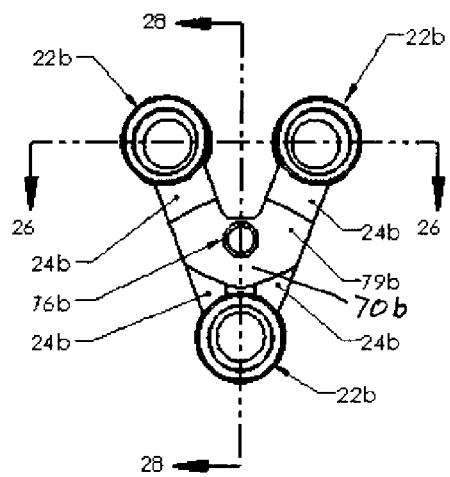
FIG. 24 is a top plan view of the fixation plate of FIG. 23.

Referring to FIG. 27, the cross-member 70b is located in the axial plane which passes between the vertebrae joined by the fixation plate 20b. The saggital plane passes through the apex of the A shaped plate 22b and through the middle of the cross-member 70b. The socket 22b at the apex of the A shaped plate 22b and the sockets 26b at the legs 24b are bent about the axial plane through the cross-member 70b so the bottom of the sockets 26b adjacent the vertebrae during use are inclined from a plane parallel to the coronal plane along the bottom of the cross-member 70b. An inclination angle □ of about 8° on the legs 24b is believed suitable for joining the C5 and C16 vertebrae as seen in FIG. 27. Preferably, the fixation plate 22b is made according to a predetermined curvature such as the average spinal curvature, with the plate being custom bent into a final shape that is based on X-rays of the spinal curvature of a specific user. The apex may be inclined at an angle of about 4° relative to a plane parallel to the coronal plane. The legs 24b are also bent at an angle $\alpha$ about the sagittal plane to better conform to the shape of the vertebrae. As seen in FIG. 26, the bottom of the two sockets 26b at the bottom of the two legs of the A are inclined at an angle $\alpha$ of about 6° relative to the a plane parallel to coronal plane while the socket 22b at the apex of the A is in the coronal plane since it fastens to the middle posterior side of the vertebrae rather than fastening toward the lateral sides of the vertebrae.

Figure 28:
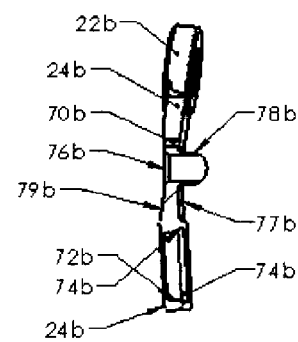
FIG. 28 is a section view taken along 28-28 of FIG. 24.
Figure 25:
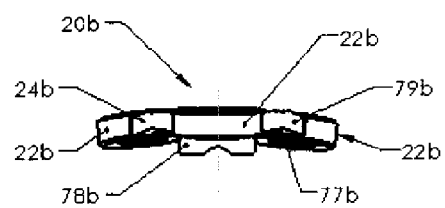
FIG. 25 is a bottom plan view of the fixation plate of FIG. 24.
Figure 29:
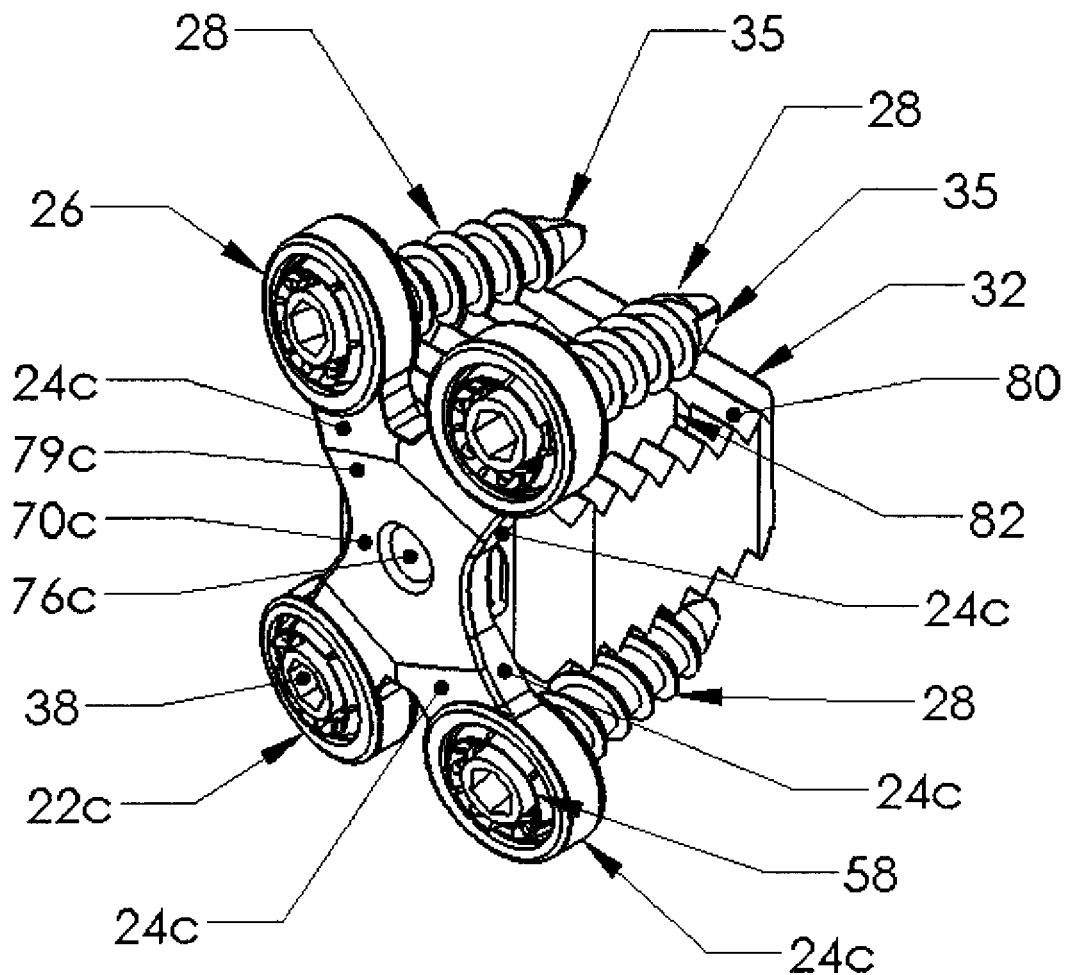
FIG. 29 is a perspective view of a further embodiment of a fixation plate assembly with an X shaped plate.
Figure 30:
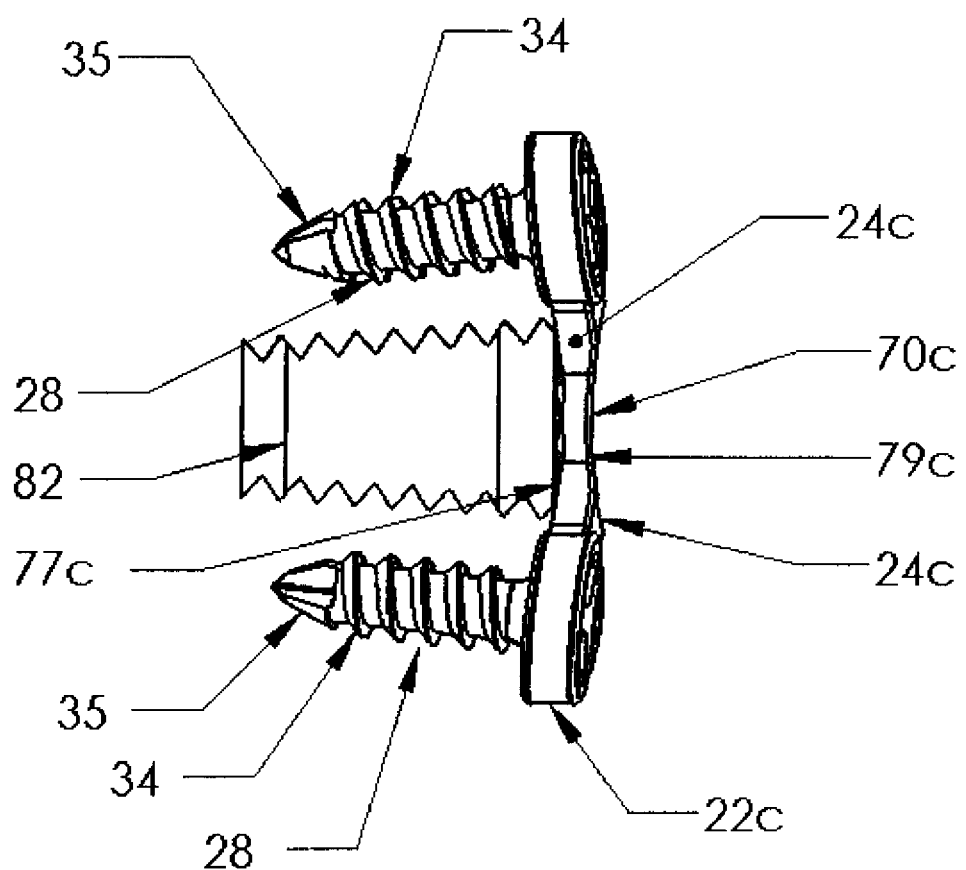
FIG. 30 is a side plan view of the fixation plate assembly of FIG. 29.
Figure 31:
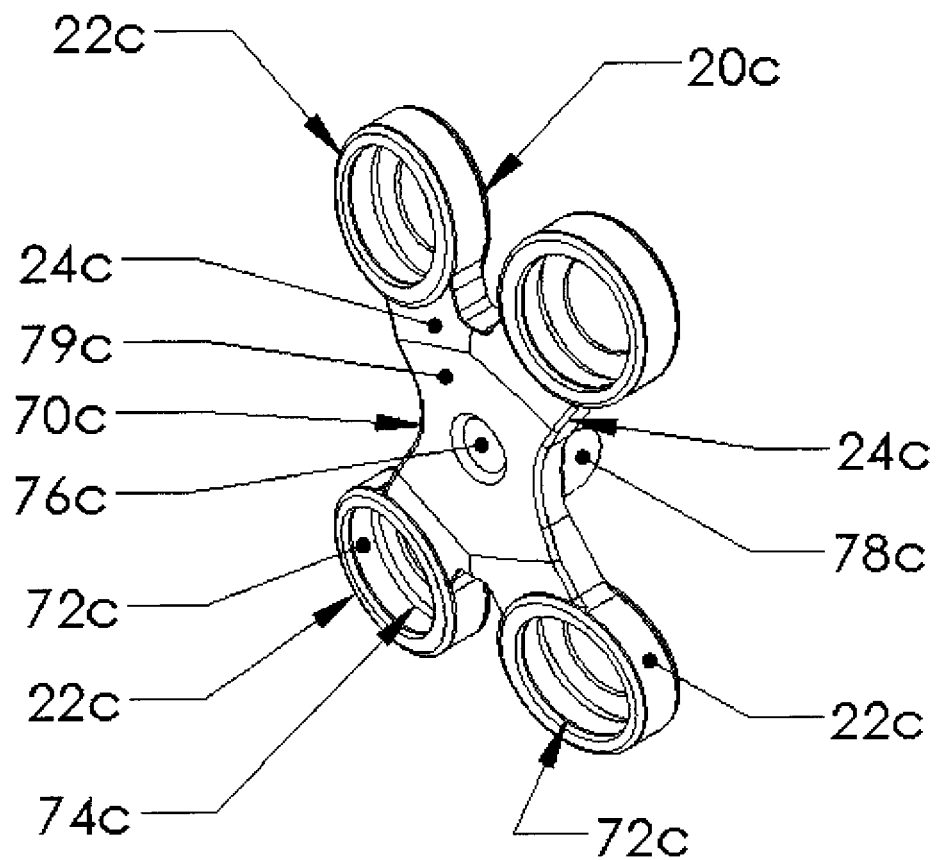
FIG. 31 is a perspective view of the X shaped fixation plate of FIG. 29.
Figure 32:
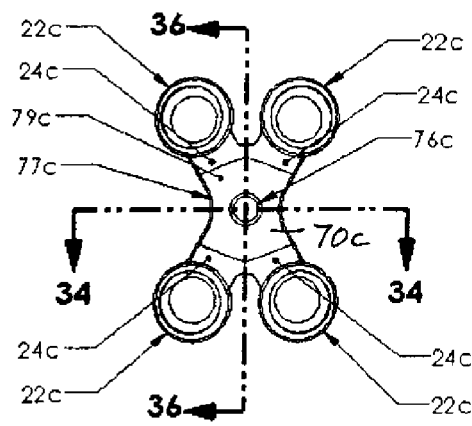
FIG. 32 is a front plan view of the fixation plate of FIG. 31.
Figure 33:
FIG. 33 is a bottom plan view of the fixation plate of FIG. 32, with the top plan view being a mirror image thereof.
Figure 34:
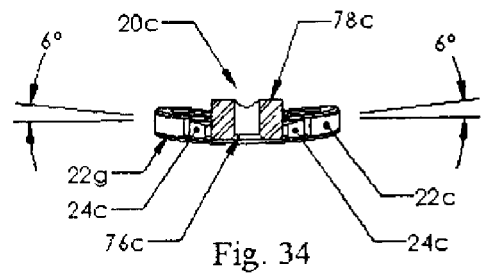
FIG. 34 is a sectional view taken along 34-34 of FIG. 32.
Figure 35:
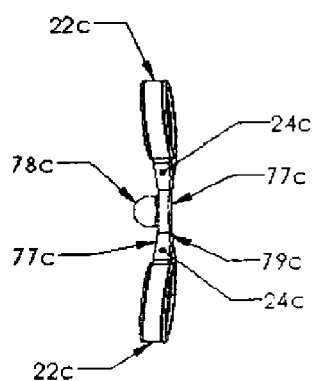
FIG. 35 is a left plan view of the fixation plate of FIG. 32, with the right plan view being a mirror image thereof.

Referring to FIG. 28, the fixation plate 20b is thinner at the middle by hole 76b and cross member 70b, and is thicker at the sockets, such as socket 20b. This is achieved by flattening the posterior portion 79b of the fixation plate 20b which faces away from the vertebrae during use, and helps reduce the height profile of the fixation plate. Because the legs 24b are angled or inclined in order to position the sockets 22b, the flattened portion 79b resembles a squat-shaped A with a broad, three sided apex at the center of the cross-member 70b, and short legs extending part way down the two legs of the A-shaped plate. The apex is flattened. As seen in FIG. 28, the legs 24b are thicker adjacent the sockets 22b and thinner at the center of the cross-member 70b at the hole 76. The flattened portion 79b is, as the name implies flat, but could also be slightly curved or otherwise inclined toward the location of the hole 76 at which the vertebral body replacement 32 attaches to the plate 20a.

Referring to FIGS. 27 and 28, a similar flattened portion 77b is formed on the opposing (anterior) side of the fixation plate 20b. The flattened portion 77b is generally like the flattened portion 79b except on the opposite (anterior) side of the plate 20b. The larger end 83 of the vertebral body replacement 32 is advantageously tapered away from the elongated recess 84 to allow a slight rocking of the replacement body 32 along a line parallel to cross member 70b, with the amount of rocking being limited by abutment with the flattened portion 77b. This slight rocking allows a slight movement of the vertebrae 30 fastened to the vertebral body replacement 32. The amount of movement occurring before end 83 abuts one half of the flattened portion 77b will vary, but is preferably a few degrees (e.g., about 2° or less) or a fraction of a degree.

The A-shaped fixation plate 20b is configured to have one socket 22b at the apex of the A fastened to the center of a vertebrae 30, with the two sockets 22b located at each end of one of the two legs of the A and located in a spaced apart relationship on a different vertebrae 30. The apex socket 22b is advantageously orientated downward toward the ground as a person is standing.

The A-shaped fixation plate 20b provides for three fixation points to the vertebrae and that three point mount is easier to analyze and does not tend to bend or distort the A-frame fixation plate 20b as do over-constrained plate mounts using more than three fixation points. The single socket 22b at the apex of the A-shaped fixation plate 20b also allows nesting the A-shaped fixation plate between the legs of other mounting plates disclosed herein as well as nesting the apex of the A-shaped plate between the two sockets at the ends of the legs of the A-shaped plate.

One Level X-Shaped Fixation Plate

Referring to FIGS. 29-36, a further embodiment is shown having a generally X-shaped fixation plate 20c with a flat portion 79c. Most of the parts are the same as described above and that description is not repeated and the corresponding parts in the drawings are labeled with the letter "c." The screws 28, bushings 26 and vertebral body replacement 32 retain their original numbers without a "c" suffix, since these parts are unchanged by configurational changes of the fixation plate. The legs 24c are aligned along two axes that intersect at an angle of about 60° from each other or about 30° from the sagittal plane through the vertebrae and along the spine, with the intersection being at the center of hole 76. The sides of the legs 24c join at rounded intersections to reduce stress and avoid tissue damage. The flattened portion 79c on the posterior side of the plate 20c resembles a plan view of a woman's corset with opposing curved sides and a top having two upwardly inclined lines intersecting and the medial plane and the bottom having two downwardly inclined lines intersecting at the medial plane. The flattened portion 79c is, as the name implies generally flat, but could also be slightly curved or otherwise inclined toward the location of the hole 76 at which the vertebral body replacement 32 attaches to the fixation plate 20c. The fixation plate 20c is believed suited for use with cervical vertebrae C2 through T1, and is believed especially suitable for C5-C6 fixation. This is also referred to as a one-level fixation plate fixing two adjacent vertebrae 30 and one intervening disc.

Figure 36:
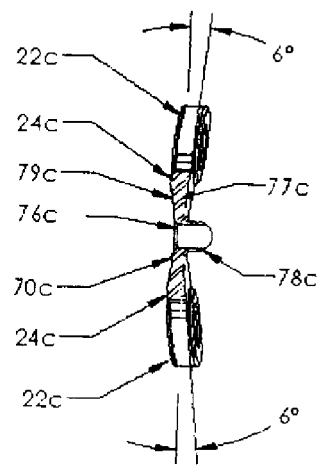
FIG. 36 is a sectional view taken along 36-36 of FIG. 32.
Figure 37:
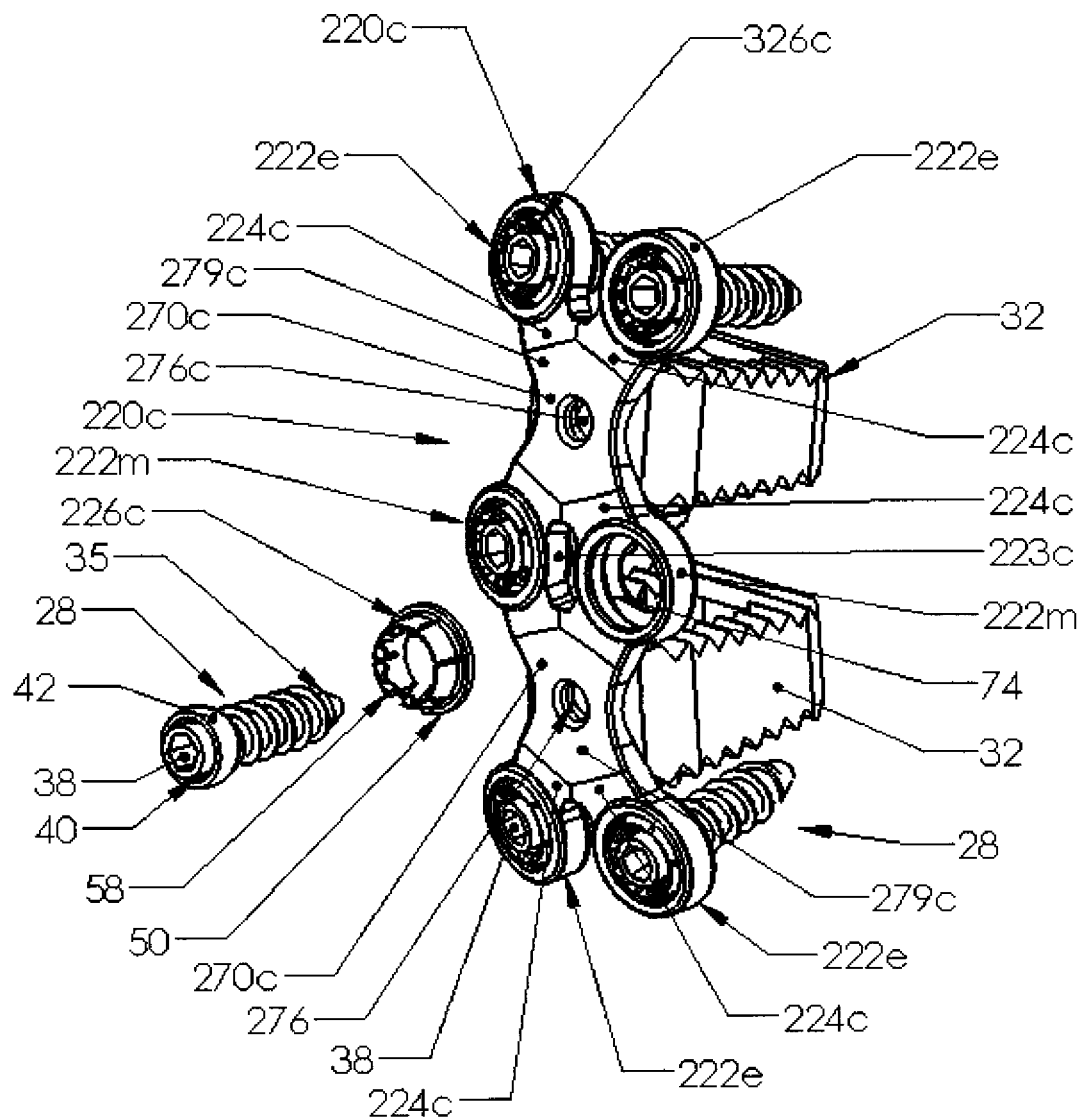
FIG. 37 is a partially exploded perspective view of a further embodiment showing a two-level X-shaped fixation plate with two vertebral body replacements.
Figure 38:
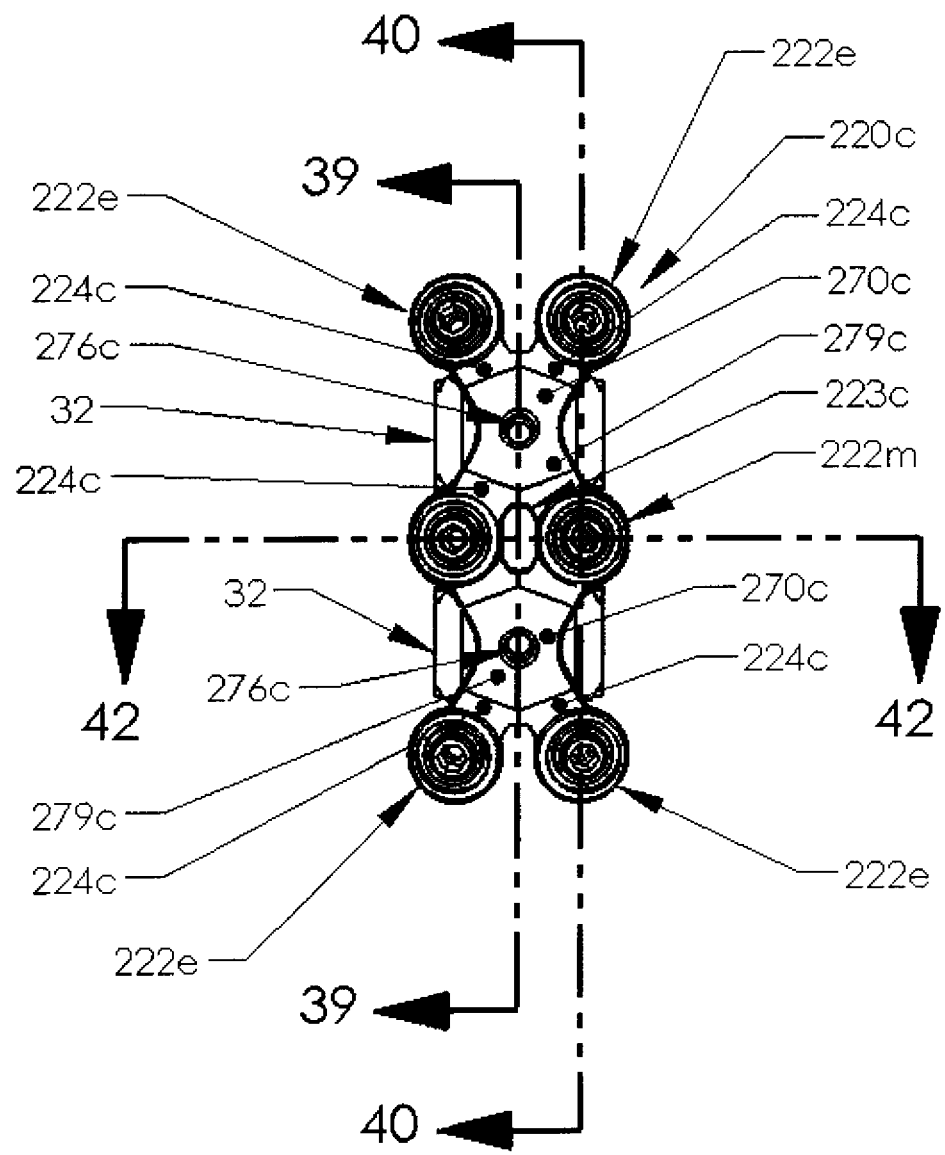
FIG. 38 is a plan front view of the fixation plate of FIG. 37.

Referring to FIG. 36, a similar flattened portion 77c is formed on the opposing (anterior) side of the fixation plate 20c. The flattened portion 77c is generally like the flattened portion 79c except on the opposite (anterior) side of the plate 20c, for the reasons discussed above regarding vertebral body replacement 32.

The sockets 22c are angled as with the H-shaped fixation plate 20a, so the legs 24c are bent or inclined about the axial plane at an angle □ of about 6° relative to a plane parallel to the coronal plane to conform to the desired curvature of the joined vertebrae and spine. Preferably, the fixation plate 20c is made according to a predetermined curvature such as the average spinal curvature, with the plate being custom bent into a final shape that is based on X-rays of the spinal curvature of a specific user. The legs 24c are also bent or inclined about the sagittal plane at an angle α of about 6° relative to a plane parallel to the coronal plane in order to conform to the curvature of the vertebrae and achieve a lower profile fixation plate 20c.

The fixation plate 20(a, b, c) of this invention is preferably thin enough and conforms to the vertebrae enough that it fits beneath the overlaying musculature and tissue so that it does not bother the users. The sockets 22(a, b, c) a are thus about 1.7 to 2.1 mm thick, with the legs 24(a, b, c) having the same thickness as the sockets 22(a, b, c) at the juncture with the sockets, and thinning to about 2 mm thick at the middle of the cross-member 70(a, b, c).

In use, the fixation plate 20c advantageously has the bushings 26 placed in the sockets 20. The fixation plate 20c is placed over the vertebrae. The vertebral body replacement 32 can be placed between the vertebrae 30 and the plate fastened after placement, or the plate 20c can be fastened before the body 32 is inserted between the vertebrae. A screw through hole 76c into the vertebral body replacement 32 fastens the fixation plate 20c to the vertebral replacement body 32, or other connections can be used.

When the fixation plate 20c is positioned over the vertebrae 30, the holes for the screws 28 can be marked and holes drilled into the vertebrae. If self tapping threads 34 and tapping tip 35 are used, the holes can be omitted, although pre-drilled pilot holes are sometimes desirable. The screws 28 are then screwed into the vertebrae using a tool having a driving bit configured to mate with the driving socket 38. The curved neck 48 of the screw 28 opens the wall segments 52 and allows the spherical portion of the head 42 to enter the wall segments 52 of the bushing. The wall segments 52 are resiliently urged inward toward the longitudinal axis of the screw 28 and the socket and engage the top edge 44 of the screw to hold it in place. The rotation of the spherical surface 42 of head 36, the rotation and translation of the bushing 26, and the flexibility of the legs 24c, allow limited movement of the fixation plate 20c relative to the vertebral body replacement 32 and the vertebrae 30.

Two Level X-Shaped Fixation Plate

Referring to FIGS. 37-43, a further embodiment is shown for fixing three vertebrae and two adjacent replacement discs believed suited for use in the C4-C7 cervical portion of the spine and believed especially suitable for fixing the C4, C5 and C6 vertebrae. This is referred to as a two-level fixation plate. Most of the parts are the same as described above and that description is not repeated. Parts that are modified have numbers that are incremented by 200, so plate 20c becomes plate 220c. This embodiment uses two X-shaped fixation plates 20c and joins them together in an integral part, referred to herein as plate 220c. The two-level fixation plate 220c has two vertebral replacement bodies 32 fastened to the plate 220c. The two level fixation plate 220c fastens to three vertebrae 30, and thus has sockets 222c and bushings 226c at locations to fasten to the three vertebrae 30. There are thus six screws 28, six bushings 226c and six sockets 222c to receive six screws 28. The two level fixation plate 220c has two X-shaped plates 220c joined at the sockets 22c common to each X-shaped frame 22c. These are denoted as sockets 222m for "middle" sockets, with the end sockets denoted as 222e for "end."

The two joined X-shaped plates 220c each have four legs 224c as described above. The middle sockets 222m have legs 224c from each X-shaped plate 220c, and thus have two legs 224c attached to each middle socket 222m. The spacing between the legs of each X-shape forming X-shaped plate 220c advantageously form an opening 223c so that the stiffness of the plate 220c at the sockets 222c is more consistent, but the opening could be omitted.

Figure 39:
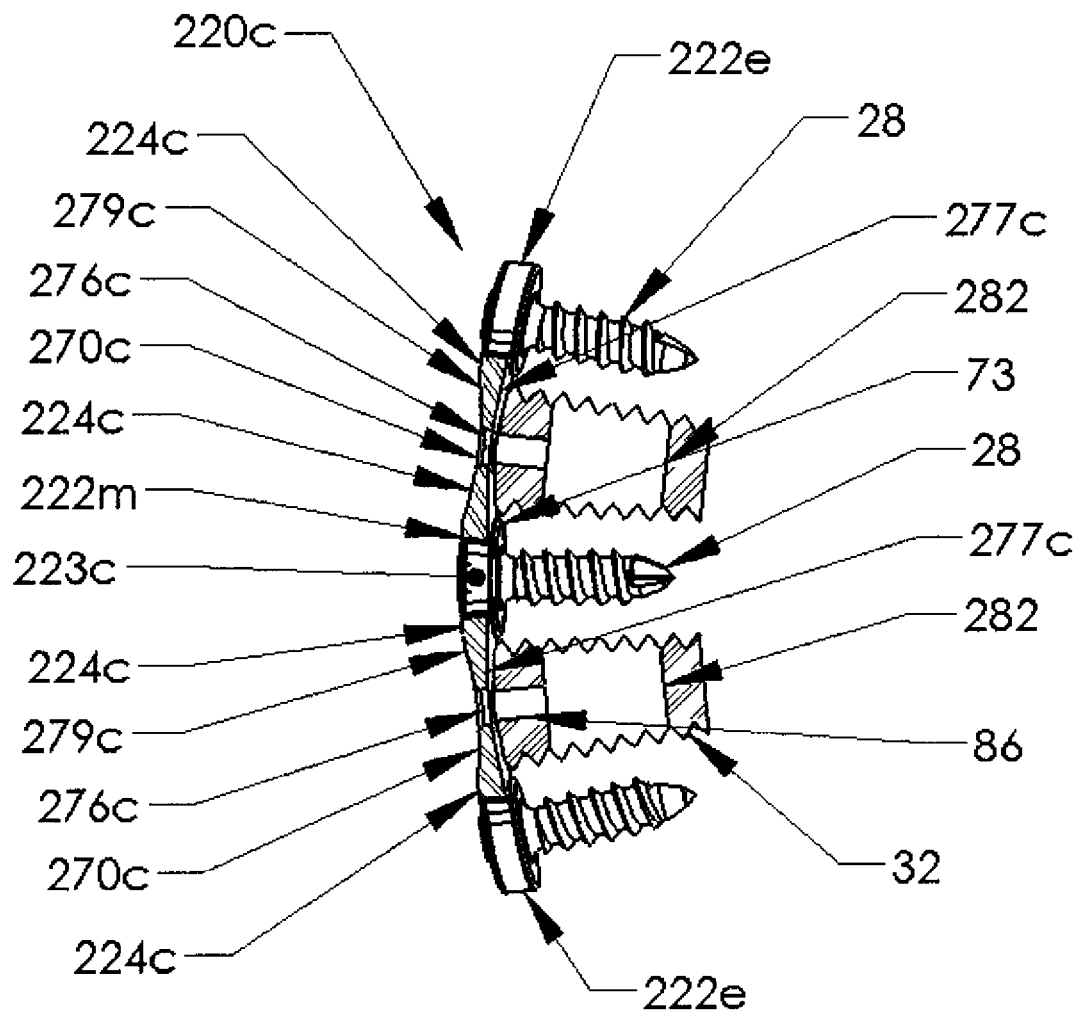
FIG. 39 is a sectional view taken along 39-39 of FIG. 38.
Figure 40:
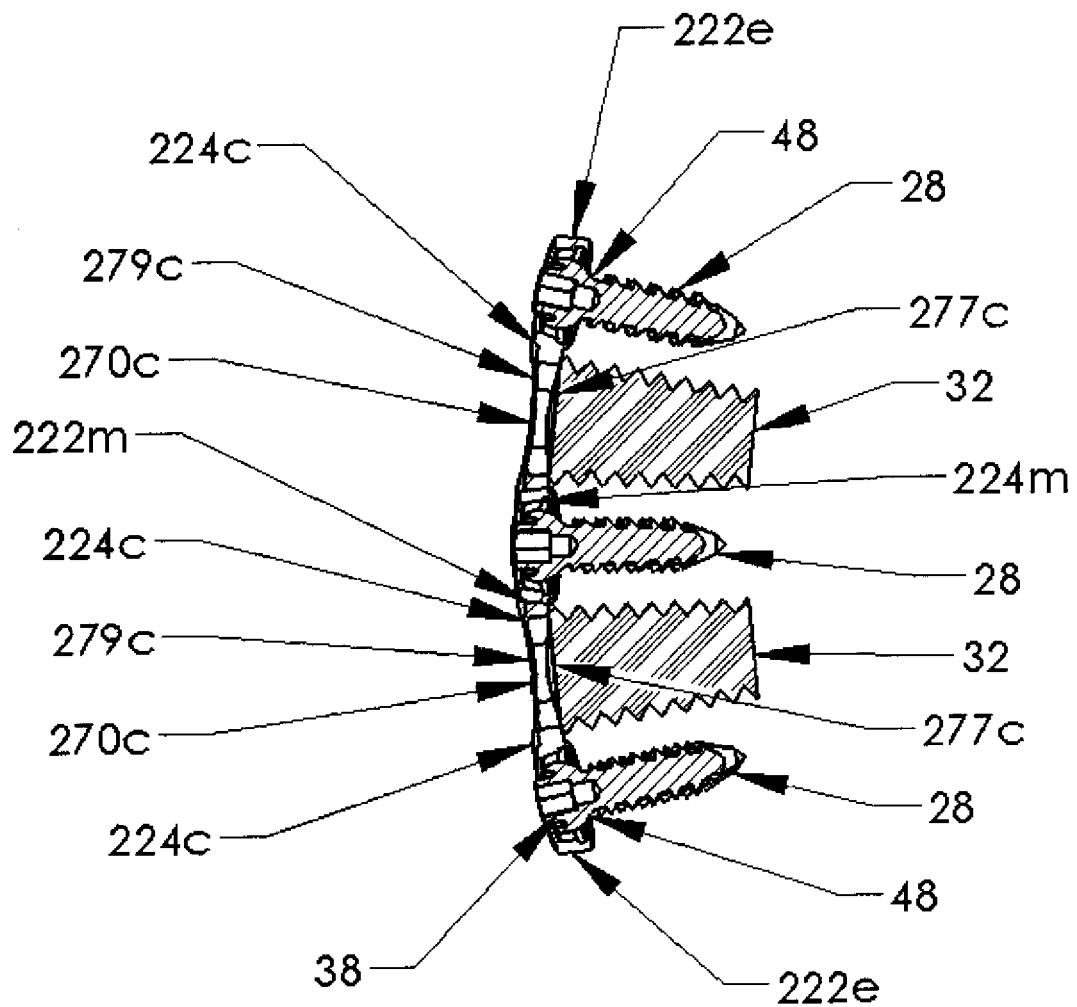
FIG. 40 is a sectional view taken along 40-40 of FIG. 38.
Figure 41:
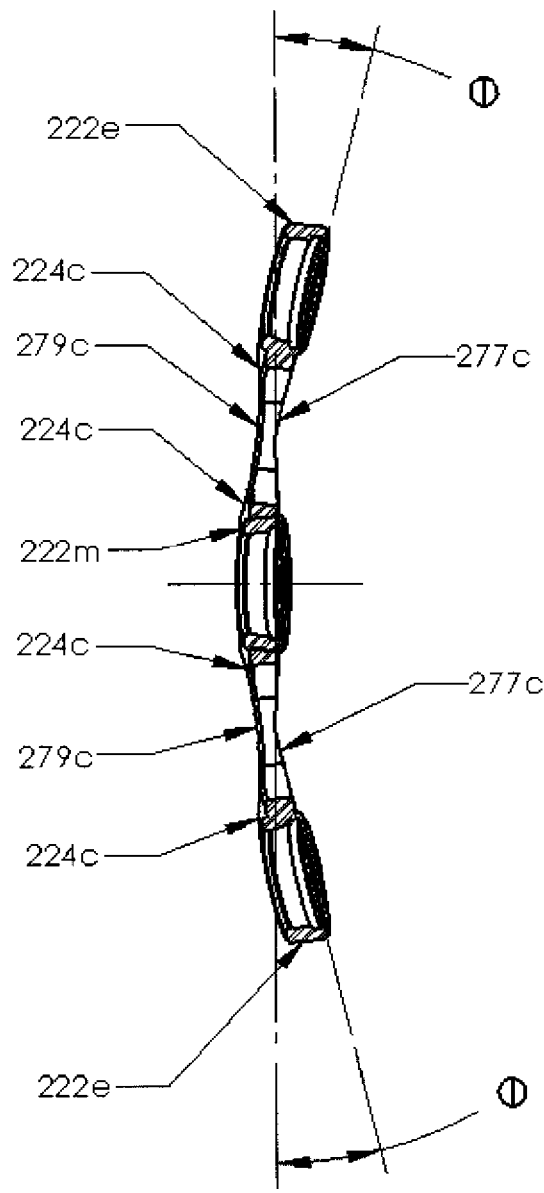
FIG. 41 is a partial sectional view taken along 40-40 of FIG. 38 but with the screws omitted.

As seen in FIGS. 39-41, the legs 224c on fixation plate 220c are thinnest at hole 276 by the connection with the vertebral body replacement 32, and thickest at the juncture with the sockets 222c. This allows the fixation plate 220c to fit close to the vertebrae 30 and helps reduce the amount by which the plate extends away from the vertebrae. This allows a low profile fixation plate which can lie below the muscle tissue and reduce the irritation and discomfort experienced by the user.

As seen in FIG. 41, the fixation plate 220c is preferably angled or curved slightly about two perpendicular axes intersecting at the center of hole 223c in order to better conform to the local spinal shape. Thus, two sockets 222e on opposing sides of the cross-member 270c are bent or inclined slightly in the same anterior direction so the cross-member 270c is at the apex of a slightly V-shaped plate. Alternately described, the sockets 222e on opposing sides of the cross-member 270c are bent or inclined relative to the axial plane extending between adjacent, joined vertebrae 30 and extending through the cross-member 270c and center opening 223c. The sockets 222e on the superior side of cross-member 270 are inclined slightly toward the sockets 222e on the inferior side of the cross-member and vice-versa. The sockets 222e and legs 224c are inclined at an angle □ of about 14° relative to a plane parallel to the coronal plane through the posterior of the cross-member 270c, as best seen in FIG. 41. Inclination angles □ from about 12° to about 16° are believed usable, but could be further varied for individual skeletal variations. The inclination angle □ is selected to conform to the curvature of the cervical vertebrae. The angle can vary depending on which vertebrae are joined by the fixation plate 220c, and depending on whether an average curvature is used or on whether variations are made to accommodate an individual's specific spinal curvature. Preferably, the fixation plate 220c is made according to a predetermined curvature such as the average spinal curvature, with the plate being custom bent into a final shape that is based on X-rays of the spinal curvature of a specific user.

Figure 42:
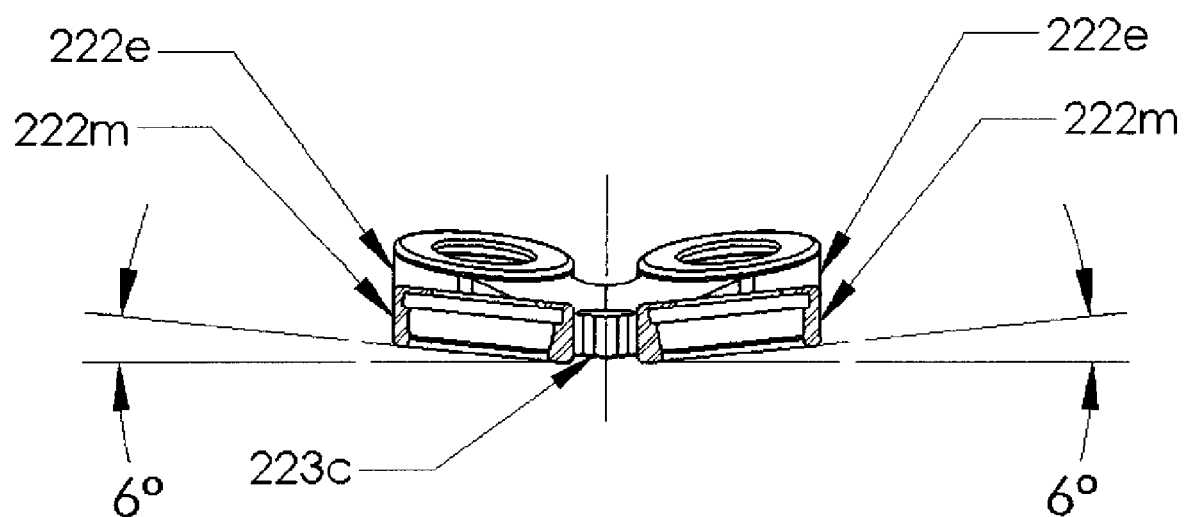
FIG. 42 is a sectional view taken along 42-42 of FIG. 38.
Figure 43:
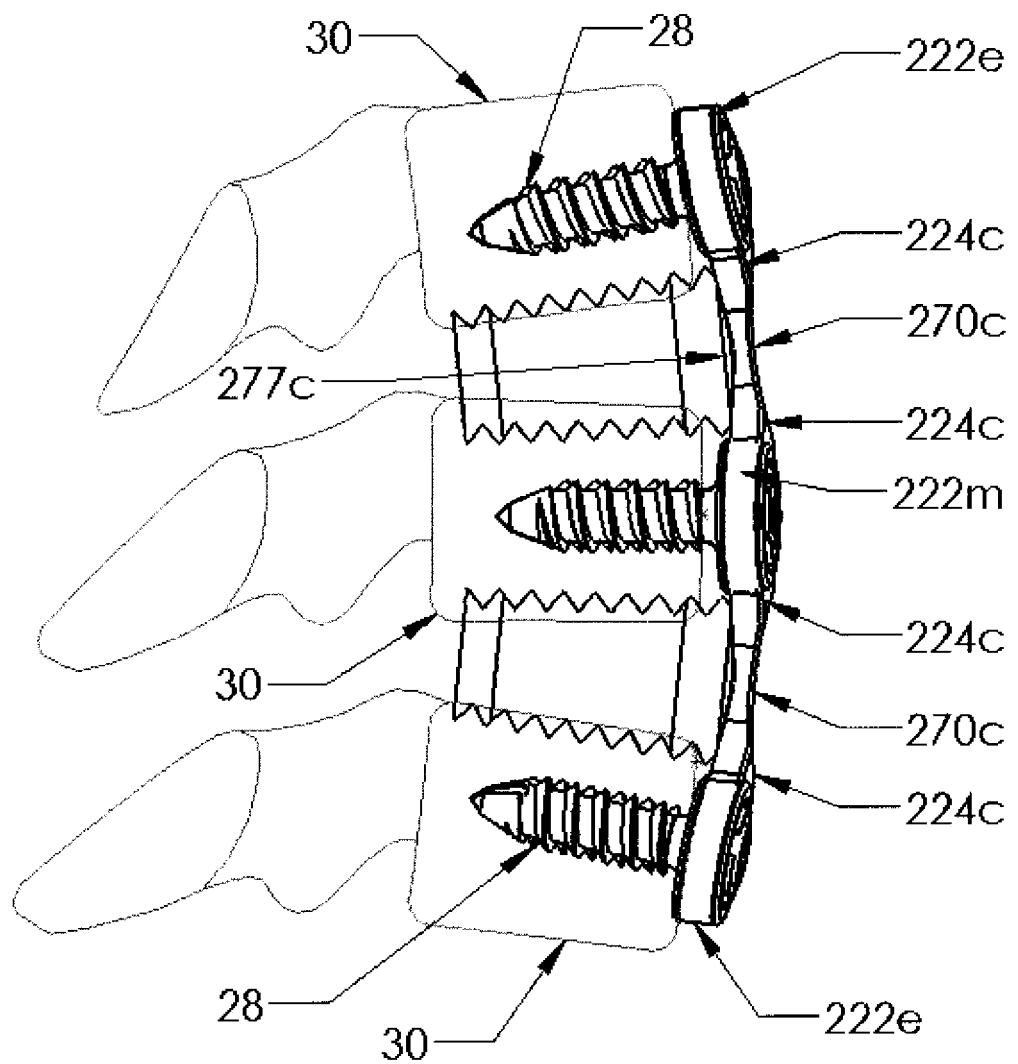
FIG. 43 is a partial sectional view showing the two-level X-shaped fixation plates of FIG. 37 fastened to vertebrae.
Figure 44:
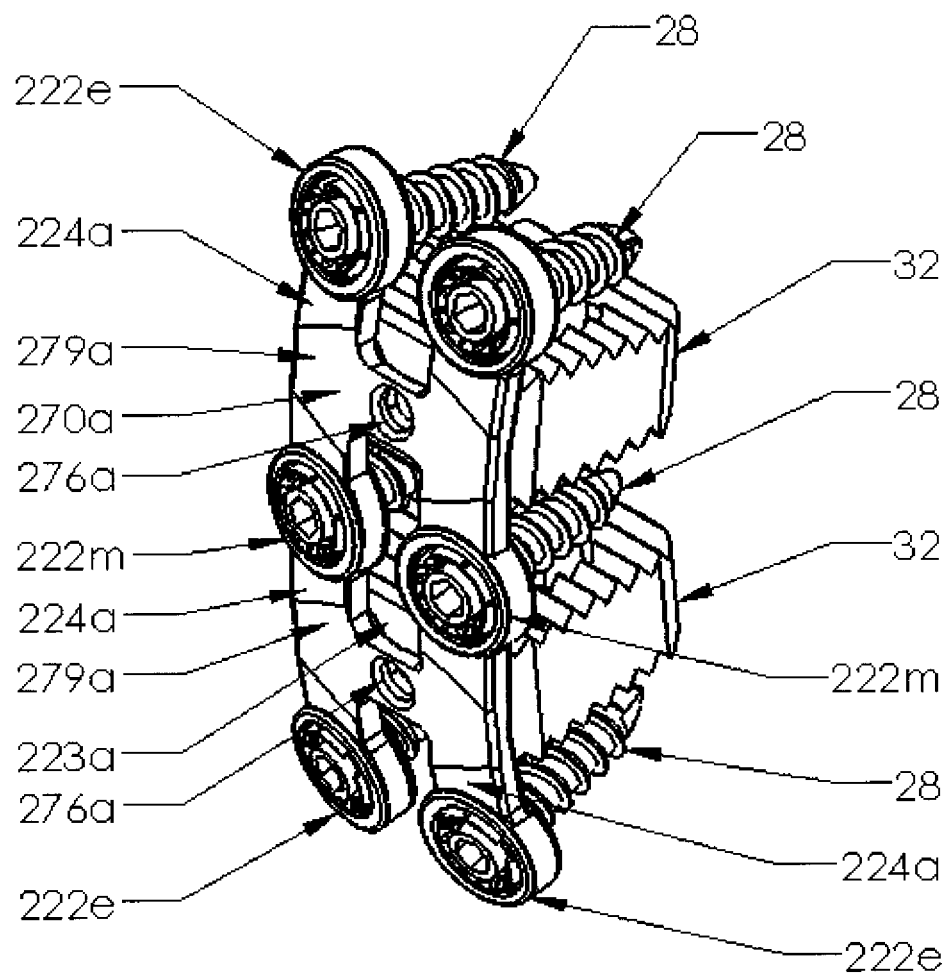
FIG. 44 is a perspective view of a further embodiment showing a two-level H-shaped fixation plate with two vertebral body replacements.
Figure 45:
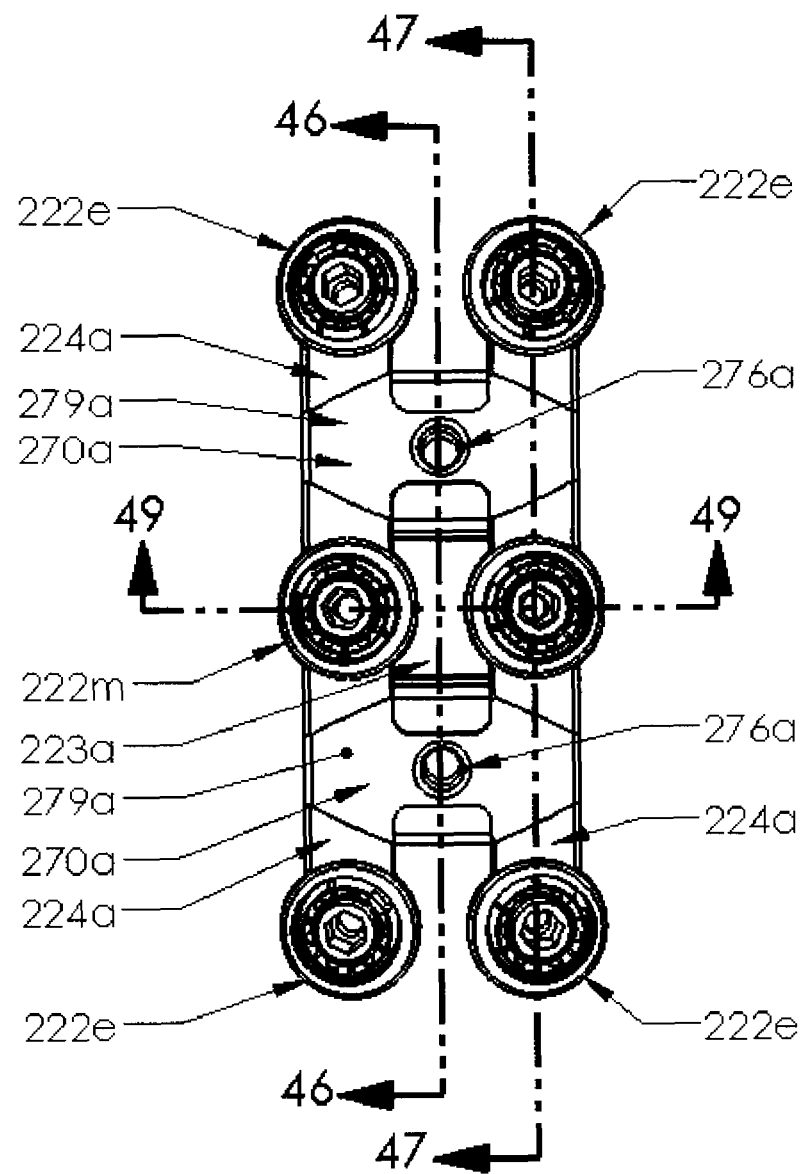
FIG. 45 is a plan front view of the two-level H-shaped fixation plate of FIG. 44.
Figure 47:
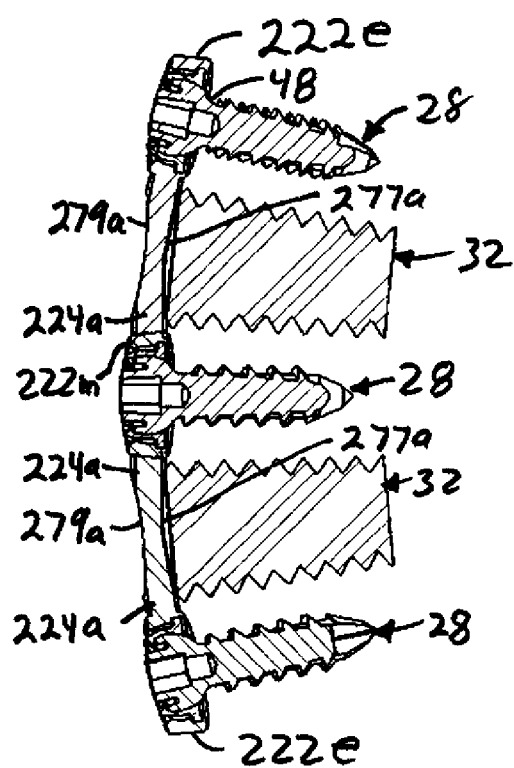
FIG. 47 is a sectional view taken along 47-47 of FIG. 45.
Figure 46:
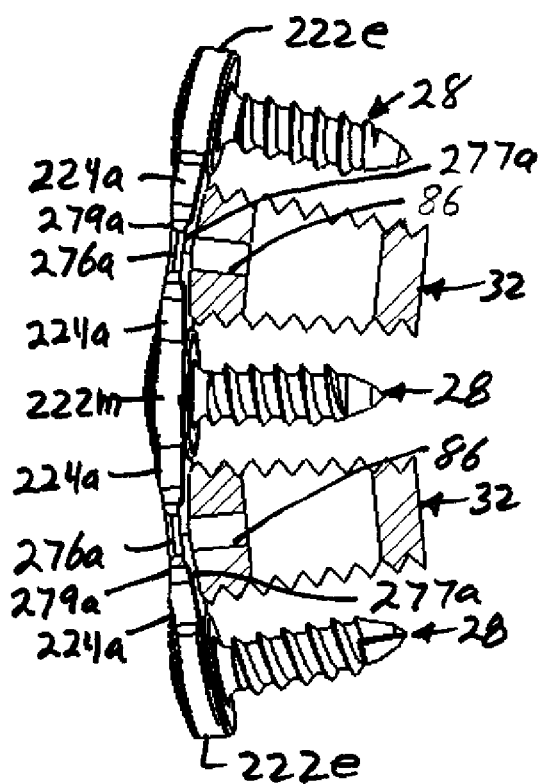
FIG. 46 is a sectional view taken along 46-46 of FIG. 45.
Figure 49:
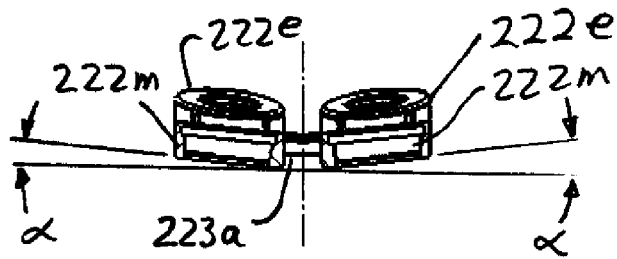
FIG. 49 is a sectional view taken along 49-49 of FIG. 45.
Figure 50:
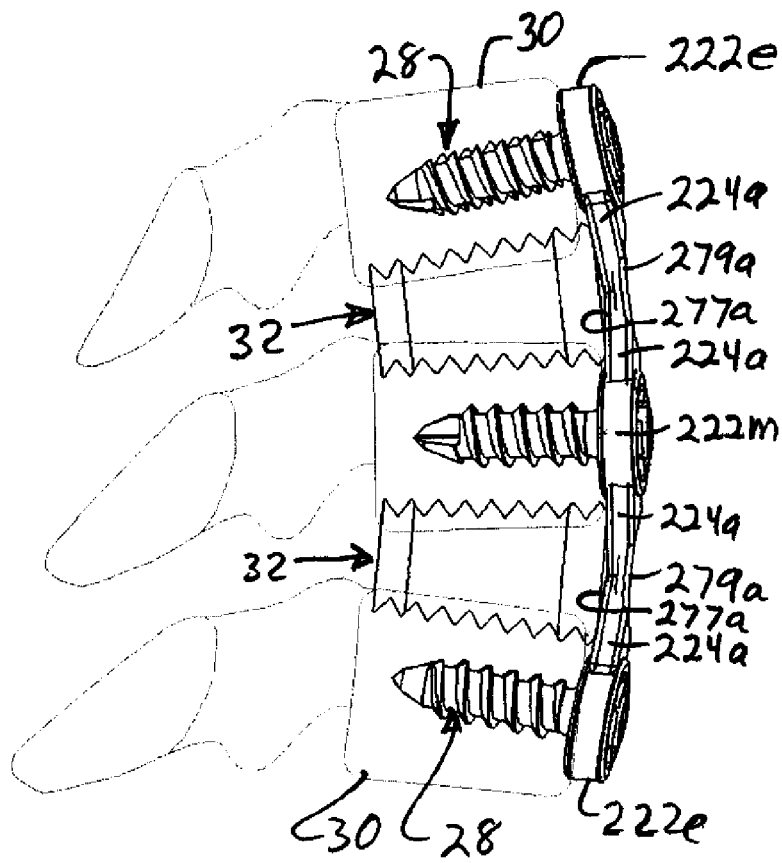
FIG. 50 is a partial sectional view showing the two-level H-shaped fixation plate of FIG. 44 fastened to vertebrae.
Figure 48:
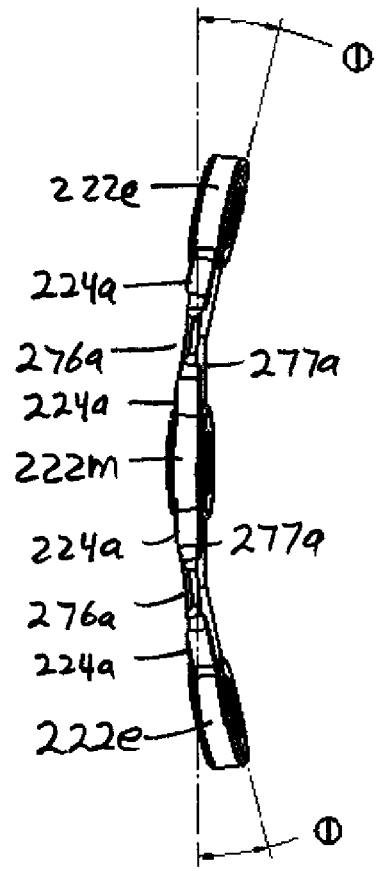
FIG. 48 is a partial sectional view taken along 47-47 of FIG. 45 but with the screws omitted.
Figure 51:
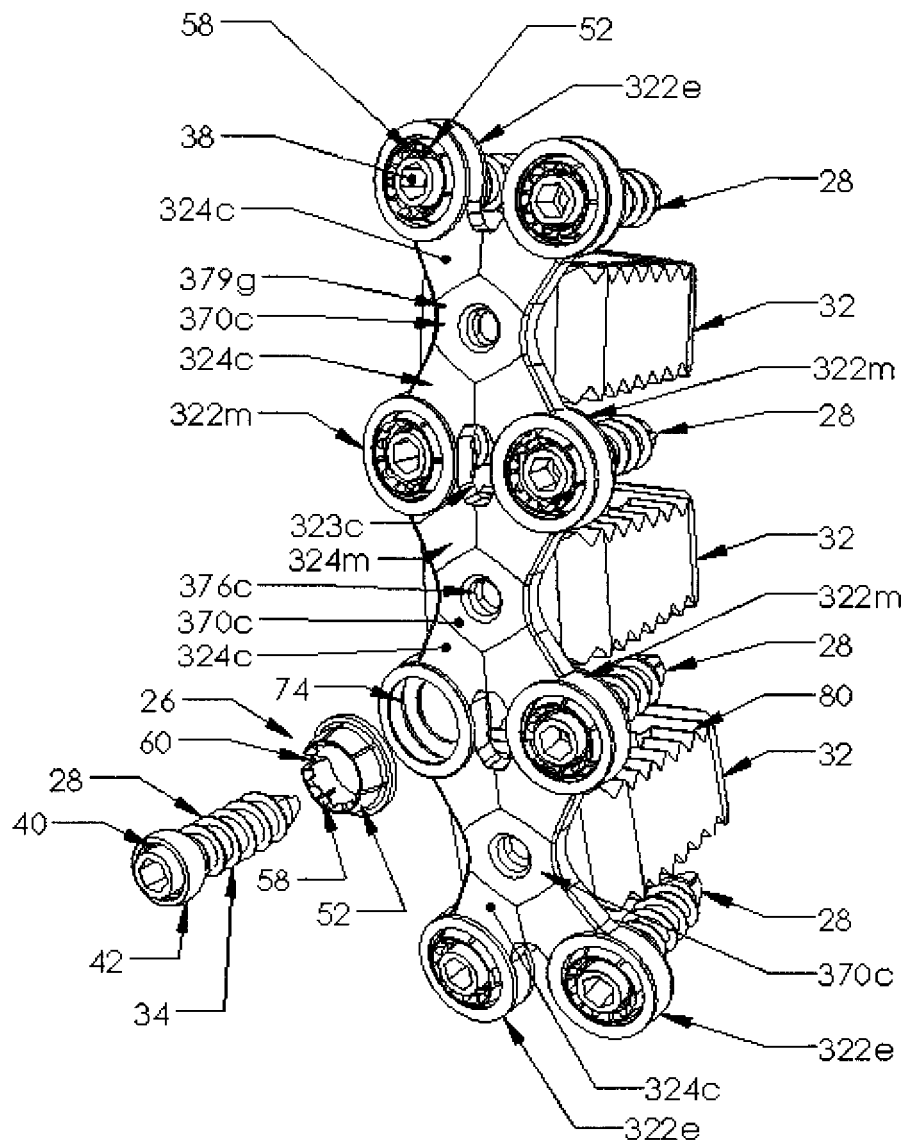
FIG. 51 is a partially exploded perspective view of a further embodiment showing a three-level X-shaped fixation plate with three vertebral body replacements.
Figure 52:
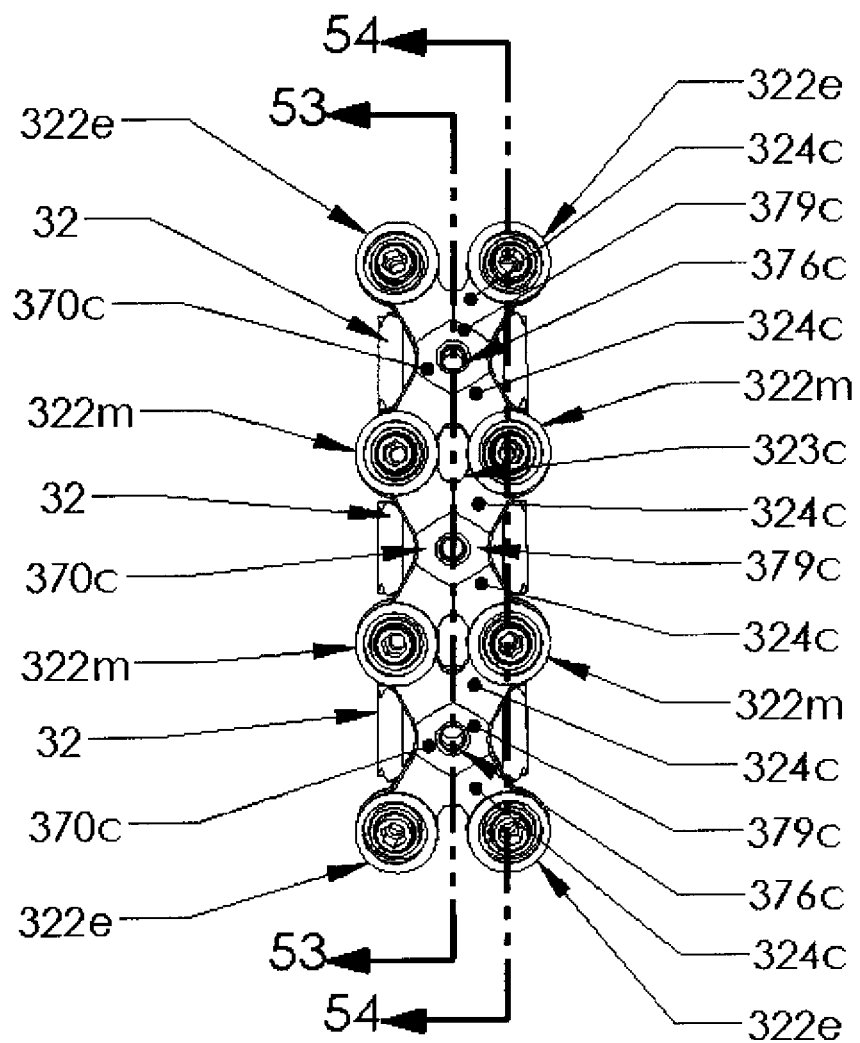
FIG. 52 is a plan front view of the three-level X-shaped fixation plate of FIG. 51.

The fixation plate 220c is inclined about two axes, and thus the legs 222e on opposing sides of a sagittal plane through the center of opening 223c and openings 276c are inclined toward each other at an angle α of about 6° as best seen in FIG. 42. The resulting position and inclination of the sockets 222e and 222m allows a lower profile fixation plate as discussed above. To help maintain this low profile, the thickness of the sockets 222e and 222m are advantageously about 2.1 mm.

The installation and use of the two level, X-shaped fixation plate 220c is much like the installation and use of the single level plate 20c, except that two discs are removed from between two adjacent vertebrae 30 and two vertebral body replacements 32 are inserted to replace those two removed discs. The replacement bodies 32 can be pre-attached, or they can be attached shortly before insertion, or the bodies 32 can be inserted between vertebrae and the plate 220c can be fastened to the bodies 32. Additionally, if a vertebral replacement body 32 is already in place and a disc is removed from an adjacent vertebrae, then the preexisting body 32 can possibly be left in position and the fixation plate 220c fastened to the preexisting, in-place vertebral replacement body, although it is believed preferable to remove the body 32 and replace it. Indeed, because the fixation plates 20a, 20b, 20c, 220c are compatible with preexisting vertebral replacement bodies 32, the preexisting and pre-inserted bodies 32 can be left in place and the prior art fixation plates can be replaced with any suitable fixation plate described herein.

Two Level H-Shaped Fixation Plate

Referring to FIGS. 44-50, a further embodiment is shown for fixing three vertebrae and two adjacent replacement discs and is believed suited for use in the C4-C7 cervical portion of the spine and believed especially suitable for fixing the C4, C5 and C6 vertebrae. This is also referred to as a two-level fixation plate. Most of the parts are the same as described above and that description is not repeated. Parts that are modified have numbers that are incremented by 200, so plate 20a becomes plate 220a. This embodiment uses two H-shaped fixation plates 20a and joins them together in an integral part, referred to herein as plate 220a. The two-level fixation plate 220a has two vertebral replacement bodies 32 fastened to the plate 220a. The two level fixation plate 220a fastens to three vertebrae 30, and thus has sockets 222a and bushings 226a at locations to fasten to the three vertebrae 30. There are thus six screws 28, six bushings 226a and six sockets 222a to receive six screws 28. The two level fixation plate 220a has two H-shaped plates 220a joined at the sockets 22a common to each X-shaped frame 222a. These are denoted as sockets 222m for "middle" sockets, with the end sockets denoted as 222e for "end."

The two joined H-shaped plates 20a each have four legs 224a as described above. The middle sockets 222m have legs 24a from each H-shaped plate 20a, and thus have two legs 224a attached to each middle socket 222m. The spacing between the legs of each H-shape forming H-shaped plate 220a advantageously form an opening 223a so that the stiffness of the plate 220a at the sockets 222a is more consistent, but the opening could be omitted.

The legs 224a on fixation plate 220a are thinnest at hole 276 by the connection with the vertebral body replacement 32, and thickest at the juncture with the sockets 220a. This allows the fixation plate 220a to fit close to the vertebrae 30 and helps reduce the amount by which the plate extends away from the vertebrae. This allows a low profile fixation plate which can lie below the muscle tissue and reduce the irritation and discomfort experienced by the user.

The fixation plate 220a is preferably angled or curved slightly about two perpendicular axes intersecting at the center of hole 223a in order to better conform to the local spinal shape. Thus, two sockets 222e on opposing sides of the cross-member 270a are bent or inclined slightly in the same anterior direction so the cross-member 270a is at the apex of a slightly V-shaped plate. Alternately described, the sockets 222e on opposing sides of the cross-member 270a are bent or inclined relative to the axial plane extending between adjacent, joined vertebrae 30 and extending through the cross-member 270c and center opening 223a. The sockets 222e on the superior side of cross-member 270a are inclined slightly toward the sockets 222e on the inferior side of the cross-member and vice-versa. The sockets 222e and legs 24a are inclined at an angle □ of about 14° relative to a plane parallel to the coronal plane through the posterior of the cross-member 270a, as best seen in FIG. 41. Inclination angles □ from about 11° to about 16° are believed usable, but could be further varied for individual skeletal variations. The inclination angle □ is selected to conform to the curvature of the cervical vertebrae. The angle can vary depending on which vertebrae are joined by the fixation plate 220a, and depending on whether an average curvature is used or on whether variations are made to accommodate an individual's specific spinal curvature. The fixation plate 220a is inclined about two axes, and thus the legs 222e on opposing sides of a sagittal plane through the center of opening 223a and openings 276a are inclined toward each other at an angle α of about 6° as best seen in FIG. 42. The resulting position and inclination of the sockets 222e and 222m allows a lower profile fixation plate as discussed above.

The installation and use of the two level, H-shaped fixation plate 220a is much like the installation and use of the single level plate 20a, except that two discs are removed from between two adjacent vertebrae 30 and two vertebral body replacements 32 are inserted to replace those two removed discs. The replacement bodies 32 can be pre-attached, or they can be attached shortly before insertion, or the bodies 32 can be inserted between vertebrae and the plate 220a can be fastened to the bodies 32. Additionally, if a vertebral replacement body 32 is already in place and a disc is removed from an adjacent vertebrae, then the preexisting body 32 can possibly be left in position and the fixation plate 220a fastened to the preexisting, in-place vertebral replacement body, although it is believed preferable to remove the body 32 and replace it. Indeed, because the fixation plates 20a, 20b, 20c, 220c. 220a are compatible with preexisting vertebral replacement bodies 32, the preexisting and pre-inserted bodies 32 can be left in place and the prior art fixation plates can be replaced with any suitable fixation plate described herein.

Three Level X-Shaped Fixation Plate

Referring to FIGS. 51-57, a further embodiment is shown for fixing four vertebrae and three intervening replacement discs and is believed suited for use in the C4-C7 cervical portion of the spine and believed especially suitable for fixing the C4, C5 and C6 vertebrae. This is referred to as a three-level fixation plate. Most of the parts are the same as described above and that description is not repeated. Parts that are modified have numbers that are incremented by 300, so plate 20c becomes plate 320c. This embodiment uses three X-shaped fixation plates 20c and joins them together in an integral part, referred to herein as plate 320c. The three-level fixation plate 320c has three vertebral replacement bodies 32 fastened to the plate 320c. The three level fixation plate 320c fastens to three vertebrae 30, and thus has sockets 322c and bushings 326c at locations to fasten to the three vertebrae 30. There are thus eight screws 28, eight bushings 326c and eight sockets 322c to receive eight screws 28. The two level fixation plate 320c has two X-shaped plates 22c joined at the sockets 22c common to each X-shaped frame 322c. These are denoted as sockets 322m for "middle" sockets, with the end sockets denoted as 322e for "end."

The three joined X-shaped plates 320c each have four legs 324c as described above. The middle sockets 322m have legs 324c from each X-shaped plate 320c, and thus have two legs 324c attached to each middle sockets 322m. The spacing between the legs of each X-shape forming X-shaped plate 320c advantageously form an opening 323c so that the stiffness of the plate 320c at the sockets 322c is more consistent, but the opening could be omitted.

Figure 53:
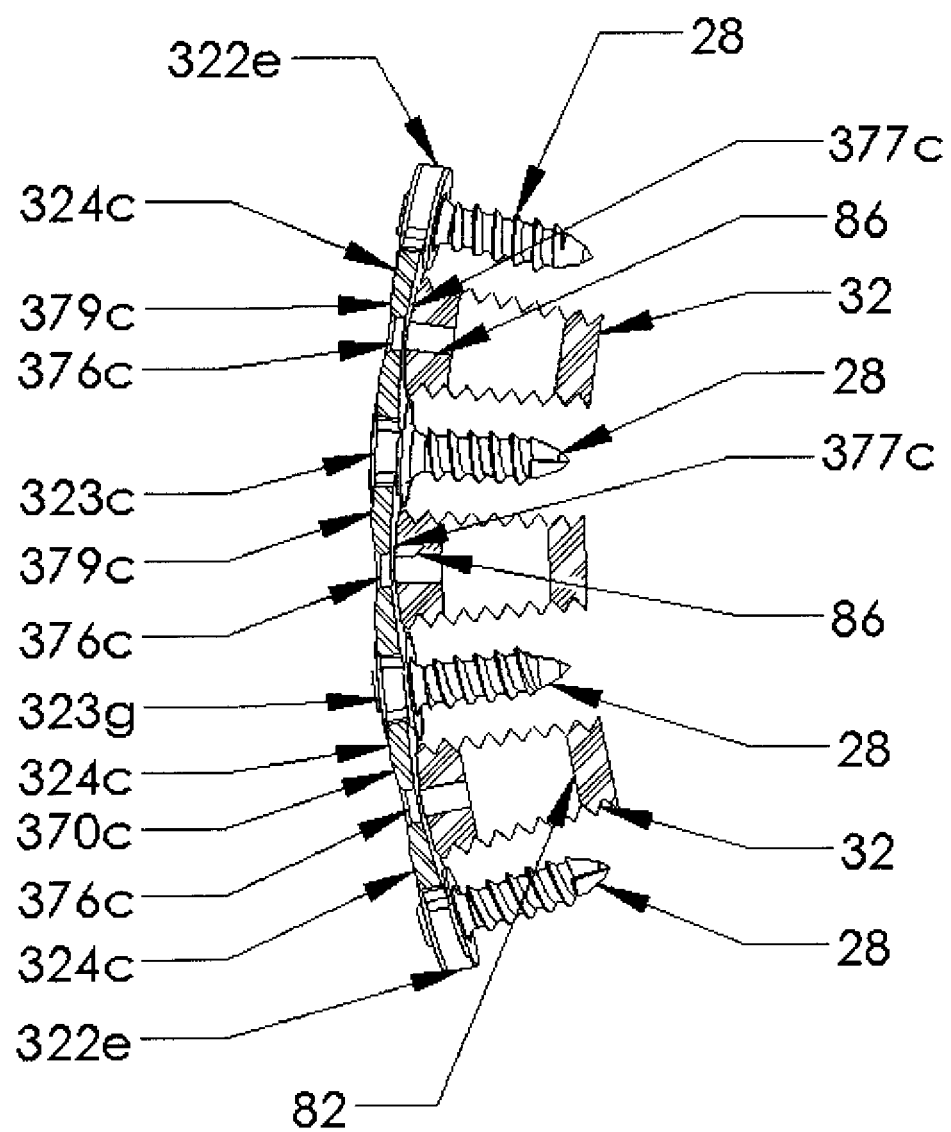
FIG. 53 is a sectional view taken along 53-53 of FIG. 52.
Figure 54:
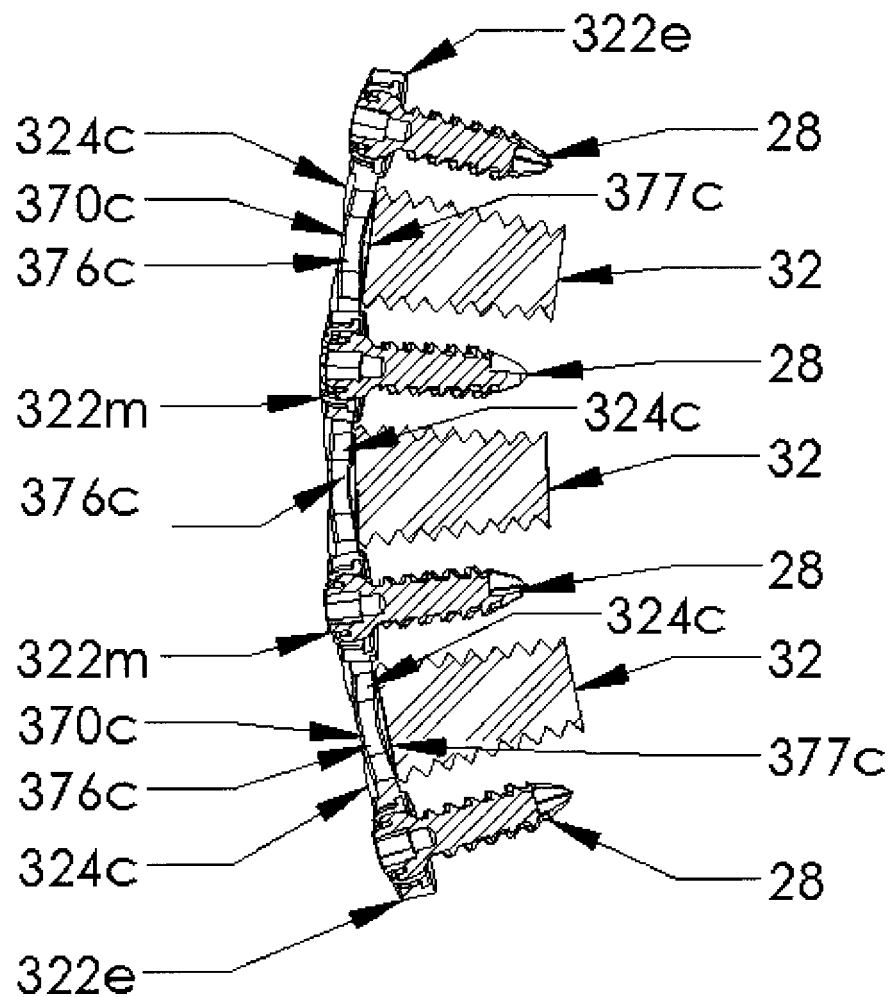
FIG. 54 is a sectional view taken along 54-54 of FIG. 52.
Figure 55:
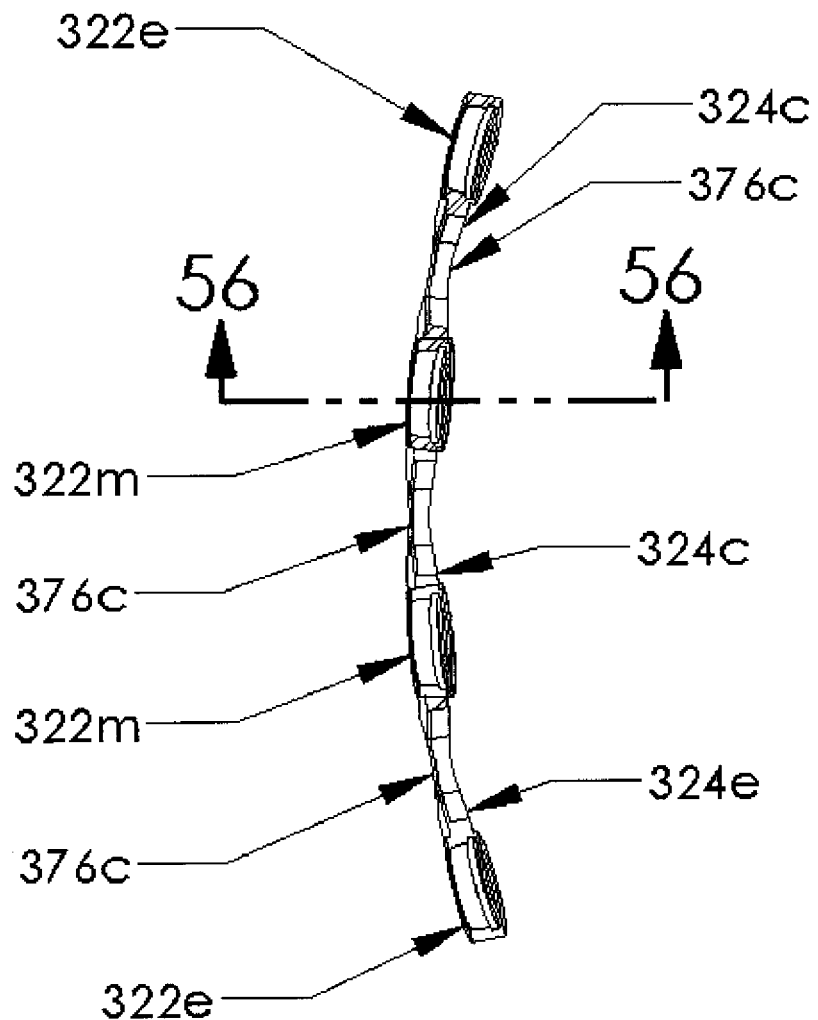
FIG. 55 is a partial sectional view taken along 54-54 of FIG. 52 but with the screws omitted.
Figure 57:
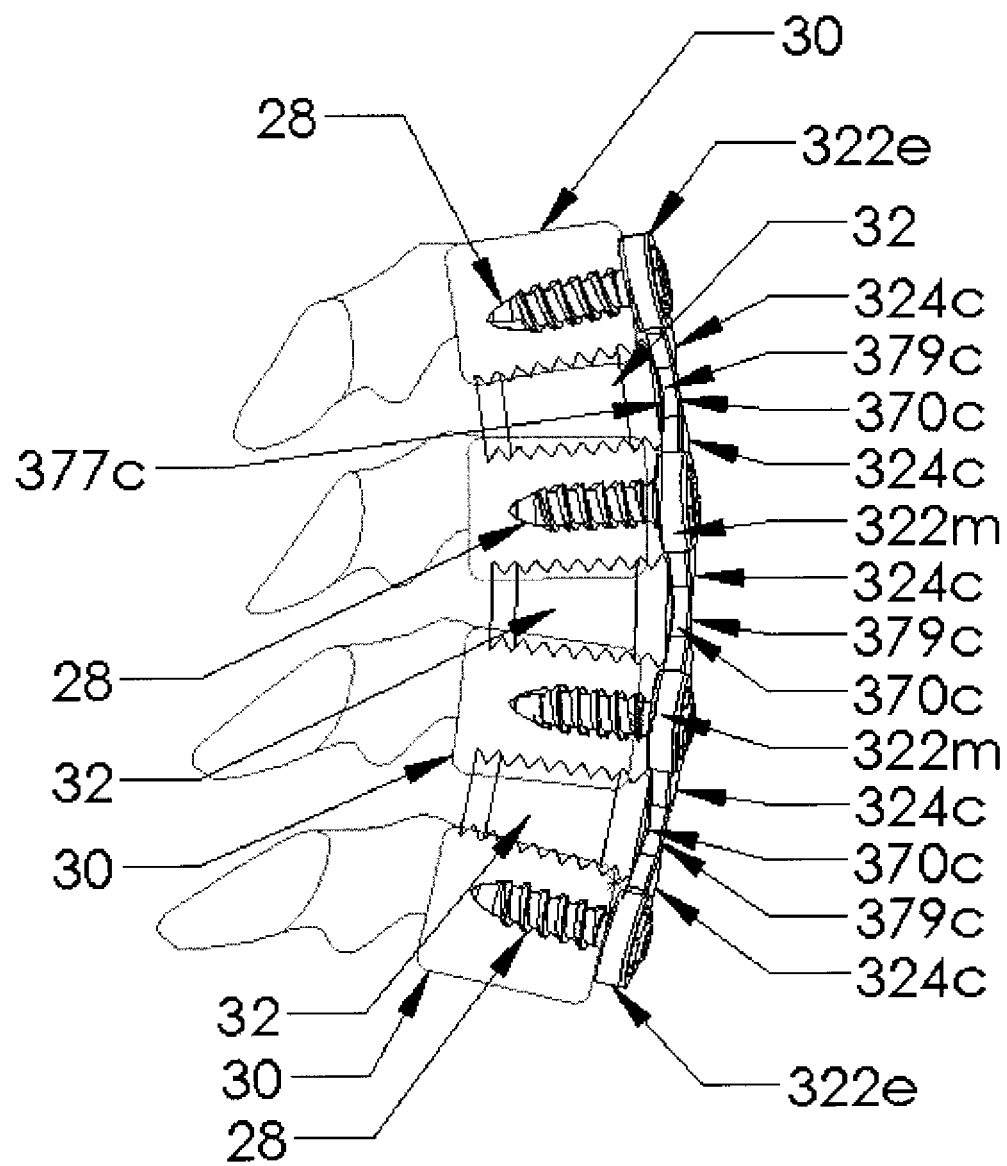
FIG. 57 is a partial sectional view showing the three-level X-shaped fixation plate of FIG. 51 fastened to vertebrae.
Figure 58:
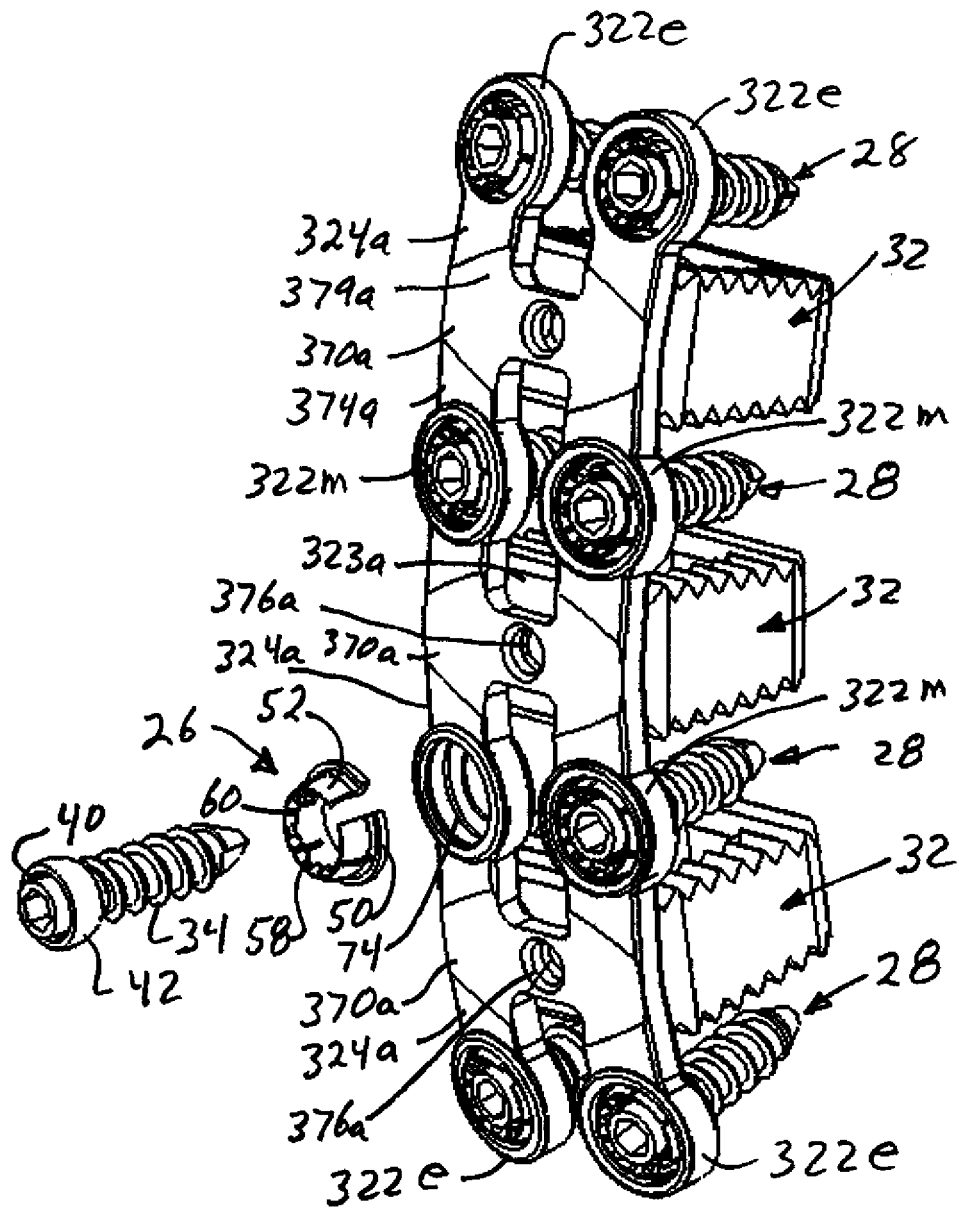
FIG. 58 is a partially exploded perspective view of a further embodiment showing a three-level H-shaped fixation plate with three vertebral body replacements.
Figure 59:
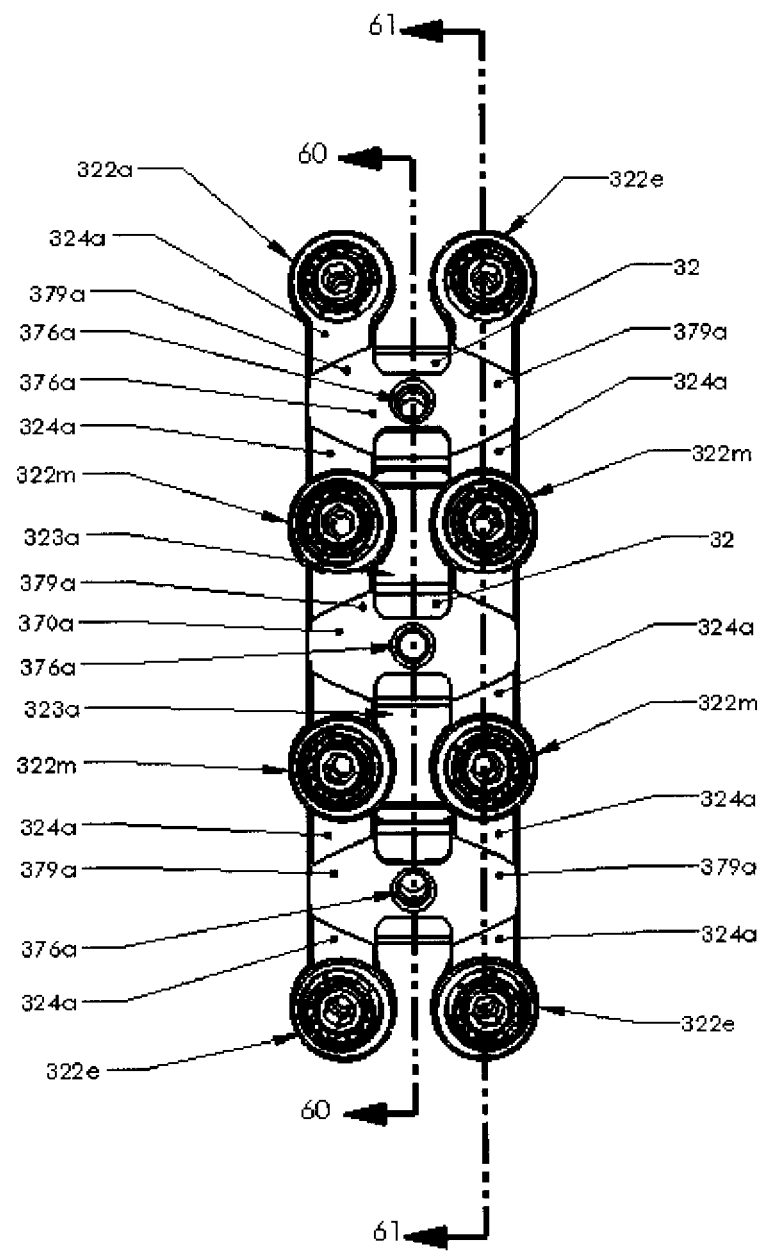
FIG. 59 is a plan front view of the three-level H-shaped fixation plate of FIG. 58
Figure 60:
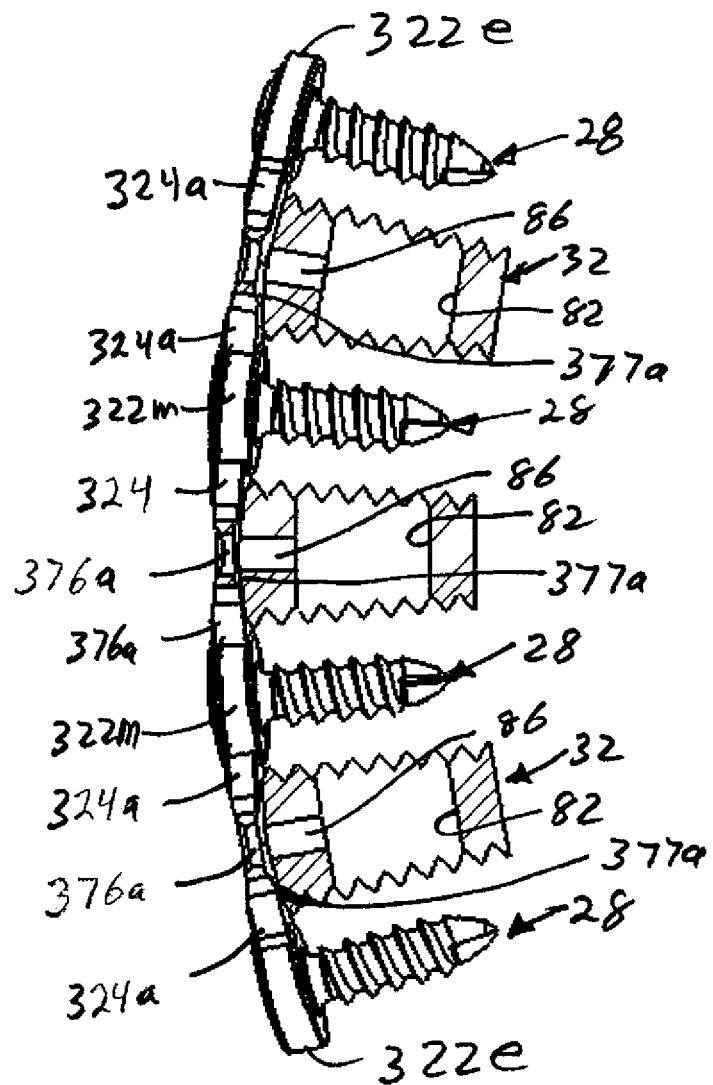
FIG. 60 is a sectional view taken along 60-60 of FIG. 59.
Figure 61:
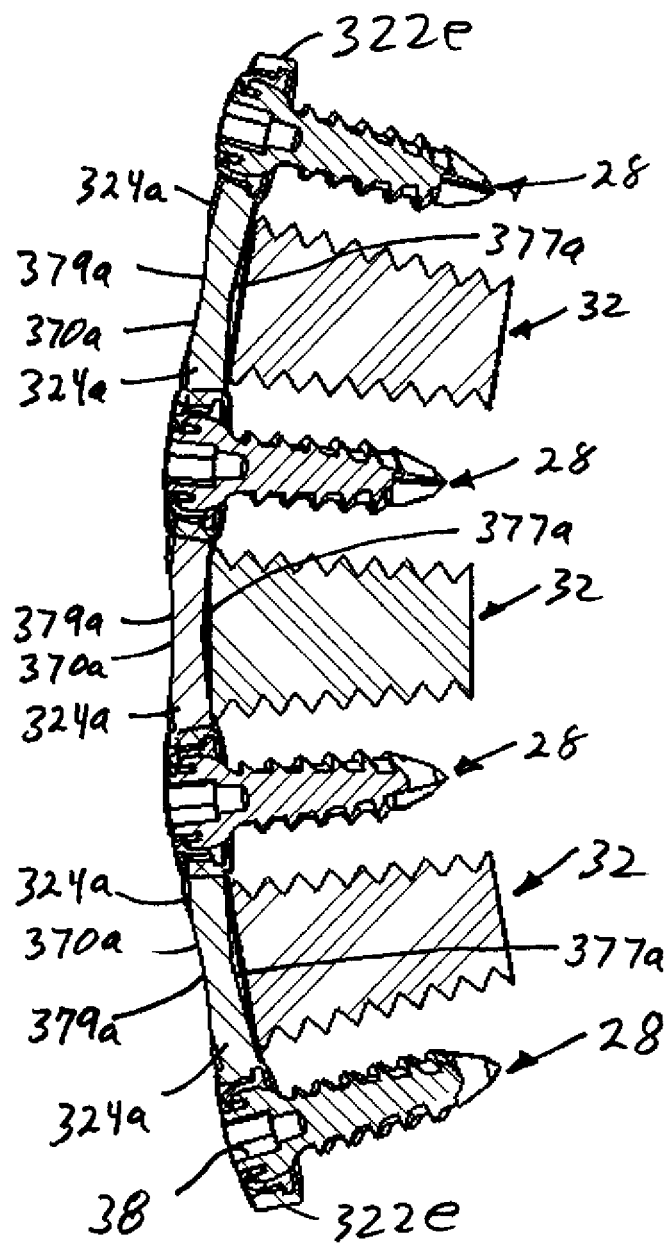
FIG. 61 is a sectional view taken along 61-61 of FIG. 59.
Figure 63:
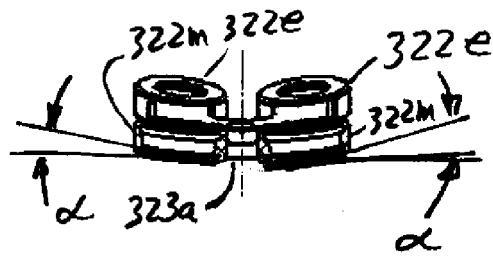
FIG. 63 is a sectional view taken along 63-63 of FIG. 59.
Figure 64:
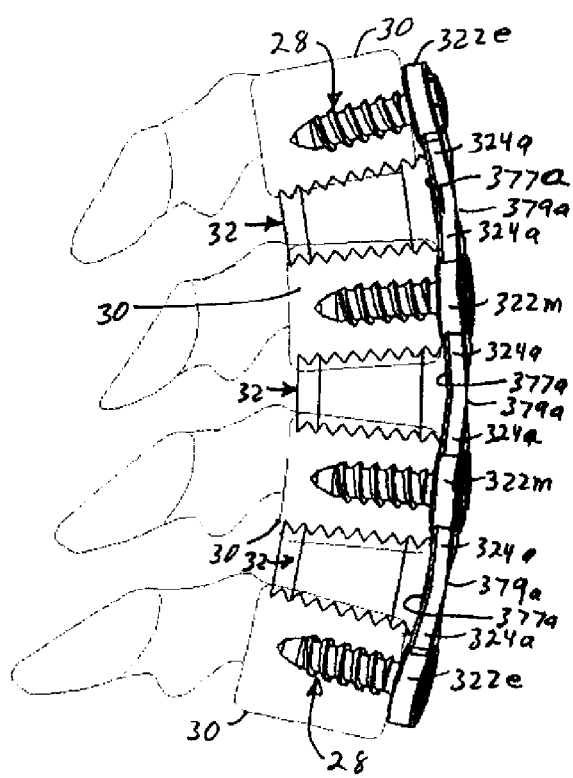
FIG. 64 is a partial sectional view showing the three-level H-shaped fixation plate of FIG. 58 fastened to vertebrae.
Figure 62:
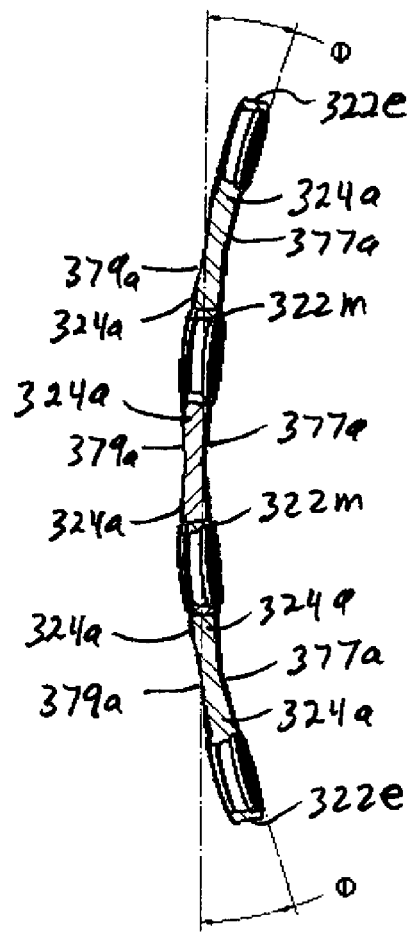
FIG. 62 is a partial sectional view taken along 61-61 of FIG. 59 but with the screws omitted.
Figure 65:
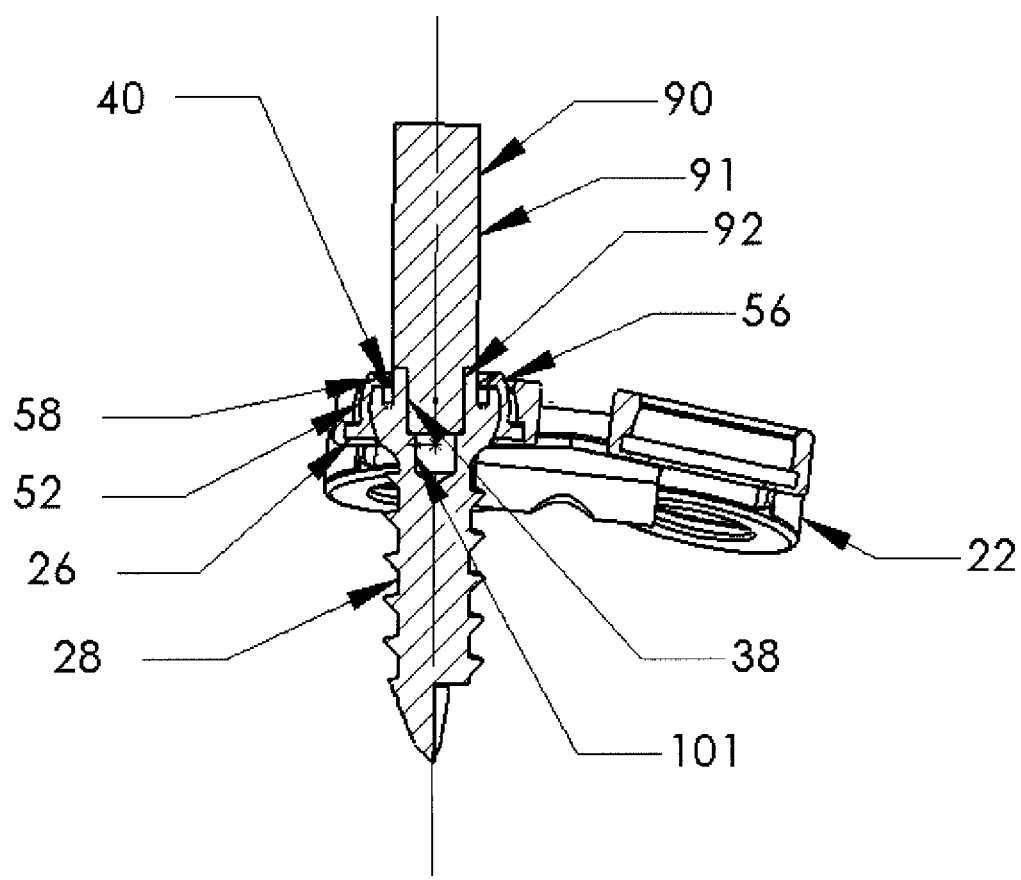
FIG. 65 is a sectional view of an installation tool engaging a bone screw driven into a socket of a fixation plate.
Figure 66:
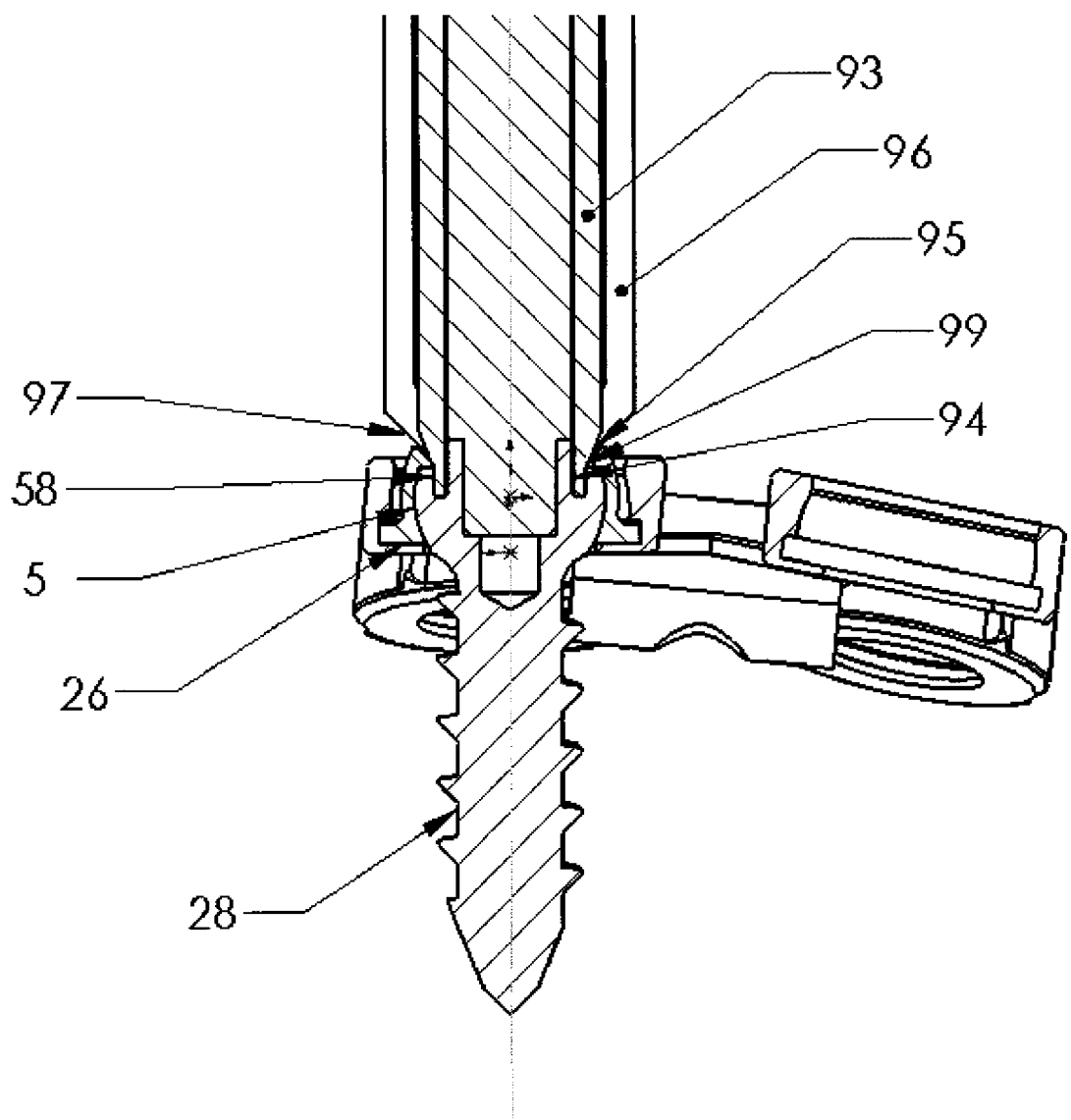
FIG. 66 is a sectional view of the installation tool of FIG. 65 with a bushing unlocking tool encircling the installation tool.
Figure 67:
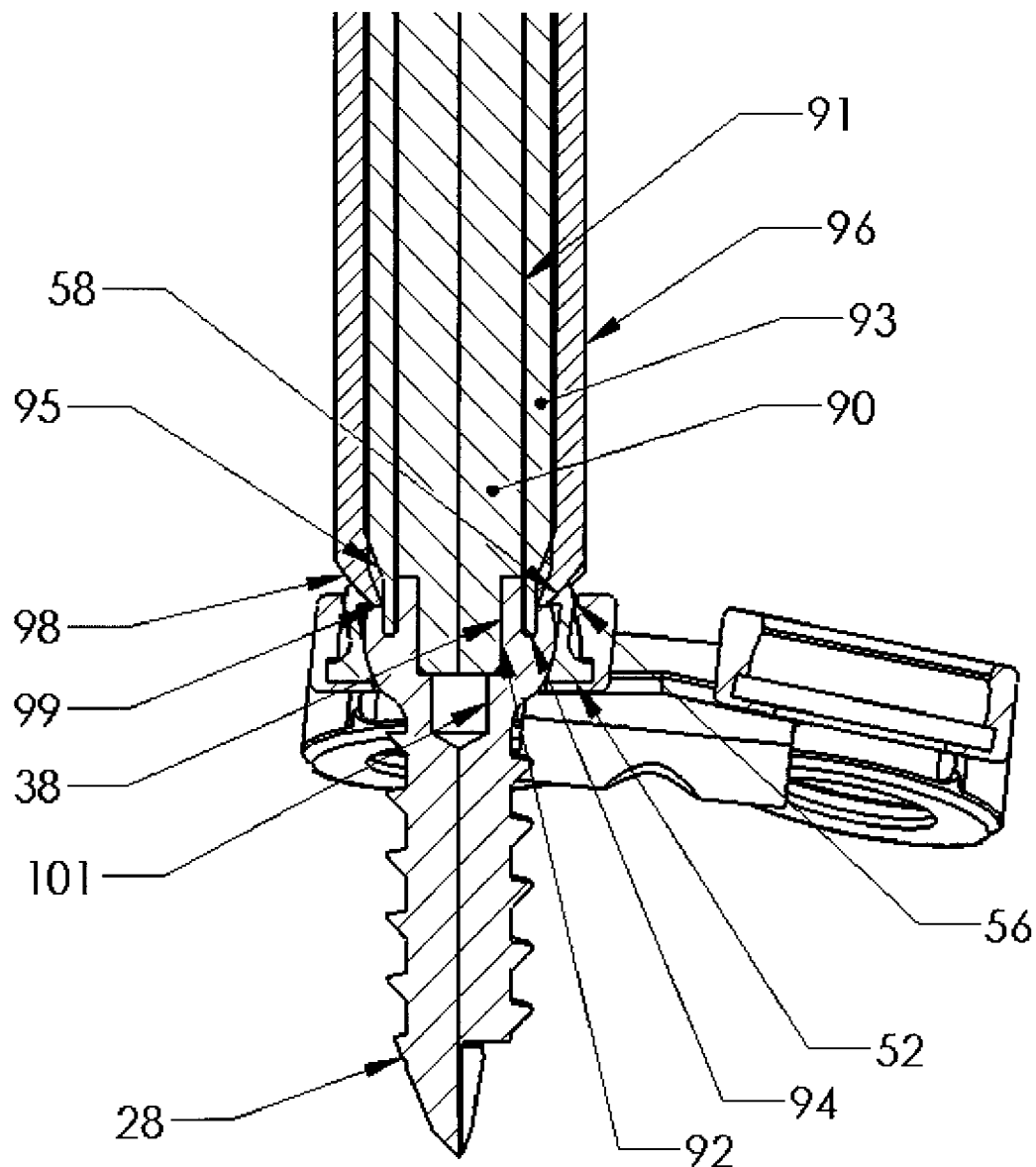
FIG. 67 is a sectional view of the a bushing unlocking tool of FIG. 66 unlocking a bushing from engagement with a screw engaged by an installation tool

As seen in FIGS. 53, 55 and 57, the legs 324c on each segment of fixation plate 320c are thinnest at hole 376 by the connection with the vertebral body replacement 32, and thickest at the juncture with the sockets 322c. This allows the fixation plate 320c to fit close to the vertebrae 30 and helps reduce the amount by which the plate extends away from the vertebrae. This allows a low profile fixation plate which can lie below the muscle tissue and reduce the irritation and discomfort experienced by the user.

Figure 56:
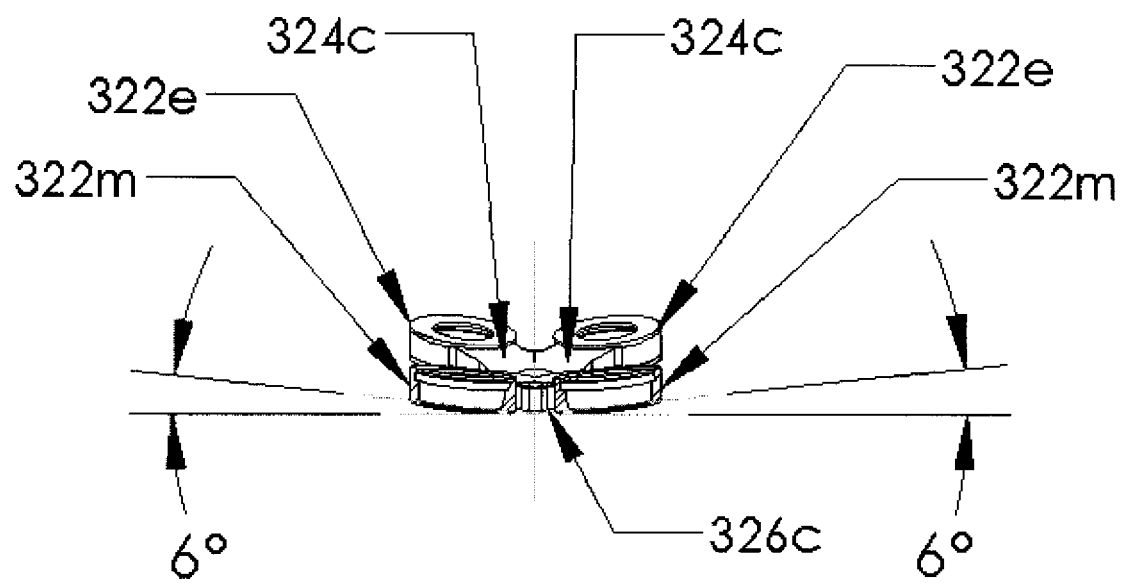
FIG. 56 is a sectional view taken along 56-56 of FIG. 55.

As seen in FIGS. 53, 55 and 56, the fixation plate 320c is preferably angled or curved slightly about two perpendicular axes intersecting at the center of the three holes 376 in order to better conform to the local spinal shape. Thus, sockets 322e and two sockets 322m on opposing sides of the cross-member 270c containing the middle hole 376c are bent or inclined slightly in the same anterior direction so the cross-member 370c is at the apex of a slightly V-shaped plate. Alternately described, the sockets 322e and 322m on opposing sides of the cross-member 370c containing the middle of three holes 376c are bent or inclined relative to the axial plane extending between adjacent, joined vertebrae 30 and extending through the cross-member 370c and the middle of the three openings 376c. The sockets 322e on the superior side of the middle cross-member 370c are inclined slightly toward the sockets 322e on the inferior side of the cross-member and vice-versa. The sockets 322e and legs 324c are inclined at an angle □ of about 18° relative to a plane parallel to the coronal plane through the posterior of the middle cross-member 370c, as best seen in FIG. 55. The sockets 322m are inclined at an angle of about 14° as in the two-level plate. Inclination angles □ from about 16° to about 20° are believed usable for sockets 322e, but could be further varied for individual skeletal variations. The inclination angle □ is selected to conform to the curvature of the cervical vertebrae. The angle can vary depending on which vertebrae are joined by the fixation plate 320c, and depending on whether an average curvature is used or on whether variations are made to accommodate an individual's specific spinal curvature. Preferably, the fixation plate 320c is made according to a predetermined curvature such as the average spinal curvature, with the plate being custom bent into a final shape that is based on X-rays of the spinal curvature of a specific user. The fixation plate 320c is inclined about two axes, and thus the legs 322e and 322m on opposing sides of a sagittal plane through the middle of the three openings 376c are inclined toward each other at an angle α of about 6° as best seen in FIG. 56, although the angle can vary a degree or two. The resulting position and inclination of the sockets 322e and 322m allows a lower profile fixation plate as discussed above.

The installation and use of the three level, X-shaped fixation plate 320c is much like the installation and use of the single level plate 20c and two level plate 220c, except that three discs are removed from between three intervening and adjacent vertebrae 30 and three vertebral body replacements 32 are inserted to replace those three removed discs. The replacement bodies 32 can be pre-attached, or they can be attached shortly before insertion, or the bodies 32 can be inserted between vertebrae and the plate 320c can be fastened to the bodies 32. Additionally, if a vertebral replacement body 32 is already in place and a disc is removed from an adjacent vertebrae, then the preexisting body 32 can possibly be left in position and the fixation plate 320c fastened to the preexisting, in-place vertebral replacement body, although it is believed preferable to remove the body 32 and replace it. Indeed, because the fixation plates 20a, 20b, 20c, 220c, 320c are compatible with preexisting vertebral replacement bodies 32, the preexisting and pre-inserted bodies 32 can be left in place and the prior art fixation plates can be replaced with any suitable fixation plate described herein.

Three Level H-Shaped Fixation Plate

Referring to FIGS. 58-64, a further embodiment is shown for fixing four vertebrae and three intervening replacement discs and is believed suited for use in the C3-C6 and C4-C7 cervical portion of the spine. This is referred to as a three-level fixation plate. Most of the parts are the same as described above and that description is not repeated. Parts that are modified have numbers that are incremented by 300, so plate 20a becomes plate 320a. This embodiment uses three H-shaped fixation plates 20a and joins them together in an integral part, referred to herein as plate 320a. The three-level fixation plate 320a has three vertebral replacement bodies 32 fastened to the plate 320a. The three level fixation plate 320a fastens to three vertebrae 30, and thus has sockets 322a and bushings 326a at locations to fasten to the three vertebrae 30. There are thus eight screws 28, eight bushings 326a and eight sockets 322a to receive eight screws 28. The two level fixation plate 320a has three H-shaped plates 320a joined at the sockets 22a common to each H-shaped frame 22a. These are denoted as sockets 322m for "middle" sockets, with the end sockets denoted as 322e for "end."

The two joined H-shaped plates 320a each have four legs 324a as described above. The middle sockets 322m have legs 324a from each H-shaped plate 320a, and thus have two legs 324a attached to each of the middle sockets 322m. The spacing between the legs of each H-shape forming H-shaped plate 320a advantageously form an opening 323a so that the stiffness of the plate 320a at the sockets 322a is more consistent, but the opening could be omitted.

The legs 324a on each segment of fixation plate 320a are thinnest at hole 376a by the connection with the vertebral body replacement 32, and thickest at the juncture with the sockets 322a. This allows the fixation plate 320a to fit close to the vertebrae 30 and helps reduce the amount by which the plate extends away from the vertebrae. This allows a low profile fixation plate which can lie below the muscle tissue and reduce the irritation and discomfort experienced by the user.

The fixation plate 320a is preferably angled or curved slightly about two perpendicular axes intersecting at the center of the three holes 376a in order to better conform to the local spinal shape. Thus, sockets 322e and two sockets 322m on opposing sides of the middle cross-member 270a containing the middle hole 376a are bent or inclined slightly in the same anterior direction so the cross-member 370a is at the apex of a slightly V-shaped plate. Alternately described, the sockets 322e and 322m on opposing sides of the cross-member 370a containing the middle of three holes 376a are bent or inclined relative to the axial plane extending between adjacent, joined vertebrae 30 and extending through the cross-member 370a and the middle of the three openings 376a. The sockets 322e on the superior side of the middle cross-member 370a are inclined slightly toward the sockets 322e on the inferior side of the cross-member and vice-versa. The sockets 322e and legs 324a are inclined at an angle ☐ of about 18° relative to a plane parallel to the coronal plane through the posterior of the middle cross-member 370a, as best seen in FIG. 55. The sockets 322m are inclined at an angle of about 14° as in the two-level plate. Inclination angles can be further varied for individual skeletal variations. The inclination angle ☐ is selected to conform to the curvature of the cervical vertebrae. The angle ☐ can vary depending on which vertebrae are joined by the fixation plate 320a, and depending on whether an average curvature is used or on whether variations are made to accommodate an individual's specific spinal curvature. The fixation plate 320a is inclined about two axes, and thus the legs 322e and 322m on opposing sides of a sagittal plane through the middle of the three openings 376a are inclined toward each other at an angle α of about 6° as best seen in FIG. 56, although the angle can vary a degree or two. The resulting position and inclination of the sockets 322e and 322m allows a lower profile fixation plate as discussed above.

The installation and use of the three level, H-shaped fixation plate 320a is much like the installation and use of the single level plate 20a and two level plate 220a, except that three discs are removed from between three intervening and adjacent vertebrae 30 and three vertebral body replacements 32 are inserted to replace those three removed discs. The replacement bodies 32 can be pre-attached, or they can be attached shortly before insertion, or the bodies 32 can be inserted between vertebrae and the plate 320a can be fastened to the bodies 32. Additionally, if a vertebral replacement body 32 is already in place and a disc is removed from an adjacent vertebrae, then the preexisting body 32 can possibly be left in position and the fixation plate 320a fastened to the preexisting, in-place vertebral replacement body, although it is believed preferable to remove the body 32 and replace it. Indeed, because the fixation plates 20a, 20b, 20c, 220c, 220a, 320c and 320a are compatible with preexisting vertebral replacement bodies 32, the preexisting and pre-inserted bodies 32 can be left in place and the prior art fixation plates can be replaced with any suitable fixation plate described herein.

The inclination of the sockets about two axes helps reduce the profile of the fixation plate and allows the plate to conform to the shape of the vertebrae. To further help maintain this low profile, the thickness of the sockets 22, 222, 322 in the various embodiments are advantageously about 2.1 mm or smaller.

The various fixation plates described herein optionally have an antibiotic coating applied to the fixation plates 20, 220, 320, 420 and associated bushings 26 and screws 28. The antibiotic is preferably in the form of a coating chemically bonded to the fixation plate and part, with the antibiotic advantageously being selected so it can be used in an autoclave to permit the parts to be autoclaved. One suitable antibiotic is believed to be Ceragenin. Chlorhexidine is also believed suitable. Other suitable antibiotics are believed to currently exist and antibiotics developed in the future may also be suitable for use. If the selected antibiotic has any undesirable effects on bone, then only those portions of the fixation plate, screws and bushings which do not contact bone may be coated with the antibiotic, such as the portions of the screw head contained in the fixation plate, the sides and upper surface of the fixation plate and the bushing.

The above disclosure describes two and three level fixation plates. But higher levels of fixation plates can be created by adding additional single plates onto the three-level plate in the same manner that an additional plate is added onto the one-level plates 20a, 20c to make a two level plates 220a, 220c, and in the same manner that an additional plate is added onto the two level plates 220a, 220c to make a three level plate 320a, 320c. Thus four five level fixation plates (four vertebral body replacements 32 and five vertebrae 30) and five level fixation plates (five vertebral body replacements 32 and six vertebrae 30)) can be created using the teaching herein for the X and H frames.

The bending or inclination of the legs 24(a, c) about the saggital plane at an angle α of about 6° is maintained in these higher level fixation plates. The curvature about the axial plane continues to increment at an angle ☐ of about 6° per level or per fixation plate 24(a, c) as with the lower level fixation plates 24, 224, 324, including variations on those inclination angles as described herein. But again, the angle ☐ can vary and is preferably adjusted to meet an individual's spinal curvature prior to use. As the fixation plates reach the three-level and higher the inferior or lowermost fixation plate may be configured to provide less flexibility by limiting the movement of the screws 28. The bushings 26 allow screws 28 to move at an angle ☐ of about 6° relative to a longitudinal axis of the screw, and in the higher level fixation plates this permitted movement may be reduced to 1-2° or even completely eliminated. As discussed above, the permitted movement is preferably adjusted by varying the thickness of flange 50 relative to the recess 74 in the socket 22(a, b, c) of the fixation plate. Some movement is believed desirable to accommodate slight misalignments during installation, but as the number of fixed vertebrae 30 increases, it is believed advantageous to reduce the permitted motion of the inferior or lowest fixation plate.

The various plates 20 (a, b, c), 220 (a, b, c) etc. are made of suitably strong bio-compatible material, such as titanium, a suitable stainless steel, a nitinol or epoxy resin, or other appropriate composition suitable for the specific component. The components such as bushing 26 and screw 28 are made of the same or similar materials as the plates which materials are also suitable for use as bushings and screws, especially including materials such as titanium and suitable stainless steels, with nitinol or epoxy resin being possible materials for the bushing but less desirable. Other suitable materials now in existence or developed hereinafter can be used for the various parts herein.

The above description is given by way of example, and not limitation. Given the above disclosure, one skilled in the art could devise variations that are within the scope and spirit of the invention disclosed herein, including various ways of shaping the projection 28. Further, the various features of the embodiments disclosed herein can be used alone, or in varying combinations with each other and are not intended to be limited to the specific combination described herein. For example, the H shaped plate 20a can be used with a different screw 28 with the sockets 22a being adapted for such screw. The A shaped plate 20b can be used with a different screw 28 with the sockets 22b being adapted for such screw. The X shaped plate 20c can be used with a different screw 28 with the sockets 22c being adapted for such screw. The same applies to the multi-level plates. Likewise, the screw 28 and shaped head 36 and shaped bushing can be used with other fixation plates. Thus, the scope of the claims is not to be limited by the illustrated embodiments.

What is claimed is:

1. A spinal fixation assembly, comprising
a removable bone screw having a shank with threads and a head, the head having a driving socket therein, the head further having a continuously curved spherical outer surface beginning before and continuing past a maximum diameter of the sphere measured orthogonal to a longitudinal axis of the screw;
an annular bushing having a plurality of segments curving away from a base having an outward extending flange that is slit at one location to form a discontinuous ring, the curved segments having an inner wall curved to rotatably receive the curved outer surface of the bone screw, the curved segments having an outer wall that is curved to form a portion of a sphere, the base having a hole through which the threaded shank of the screw extends;
a first, single piece, anterior fixation plate having four legs which legs extend along one of two intersecting lines intersecting at a cross-member to form an X shaped configuration, the legs and cross-member having a predetermined and fixed length and shape and sized for use in spinal fixation;
a socket at a distal end of each leg, each socket having a recess therein with an inward facing surface that is curved to receive and allow rotation of the outer surface of the spherical portion of the bushing, the socket further having an annular recess configured to receive the outward extending flange of the bushing, the annular recess being larger than the outward extending flange to allow the flange and bushing to tilt a predetermined amount depending on a thickness of the outward extending flange, the flange having a hole through which the bone screw can pass but through which the bushing and head of the bone screw do not pass, and wherein the legs have a thickness that is smaller at the cross-member and larger at the socket.

2. The spinal fixation assembly of claim 1, wherein the continuously curved spherical outer surface of the bone screw head, and the inner and outer curved surfaces of the bushing have a common center of curvature.

3. The spinal fixation assembly of claim 1, wherein the continuously curved spherical outer surface of the bone screw head, the inner and outer curved surfaces of the bushing, and the inward facing curved surface of the socket all have a common center of curvature.

4. The spinal fixation assembly of claim 1, wherein the curved spherical outer surface of the bone screw ends at a top edge, and the bushing segments have flanges which resiliently extend over the top edge of the bone screw and restrain removal of the bone screw from the bushing.

5. The spinal fixation assembly of claim 1, wherein the bone screw further has an annular recess in the head located outward of the driving socket and encircling the driving socket, the recess being defined by two opposing sidewalls.

6. The spinal fixation assembly of claim 1, further comprising a vertebral body replacement fastened to the fixation plate.

7. The spinal fixation assembly of claim 1, further comprising a flattened portion on a posterior surface of the cross-member and a portion of each leg.

8. The spinal fixation assembly of claim 1, further comprising a flattened portion on a posterior surface of the cross-member and a flattened portion on an anterior surface of the cross-member.

9. The spinal fixation assembly of claim 1, wherein the fixation plate has an X shape with four legs that include two superior legs and two inferior legs, with a first pair of the superior and inferior legs on a left side of the fixation plate and a second pair of the superior and inferior legs on a right side of the fixation plate, with the sockets on the left and right sides and the associated legs each inclined about an axial plane through the cross-member and inclined in the anterior direction at an angle of about 6 degrees relative to a plane parallel to the coronal plane.

10. The spinal fixation assembly of claim 9, wherein the two superior legs and two inferior legs and the associated sockets are each inclined about a sagittal plane through the middle of the cross-member and inclined in the anterior direction at an angle of about 6 degrees relative to a plane parallel to the coronal plane.

11. The spinal fixation assembly of claim 9, wherein there are a plurality of integrally formed fixation plates having the same construction as the first fixation plate with each plate having at least two superior sockets or two inferior sockets in common with the adjacent plate.

12. The spinal fixation assembly of claim 9, wherein the sockets on the inferior legs of the first fixation plate form the superior sockets on a second fixation plate having the same construction as the first fixation plate.

13. The spinal fixation assembly of claim 10, wherein there are a plurality of integrally formed fixation plates having the same construction as the first fixation plate with each plate having at least two superior sockets or two inferior sockets in common with the adjacent plate.

14. The spinal fixation assembly of claim 10, wherein the sockets on the inferior legs of the first fixation plate form the superior sockets on a second fixation plate having the same construction as the first fixation plate.

15. The spinal fixation assembly of claim 12, wherein the sockets on the superior legs of the first fixation plate form the inferior sockets on a third fixation plate having the same construction as the first fixation plate.

16. The spinal fixation assembly of claim 14, wherein the sockets on the superior legs of the first fixation plate form the inferior sockets on a third fixation plate having the same construction as the first fixation plate.

17. The spinal fixation assembly of claim 1, wherein an antibiotic coating is placed on at least the first fixation plate.

18. A spinal fixation assembly, comprising
a bone screw having a shank with threads and a head, the head having a driving socket therein and a continuously curved spherical outer surface continuing past a maximum diameter of the sphere measured orthogonal to a longitudinal axis of the screw;
an annular bushing having a plurality of segments curving away from a base having an outward extending flange that is slit at one location to form a discontinuous ring, the curved segments having an inner wall curved to rotatably receive the curved outer surface of the bone screw, the curved segments having an outer wall that is curved, the base having a hole through which the threaded shank of the screw extends;
a first, single piece fixation plate having four legs which legs extend along one of two intersecting lines intersecting at a cross-member to form an X shaped configuration, the legs and cross-member having a predetermined and fixed length and shape and sized for use in spinal fixation;
a socket at a distal end of each leg, each socket having a recess therein with an inward facing surface that is curved to receive and allow rotation of the outer surface of the bushing, the socket further having an annular recess configured to receive the outward extending flange of the bushing, the annular recess being larger than the outward extending flange to allow the flange and bushing to tilt a predetermined amount depending on a thickness of the outward extending flange, the flange having a hole through which the bone screw can pass but through which the bushing and head of the bone screw do not pass; and
wherein the continuously curved spherical outer surface of the bone screw head, and the inner and outer curved surfaces of the bushing have a common center of curvature.

19. A spinal fixation assembly, comprising
a bone screw having a shank with threads and a head, the head having a driving socket therein and a continuously curved spherical outer surface continuing past a maximum diameter of the sphere measured orthogonal to a longitudinal axis of the screw;
an annular bushing having a plurality of segments curving away from a base having an outward extending flange that is slit at one location to form a discontinuous ring, the curved segments having an inner wall curved to rotatably receive the curved outer surface of the bone screw, the curved segments having an outer wall that is curved, the base having a hole through which the threaded shank of the screw extends;
a first, single piece fixation plate having four legs which legs extend along one of two intersecting lines intersecting at a cross-member to form an X shaped configuration, the legs and cross-member having a predetermined and fixed length and shape and sized for use in spinal fixation;
a socket at a distal end of each leg, each socket having a recess therein with an inward facing surface that is curved to receive and allow rotation of an outer surface of the bushing, the socket further having an annular recess configured to receive the outward extending flange of the bushing, the annular recess being larger than the outward extending flange to allow the flange and bushing to tilt a predetermined amount depending on a thickness of the outward extending flange, the flange having a hole through which the bone screw can pass but through which the bushing and head of the bone screw do not pass; and
wherein the continuously curved spherical outer surface of the bone screw head, the inner and outer curved surfaces of the bushing, and the inward facing curved surface of the socket all have a common center of curvature.

20. A spinal fixation assembly, comprising
a removable bone screw having a shank with threads and a head, the head having a driving socket therein, the head further having a continuously curved spherical outer surface beginning before and continuing past a maximum diameter of the sphere measured orthogonal to a longitudinal axis of the screw;
an annular bushing having a plurality of segments curving away from a base having an outward extending flange that is slit at one location to form a discontinuous ring, the curved segments having an inner wall curved to rotatably receive the curved outer surface of the bone screw, the curved segments having an outer wall that is curved to form a portion of a sphere, the base having a hole through which the threaded shank of the screw extends;
a first, single piece, anterior fixation plate having four legs which legs extend along one of two intersecting lines intersecting at a cross-member to form an X shaped configuration, the legs and cross-member having a predetermined and fixed length and shape and sized for use in spinal fixation;
a socket at a distal end of each leg, each socket having a recess therein with an inward facing surface that is curved to receive and allow rotation of the outer surface of the spherical portion of the bushing, the socket further having an annular recess configured to receive the outward extending flange of the bushing, the annular recess being larger than the outward extending flange to allow the flange and bushing to tilt a predetermined amount depending on a thickness of the outward extending flange, the flange having a hole through which the bone screw can pass but through which the bushing and head of the bone screw do not pass, and
wherein the continuously curved spherical outer surface of the bone screw head, and the inner and outer curved surfaces of the bushing have a common center of curvature.

21. A spinal fixation assembly, comprising
a removable bone screw having a shank with threads and a head, the head having a driving socket therein, the head further having a continuously curved spherical outer surface beginning before and continuing past a maximum diameter of the sphere measured orthogonal to a longitudinal axis of the screw;
an annular bushing having a plurality of segments curving away from a base having an outward extending flange that is slit at one location to form a discontinuous ring, the curved segments having an inner wall curved to rotatably receive the curved outer surface of the bone screw, the curved segments having an outer wall that is curved to form a portion of a sphere, the base having a hole through which the threaded shank of the screw extends;

a first, single piece, anterior fixation plate having four legs which legs extend along one of two intersecting lines intersecting at a cross-member to form an X shaped configuration, the legs and cross-member having a predetermined and fixed length and shape and sized for use in spinal fixation;

a socket at a distal end of each leg, each socket having a recess therein with an inward facing surface that is curved to receive and allow rotation of the outer surface of the spherical portion of the bushing, the socket further having an annular recess configured to receive the outward extending flange of the bushing, the annular recess being larger than the outward extending flange to allow the flange and bushing to tilt a predetermined amount depending on a thickness of the outward extending flange, the flange having a hole through which the bone screw can pass but through which the bushing and head of the bone screw do not pass;

wherein the continuously curved spherical outer surface of the bone screw head, the inner and outer curved surfaces of the bushing, and the inward facing curved surface of the socket all have a common center of curvature.

22. A spinal fixation assembly, comprising a removable bone screw having a shank with threads and a head, the head having a driving socket therein, the head further having a continuously curved spherical outer surface beginning before and continuing past a maximum diameter of the sphere measured orthogonal to a longitudinal axis of the screw;

an annular bushing having a plurality of segments curving away from a base having an outward extending flange that is slit at one location to form a discontinuous ring, the curved segments having an inner wall curved to rotatably receive the curved outer surface of the bone screw, the curved segments having an outer wall that is curved to form a portion of a sphere, the base having a hole through which the threaded shank of the screw extends;

a first, single piece, anterior fixation plate having four legs which legs extend along one of two intersecting lines intersecting at a cross-member to form an X shaped configuration, the legs and cross-member having a predetermined and fixed length and shape and sized for use in spinal fixation;

a socket at a distal end of each leg, each socket having a recess therein with an inward facing surface that is curved to receive and allow rotation of the outer surface of the spherical portion of the bushing, the socket further having an annular recess configured to receive the outward extending flange of the bushing, the annular recess being larger than the outward extending flange to allow the flange and bushing to tilt a predetermined amount depending on a thickness of the outward extending flange, the flange having a hole through which the bone screw can pass but through which the bushing and head of the bone screw do not pass wherein the continuously curved spherical outer surface of the bone screw head, the inner and outer curved surfaces of the bushing, and the inward facing curved surface of the socket all have a common center of curvature;

wherein the bone screw further has an annular recess in the head located outward of the driving socket and encircling the driving socket, the recess being defined by two opposing sidewalls.

* * * * *